US010501414B2

(12) United States Patent
Powell et al.

(10) Patent No.: US 10,501,414 B2
(45) Date of Patent: Dec. 10, 2019

(54) INDOLE ANALOGS AS 5-OXO-ETE RECEPTOR ANTAGONISTS AND METHOD OF USE THEREOF

(71) Applicants: THE ROYAL INSTITUTION FOR THE ADVANCEMENT OF LEARNING/MCGILL UNIVERSITY, Montreal, Québec (CA); FLORIDA INSTITUTE OF TECHNOLOGY, Melbourne, FL (US)

(72) Inventors: William S. Powell, Québec (CA); Joshua Rokach, Indian Harbour Beach, FL (US)

(73) Assignees: THE ROYAL INSTITUTION FOR THE ADVANCEMENT OF LEARNING/MCGILL UNIVERSITY, Montreal (CA); FLORIDA INSTITUTE OF TECHNOLOGY, Melbourne, FL (US)

( * ) Notice: Subject to any disclaimer, the term of this patent is extended or adjusted under 35 U.S.C. 154(b) by 0 days.

(21) Appl. No.: 15/562,677

(22) PCT Filed: Mar. 29, 2016

(86) PCT No.: PCT/CA2016/050363
§ 371 (c)(1),
(2) Date: Sep. 28, 2017

(87) PCT Pub. No.: WO2016/154749
PCT Pub. Date: Oct. 6, 2016

(65) Prior Publication Data
US 2018/0086702 A1  Mar. 29, 2018

Related U.S. Application Data

(60) Provisional application No. 62/140,732, filed on Mar. 31, 2015.

(51) Int. Cl.
| | | |
|---|---|---|
| *C07D 209/24* | (2006.01) | |
| *C07C 69/34* | (2006.01) | |
| *C07C 69/675* | (2006.01) | |
| *C07C 69/734* | (2006.01) | |
| *A61K 45/06* | (2006.01) | |
| *A61K 31/405* | (2006.01) | |

(52) U.S. Cl.
CPC .......... *C07D 209/24* (2013.01); *A61K 31/405* (2013.01); *A61K 45/06* (2013.01); *C07C 69/34* (2013.01); *C07C 69/675* (2013.01); *C07C 69/734* (2013.01); *C07B 2200/07* (2013.01)

(58) Field of Classification Search
None
See application file for complete search history.

(56) References Cited

U.S. PATENT DOCUMENTS 8,211,934 B2 * 7/2012 Guy ..................... C07D 209/12
514/415
2013/0315384 A1  11/2013 Coster et al.

FOREIGN PATENT DOCUMENTS

WO    2007/025254 A2    3/2007
WO    2010/127452 A1    11/2010

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Grant & Hackh's Chemical Dictionary (5th Ed. 1987) at p. 148.*
Gore et al., 5-Oxo-ETE Receptor Antagonists. Journal of Medicinal Chemistry, 2013, 56, 3725-3732.*
Chourey et al., Novel Highly Potent and Metabolically Resistant Oxoeicosanoid (OXE) Receptor Antagonists That Block the Actions of the Granulocyte Chemoattractant 5-Oxo-6,8,11,14-Eicosatetraenoic Acid (5-oxo-ETE). Journal of Medicinal Chemistry, 2018, 61, 5934-5948.*
Blättermann, S. et al. "A biased ligand for OXE-R uncouples Gα and Gβγ signaling within a heterotrimer" Nature Chemical Biology, vol. 8, Jul. 2012, pp. 631-638.
Brink, C. et al."International Union of Pharmacology XLIV. Nomenclature for the Oxoeicosanoid Receptor" Pharmacological Reviews, Copyright © 2004 by The American Society for Pharmacology and Experimental Therapeuticsvol. 56, No. 1, 2004, pp. 149-157.
Chen, C. et al."Quantitative Analyses of Biochemical Kinetic Resolutions of Enantiomers" American Chemical Society, vol. 104, No. 25, 1982, pp. 7294-7299.
Chourey, S. et al."In vivo a-hydroxylation of a 2-alkylindole antagonist of the OXE receptor for the eosinophil chemoattractant 5-oxo-6,8,11,14-eicosatetraenoic acid in monkeys" Biochemical Pharmacology, vol. 138, 2017, pp. 107-118.
Chourey, S. et al."Novel Highly Potent and Metabolically Resistant Oxoeicosanoid (OXE) Receptor Antagonists That Block the Actions of the Granulocyte Chemoattractant 5-Oxo-6,8,11,14-Eicosatetraenoic Acid (5-oxo-ETE)" Journal of Medicinal Chemistry, vol. 61, pp. 5934-5948.
Cossette, C. et al."Biosynthesis and actions of 5-oxoeicosatetraenoic acid (5-oxo-ETE) on feline granulocytes" Biochemical Pharmacology, vol. 96, 2015, pp. 247-255.
Cossette, C. et al."Pharmacokinetics and Metabolism of Selective Oxoeicosanoid (OXE) Receptor Antagonists and Their Effects on 5-Oxo-6,8,11,14-eicosatetraenoic Acid (5-Oxo-ETE)-Induced Granulocyte Activation in Monkeys" American Chemical Society, Journal of Medicinal Chemistry, vol. 59, 2016, pp. 10127-10146.

(Continued)

*Primary Examiner* — Po-Chih Chen
(74) *Attorney, Agent, or Firm* — Buchanan Ingersoll & Rooney P.C.

(57) ABSTRACT

This invention relates to novel pharmaceutically-useful compounds, to methods for their preparation, and to pharmaceutical compositions and therapeutic methods for treating certain conditions.

14 Claims, 8 Drawing Sheets

(56) References Cited

OTHER PUBLICATIONS

Erlemann, K. et al."Regulation of 5-hydroxyeicosanoid dehydrogenase activity in monocytic cells" Biochem. J., Biochemical Society, vol. 403, 2007, pp. 157-165.
Gelfand, E. W. et al."Mitogen-induced Changes in Ca2+ Permeability Are Not Mediated by Voltage-gated K+ Channels" The Journal of Biological C hemistry, vol. 261, No. 25, Issue of Sep. 5, 1986, pp. 11520-11523.
Gore, V. et al."5-Oxo-ETE Receptor Antagonists" American Chemical Society, J. Med. Chem. vol. 56, 2013, pp. 3725-3732.
Gore, V. et al."Inhibition of 5-Oxo-6,8,11,14-eicosatetraenoic Acid-Induced Activation of Neutrophils and Eosinophils by Novel Indole OXE Receptor Antagonists" American Chemical Society, J. Med. Chem. vol. 57, 2014, pp. 364-377.
Hosoi, T. et al."Identification of a Novel Human Eicosanoid Receptor Coupled to Gi/o" The Journal of Biological Chemistry, vol. 277, No. 35, Issue of Aug. 30, 2002, pp. 31459-31465.
Jones, C. E. et al."Expression and Characterization of a 5-oxo-6E,8Z,11Z,14ZEicosatetraenoic Acid Receptor Highly Expressed on Human Eosinophils and Neutrophils" Molecular Pharmacology vol. 63, No. 3, 2003, pp. 471-477.
Konya, V. et al."A Biased Non-Gαi OXE-R Antagonist Demonstrates That Gαi Protein Subunit Is Not Directly Involved in Neutrophil, Eosinophil, and Monocyte Activation by 5-Oxo-ETE" The Journal of Immunology, vol. 192, 2014, pp. 4774-4782.
Muro, S. et al."5-Oxo-6,8,11,14-eicosatetraenoic acid induces the infiltration of granulocytes into human skin" American Academy of Allergy, Asthma and Immunology, vol. 112, No. 4,Oct. 2003, pp. 768-774.
Patel, P. et al."Structural Requirements for Activation of the 5-Oxo-6E,8Z, 11Z,14Z-eicosatetraenoic Acid (5-OxoETE) Receptor: Identification of a Mead Acid Metabolite with Potent Agonist Activity" The Journal of Pharmacology and Experimental Therapeutics, vol. 325, No. 2, 2008, pp. 698-707.
Patel, P. et al."Two Potent OXE-R Antagonists: Assignment of Stereochemistry" American Chemical Society, ACS Med. Chem. Lett., vol. 5, 2014, pp. 815-819.
Powell, W. S. et al."Metabolism of 5(S)-Hydroxy-6,8,11,14-eicosatetraenoic Acid and Other 5(S)-Hydroxyeicosanoids by a Specific Dehydrogenase in Human Polymorphonuclear Leukocytes" The Journal of Biological Chemistry, vol. 267, No. 27, Issue of Sep. 25, 1992, pp. 19233-19241.
Powell, W. S. et al."5-Oxo-6,8, 11, 14-Eicosatetraenoic Acid Is a Potent Stimulator of Human Eosinophil Migration 1" The American Association of Immunologists, The journal of Immunology, vol. 154. 1995, pp. 4123-4132.
Powell, W. S. et al."Stimulation of Human Neutrophils by 5-oxo-6,8,11,14-Eicosatetraenoic Acid by a Mechanism Independent of the Leukotriene 84 Receptor" The Journal of Biological Chemistry, vol. 268, No. 13, Issue of May 5, 1993, pp. 9280-9286.
Powell, W. S. et al."The eosinophil chemoattractant 5-oxo-ETE and the OXE receptor" Elsevier, Progress in Lipid Research vol. 52, pp. 651-665, 2013.
Powell, W. S. et al.Rapid Extraction of Oxygenated Metabolites of Arachidonic Acid From Biological Samples Using Octadecylsilyl Silica,Prost Aglandins,vol. 20 No. 5, Nov. 1980, pp. 947-957.
Powell, W. S. et al."Precolumn Extraction and Reversed-Phase High-Pressure Liquid Chromatography of Prostaglandins and Leukotrienes" Analytical Biochemistry, vol. 164, 1987, pp. 117-131.
Powell, W. S. et al."Biosynthesis, biological effects, and receptors of hydroxyeicosatetraenoic acids (HETEs) and oxoeicosatetraenoic acids (oxo-ETEs) derived from arachidonic acid" Elsevier, Biochimica et Biophysica Acta, vol. 1851, 2015, pp. 340-355.
Reddy, C. N. et al."Stereoselective synthesis of two highly potent 5-oxo-ETE receptor antagonists" Elsevier, Tetrahedron Letters, vol. 56, pp. 6896-6899, 2015.
Reddy, C. N. et al."Metabolism and pharmacokinetics of a potent N-acylindole antagonist of the OXE receptor for the eosinophil chemoattractant 5-oxo-6,8,11,14-eicosatetraenoic acid (5-oxo-ETE) in rats and monkeys" European Journal of Pharmaceutical Sciences, vol. 115, 2018, pp. 88-99.
Sozzani, S. et al."Stimulating Properties of 5-0xo-Eicosanoids for Human Monocytes" The American Association of Immunologists, The Journal of Immunology, vol. 157. No. 10, 1996, pp. 4664-4671.
Stamatiou, P. B. et al."5-Oxo-6,8,11,14-eicosatetraenoic Acid Stimulates the Release of the Eosinophil Survival Factor Granulocyte/Macrophage Colony-stimulating Factor from Monocytes" The Journal of Biological Chemistry, vol. 279, No. 27, Issue of Jul. 2, 2004, pp. 28159-28164.
Takeda, S. et al."ldentitication of a G Protein-Coupled Receptor for 5-oxo-Eicosatetraenoic Acid" Biomedical Research, vol. 23, No. 2, 2002, pp. 101-108.
Ye, Q. et al."Structure-activity relationship study of β-oxidation resistant indolebased 5-oxo-6,8,11,14-eicosatetraenoic acid (5-oxo-ETE) receptor antagonists" Elsevier, Bioorganic & Medicinal Chemistry Letters, vol. 27, 2017, pp. 4770-4776.

* cited by examiner

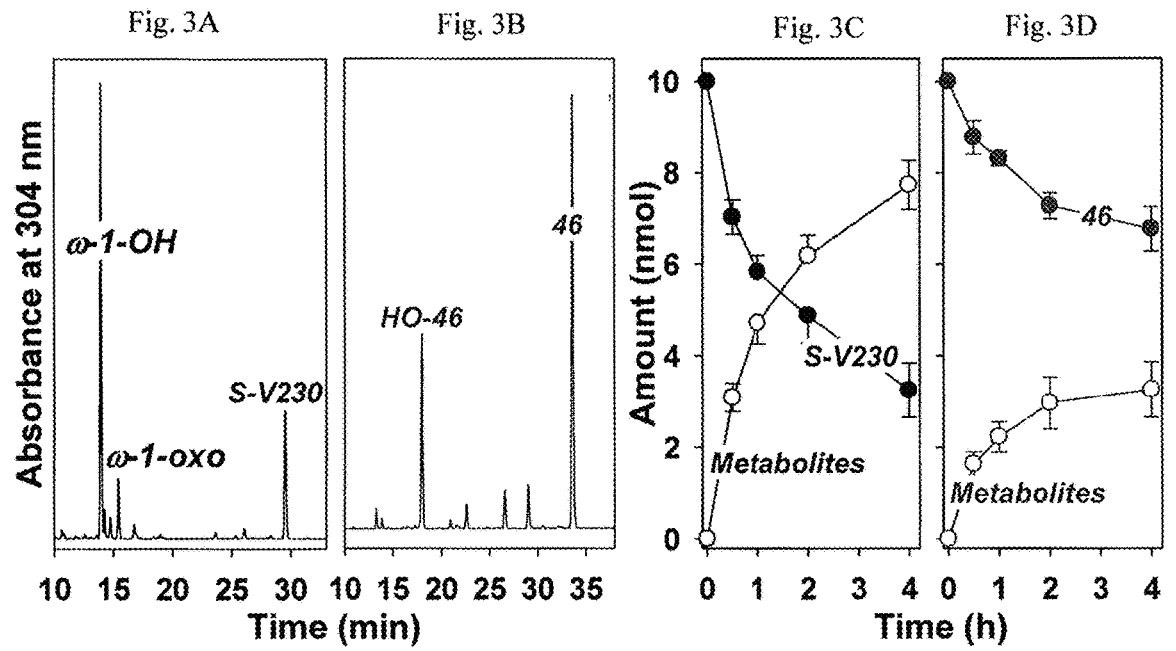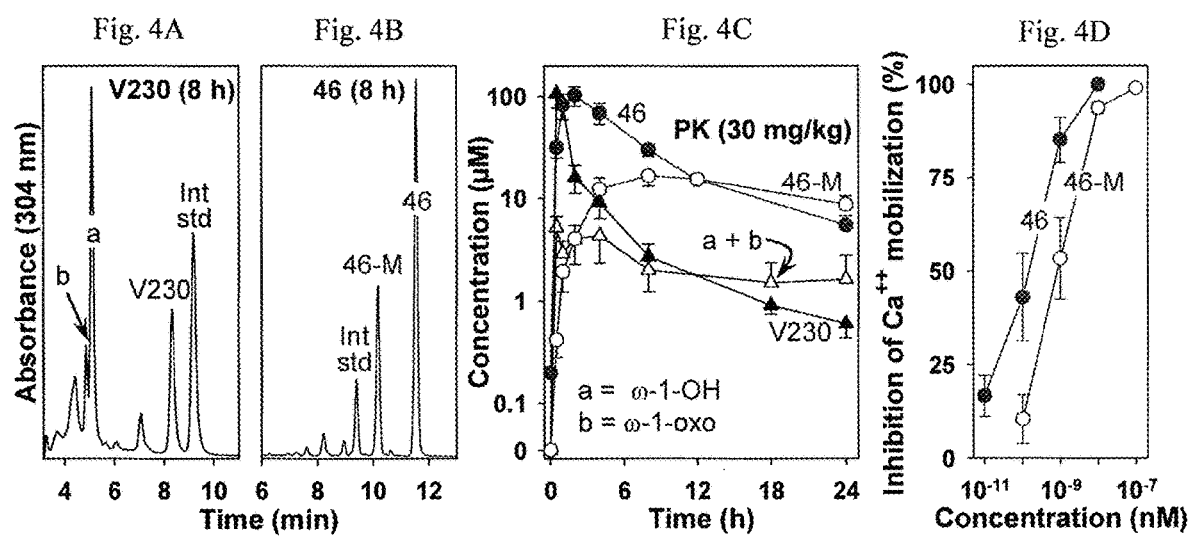

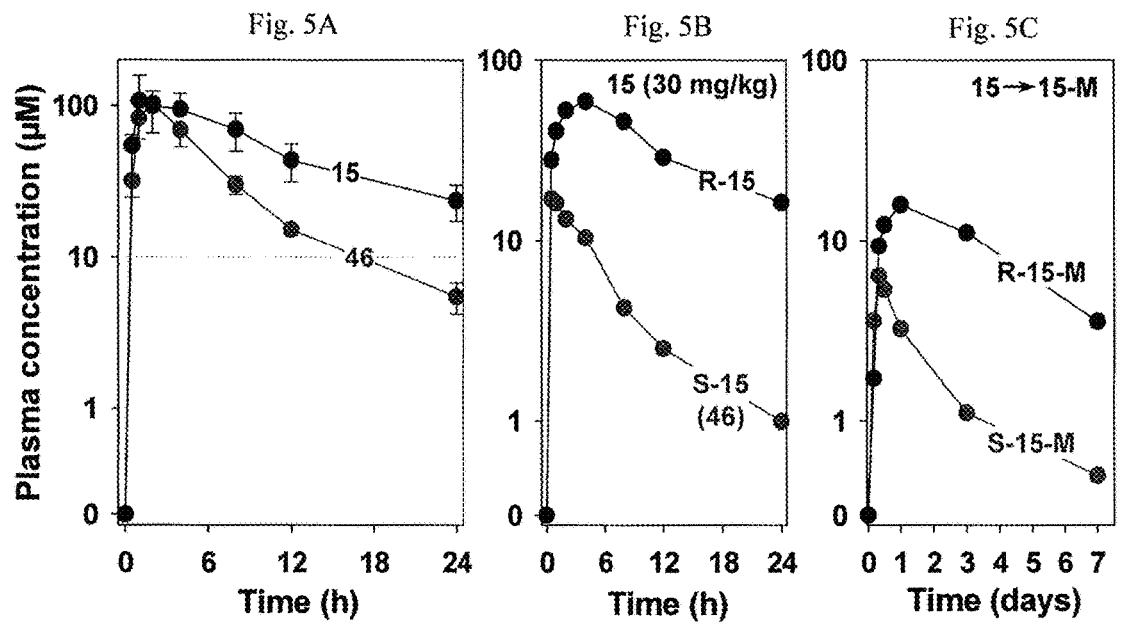
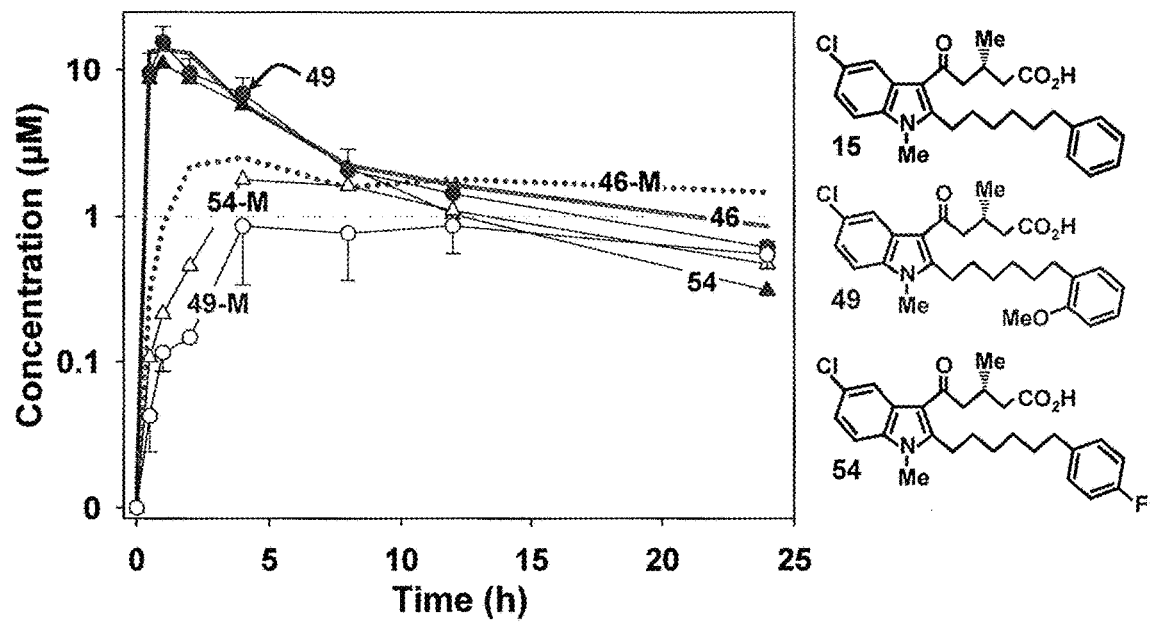
49 (●), metabolite 49-M (○) 54 (▲) metabolite 54-M (△) 46 (solid line) and metabolite 46-M (dotted lines)
Fig. 6

INDOLE ANALOGS AS 5-OXO-ETE RECEPTOR ANTAGONISTS AND METHOD OF USE THEREOF

STATEMENT REGARDING FEDERALLY SPONSORED RESEARCH OR DEVELOPMENT

This invention was made with government support under R01-DK044730 and R01-HL081873 awarded by the National Institutes of Health. The government has certain rights in the invention.

FIELD OF THE DISCLOSURE

This disclosure relates to novel pharmaceutically-useful compounds, to methods for their preparation, and to pharmaceutical compositions and therapeutic methods for treating certain conditions.

BACKGROUND OF THE DISCLOSURE

Arachidonic acid is a key biological intermediate that is converted to a large number of eicosanoids with potent biological activities. Metabolism of arachidonic acid by the 5-lipoxygenase (5-LO) pathway leads to the formation of leukotrienes such as $LTB_4$, $LTC_4$ and $LTD_4$, and 5S-hydroxy-6E,8Z,11Z,14Z-eicosatetraenoic acid (5-HETE). 5-HETE is oxidized to 5-oxo-6,8,11,14-eicosatetraenoic acid (5-oxo-ETE) by the action of 5-hydroxyeicosanoid dehydrogenase, a microsomal enzyme found in leukocytes and platelets, as well as endothelial and epithelial cells.

5-oxo-ETE is a potent chemoattractant for eosinophils and neutrophils, and elicits a variety of rapid responses in these cells. Examples of the responses in these cells in addition to cell migration and tissue infiltration include actin polymerization, calcium mobilization, integrin expression, shedding of L-selectin, degranulation, and superoxide production. The primary target of 5-oxo-ETE is most likely the eosinophil, and among lipid mediators it is the strongest chemoattractant for these cells. It has been shown to induce transendothelial migration of eosinophils and to induce the infiltration of both eosinophils and neutrophils into the skin. 5-oxo-ETE also promotes the survival of eosinophils and possibly other types of inflammatory cells through, for example, the induction of GM-CSF release from monocytes. 5-oxo- is also a chemoattractant for monocytes and has been shown to stimulate the proliferation of prostate tumor cells. The biological effects of 5-oxo-ETE are mediated by a $G_i$ protein-coupled receptor termed the OXE receptor. This receptor is expressed on eosinophils, neutrophils, and monocytes, as well as on prostate tumor cells.

Eicosanoids produced by the 5-LO pathway are known to be important mediators for inflammatory and allergic diseases such as asthma, allergic rhinitis, chronic obstructive pulmonary disorder, atopic dermatitis, psoriasis and acne, and have been shown to play a role in certain cancers such as prostate cancer.

The biological effects of 5-oxo-ETE suggest that agents which block its action may function as therapeutic or prophylactic agents for such diseases.

SUMMARY OF THE DISCLOSURE

In one aspect, there is provided a compound of formula

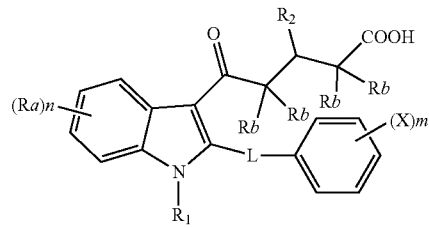

or a pharmaceutically acceptable salt or solvate thereof; wherein $R_1$, $R_2$, Ra, Rb, L, X, m and n are as defined herein.

In another aspect of the disclosure, there is provided a pharmaceutical composition comprising a compound as defined herein or a pharmaceutically acceptable salt or solvate thereof, and one or more pharmaceutically acceptable carrier and/or excipient.

In another aspect of the disclosure, there is provided a combination comprising a therapeutically effective amount of a compound or a pharmaceutically acceptable salt or solvate thereof, as defined herein, and a therapeutically effective amount of one or more therapeutic agents useful in the method of the present disclosure.

In one aspect, there is provided a method, composition, use or combination for treating or preventing a disease or condition as defined herein, the method comprising administering a therapeutically effective amount of a compound or a pharmaceutically acceptable salt or solvate thereof, as defined herein to a subject in need thereof.

In one aspect, there is provided a method, composition, use or combination for antagonizing the 5-oxo-ETE receptors, such as the OXE receptor, the method comprising administering a therapeutically effective amount of a compound or a pharmaceutically acceptable salt or solvate thereof, as defined herein.

In one aspect, there is provided a process and intermediates, for preparing a compound or a pharmaceutically acceptable salt or solvate thereof, as defined herein.

BRIEF DESCRIPTION OF THE DRAWINGS

FIGS. 3A and 3B represents the HPLC traces showing a reference compound and a compound described herein after exposure to monkey liver microsomes;

FIGS. 3C and 3D represent the metabolism of a reference compound and a compound of the present disclosure by monkey liver microsomes;

FIGS. 4A and 4B represent HPLC traces showing a reference compound and a compound described herein isolated from plasma after administration to monkeys;

FIG. 4C illustrates the in vivo metabolism of a reference compound and a compound of the present disclosure in cynomolgus monkeys;

FIG. 4D is the OXE antagonistic activity curve against the concentration of compounds of the present disclosure;

FIGS. 5A, 5B and 5C represent the pharmacokinetics of compounds of the present disclosure in cynomolgus monkeys;

FIG. 6. illustrates the plasma levels of compounds of the present disclosure following oral administration;

DESCRIPTION OF THE EMBODIMENTS

Figure 1:
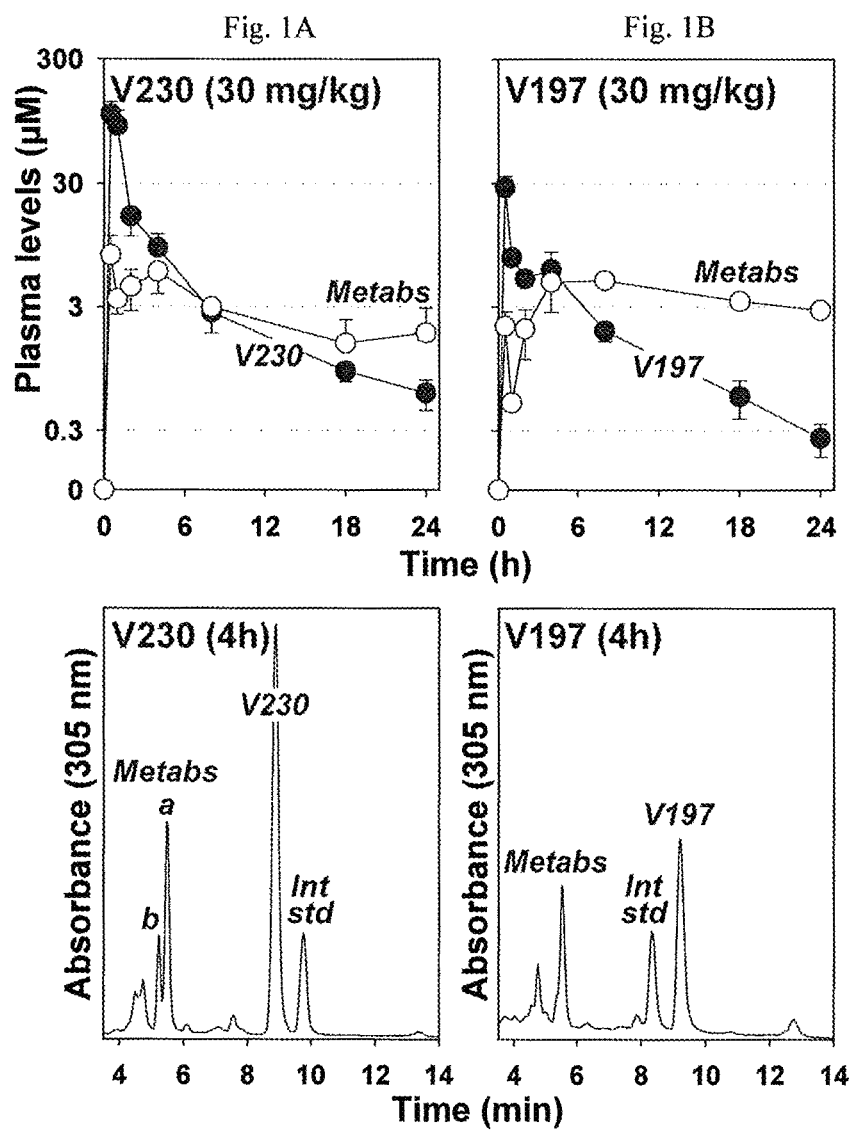
FIGS. 1A and 1B represent the pharmacokinetics of certain reference compounds in cynomolgus monkeys.
FIGS. 1C and 1D represent HPLC traces showing certain reference compounds obtained from plasma after administration to cynomolgus monkeys.

This description provides novel 5-(2-(alkylphenyl)-indol-3-yl)-5-oxopentanoic acid compounds that offer advantageous properties having regard to previously described 5-(2-(alkyl)-indol-3-yl)-5-oxopentanoic acid compounds. The compounds provide an increased potency and/or one or more improved pharmacokinetic (PK) characteristics.

In accordance with one embodiment, there is provided a compound of formula

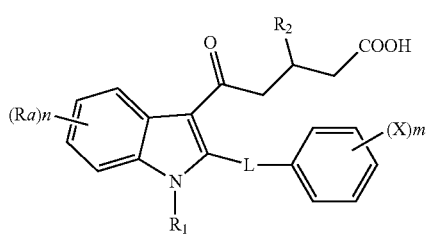

or a pharmaceutically acceptable salt or solvate thereof; wherein $R_1$, $R_2$, Ra, L, X, m and n are as defined herein.

In accordance with a further embodiment, there is provided a compound of formula

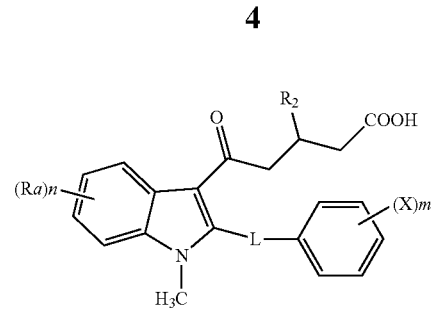

or a pharmaceutically acceptable salt or solvate thereof; wherein $R_2$, Ra, L, X, m and n are as defined herein.

In accordance with a further embodiment, there is provided a compound of formula

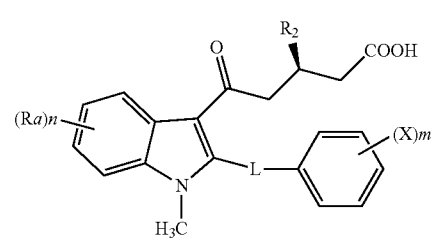

or a pharmaceutically acceptable salt or solvate thereof; wherein $R_2$, Ra, L, X, m and n are as defined herein.

In accordance with a further embodiment, there is provided a compound of formula

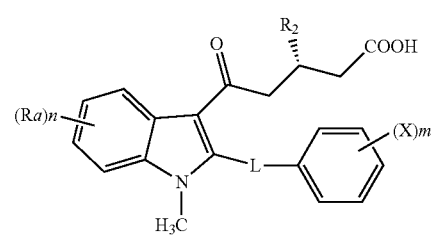

or a pharmaceutically acceptable salt or solvate thereof; wherein $R_2$, Ra, L, X, m and n are as defined herein.

In accordance with a further embodiment, there is provided a compound of formula

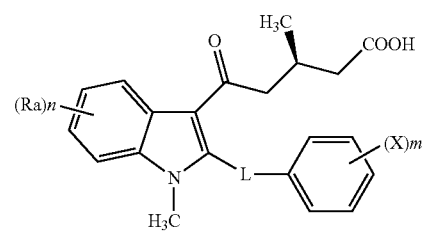

or a pharmaceutically acceptable salt or solvate thereof; wherein Ra, L, X, m and n are as defined herein.

In accordance with a further embodiment, there is provided a compound of formula

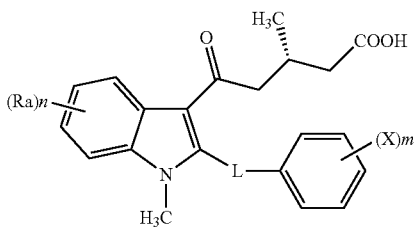

VII or a pharmaceutically acceptable salt or solvate thereof; wherein Ra, L, X, m and n are as defined herein.

In one embodiment, having regard to any above-described embodiment,

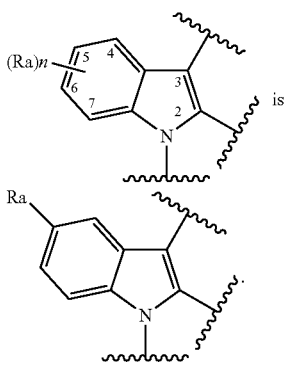

is

In one embodiment, having regard to any above described embodiment,

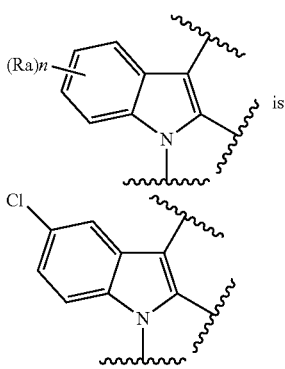

is

In accordance with a further embodiment, there is provided a compound of formula

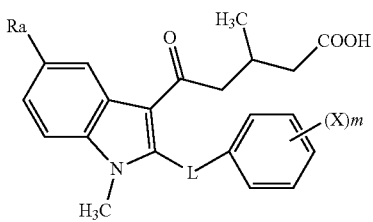

VIII

In accordance with a further embodiment, there is provided a compound of formula

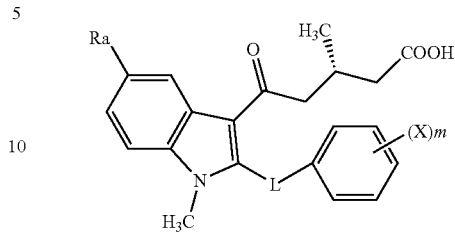

IX

In accordance with a further embodiment, there is provided a compound of formula

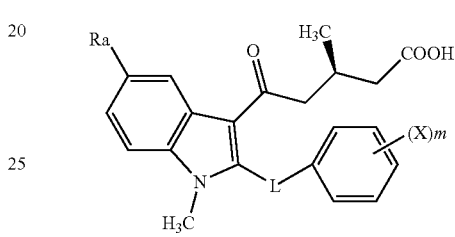

X

In one embodiment, $R_1$ is H, a straight or branched alkyl, or lower cycloalkyl. In one embodiment, $R_1$ is H. In one embodiment, $R_1$ is a lower straight or branched alkyl. In one embodiment, $R_1$ is a straight alkyl of 1-3 carbon atoms, or branched alkyl of 3 carbon atoms. In one embodiment, $R_1$ is lower cycloalkyl. In one embodiment, $R_1$ is a methyl, ethyl, n-propyl or isopropyl. In one embodiment, $R_1$ is a methyl.

In one embodiment, $R_2$ is a lower straight or branched alkyl or lower cycloalkyl. In one embodiment, $R_2$ is a lower straight or branched alkyl. In one embodiment, $R_2$ is a straight alkyl of 1-3 carbon atoms, or branched alkyl of 3 carbon atoms. In one embodiment, $R_2$ is a methyl, ethyl, n-propyl or isopropyl. In one embodiment, $R_2$ is a methyl.

In one embodiment, L is an alkylene chain of 4-7 members, an alkenylene chain of 4-7 members, a CH(OH)-alkylene chain (the alkylene comprising 4-6 members) or an alkylene-O-alkylene chain (the two alkylene chains together comprising a total of 4-6 members).

In one embodiment, L is an alkylene chain of 4-6 members, an alkenylene chain of 4-6 members or an alkylene-O-alkylene chain of 4-6 members.

In one embodiment, L is an alkylene chain of 4-7 members. In one embodiment, L is a CH(OH)-alkylene chain (the alkylene comprising 4-6 members).

In one embodiment, L is an alkylene chain of 4-6 members. In one embodiment, L is an alkenylene chain of 4-6 members. In one embodiment, L is an alkylene chain of 5-6 members. In one embodiment, L is an alkylene-O-alkylene chain of 4-6 members.

Preferably, when L includes an alkenylene chain, the double bond is in a trans relationship.

In one embodiment, L is —CH(OH)—$(CH_2)_6$—, or —CH(OH)—$(CH_2)_5$—.

In one embodiment, L is —CH(OH)—$(CH_2)_6$—, —$(CH_2)_7$—, —$(CH_2)_6$—, —CH(OH)—$(CH_2)_5$—, —$(CH_2)_5$—, —$(CH_2)_4$—, —$CH_2$—O—$(CH_2)_3$—, —$CH_2$—O—$(CH_2)_3$—, —$(CH_2)_2$—O—$(CH_2)_2$—, —$(CH_2)_3$—O—$(CH_2)$—, —CH=CH—$(CH_2)_4$—, —CH$_2$—CH=CH—(CH$_2$)$_3$—, —(CH$_2$)$_2$—CH=CH—(CH$_2$)$_2$—, —(CH$_2$)$_3$—CH=CH—CH$_2$— or —(CH$_2$)$_4$—CH=CH—.

In one embodiment, L is —(CH$_2$)$_6$—, —(CH$_2$)$_5$—, —(CH$_2$)$_4$—, —CH$_2$—O—(CH$_2$)$_3$—, —CH$_2$—O—(CH$_2$)$_3$—, —(CH$_2$)$_2$—O—(CH$_2$)$_2$—, —(CH$_2$)$_3$—O—(CH$_2$)—, —CH=CH—(CH$_2$)$_4$—, —CH$_2$—CH=CH—(CH$_2$)$_3$—, —(CH$_2$)$_2$—CH=CH—(CH$_2$)$_2$—, —(CH$_2$)$_3$—CH=CH—CH$_2$— or —(CH$_2$)$_4$—CH=CH—.

In one embodiment, L is —CH(OH)—(CH$_2$)$_6$—, —(CH$_2$)$_7$—, —(CH$_2$)$_6$—, —CH(OH)—(CH$_2$)$_5$—, —(CH$_2$)$_5$—, —CH$_2$—O—(CH$_2$)$_3$—, —CH$_2$—O—(CH$_2$)$_3$—, —(CH$_2$)$_2$—O—(CH$_2$)$_2$—, —(CH$_2$)$_3$—O—(CH$_2$)—, (CH$_2$)$_4$—, —CH$_2$—CH=CH—(CH$_2$)$_3$—, —(CH$_2$)$_2$—CH=CH—(CH$_2$)$_2$—, —(CH$_2$)$_3$—CH=CH—CH$_2$— or —(CH$_2$)$_4$—CH=CH—.

In one embodiment, L is —(CH$_2$)$_6$—, —(CH$_2$)$_5$—, —CH$_2$—O—(CH$_2$)$_3$—, —CH$_2$—O—(CH$_2$)$_3$—, —(CH$_2$)$_2$—O—(CH$_2$)$_2$—, —(CH$_2$)$_3$—O—(CH$_2$)—, —CH=CH—(CH$_2$)$_4$—, —CH$_2$—CH=CH—(CH$_2$)$_3$—, —(CH$_2$)$_2$—CH=CH—(CH$_2$)$_2$—, —(CH$_2$)$_3$—CH=CH—CH$_2$— or —(CH$_2$)$_4$—CH=CH—.

In one embodiment, L is —CH(OH)—(CH$_2$)$_6$—, —(CH$_2$)$_7$—, —(CH$_2$)$_6$—, —CH(OH)—(CH$_2$)$_5$—, —(CH$_2$)$_5$—, —(CH$_2$)$_4$—, —CH$_2$—O—(CH$_2$)$_3$—, —CH$_2$—O—(CH$_2$)$_3$—, —(CH$_2$)$_2$—O—(CH$_2$)$_2$—, —(CH$_2$)$_3$—O—(CH$_2$)—, (cis)-CH=CH—(CH$_2$)$_4$—, (cis)-CH$_2$—CH=CH—(CH$_2$)$_3$—, (cis)-(CH$_2$)$_2$—CH=CH—(CH$_2$)$_2$—, (cis)-(CH$_2$)$_3$—CH=CH—CH$_2$—, (cis)-(CH$_2$)$_4$—CH=CH—, (trans)-CH=CH—(CH$_2$)$_4$—, (trans)-CH$_2$—CH=CH—(CH$_2$)$_3$—, (trans)-(CH$_2$)$_2$—CH=CH—(CH$_2$)$_2$—, (trans)-(CH$_2$)$_3$—CH=CH—CH$_2$— or (trans)—(CH$_2$)$_4$—CH=CH—.

In one embodiment, L is —(CH$_2$)$_6$—, —(CH$_2$)$_5$—, —(CH$_2$)$_4$—, —CH$_2$—O—(CH$_2$)$_3$—, —CH$_2$—O—(CH$_2$)$_3$, —(CH$_2$)$_2$—O—(CH$_2$)$_2$—, —(CH$_2$)$_3$—O—(CH$_2$)—, (cis)-CH=CH—(CH$_2$)$_4$—, (cis)-CH$_2$—CH=CH—(CH$_2$)$_3$—, (cis)-(CH$_2$)$_2$—CH=CH—(CH$_2$)$_2$—, (cis)-(CH$_2$)$_3$—CH=CH—CH$_2$—, (cis)-(CH$_2$)$_4$—CH=CH—, (trans)-CH=CH—(CH$_2$)$_4$—, (trans)-CH$_2$—CH=CH—(CH$_2$)$_3$—, (trans)-(CH$_2$)$_2$—CH=CH—(CH$_2$)$_2$—, (trans)-(CH$_2$)$_3$—CH=CH—CH$_2$— or (trans)-(CH$_2$)$_4$—CH=CH—.

In one embodiment, L is —CH(OH)—(CH$_2$)$_6$—, —(CH$_2$)$_7$—, —(CH$_2$)$_6$—, or —CH(OH)—(CH$_2$)$_5$—. In one embodiment, L is —CH(OH)—(CH$_2$)$_5$— or —CH(OH)—(CH$_2$)$_6$—. In one embodiment, L is —(CH$_2$)$_6$—, —(CH$_2$)$_5$—, or —(CH$_2$)$_4$—. In one embodiment, L is —(CH$_2$)$_6$— or —(CH$_2$)$_5$—. In one embodiment, L is —(CH$_2$)$_6$—. In one embodiment, L is —(CH$_2$)$_5$—. In one embodiment, L is —(CH$_2$)$_4$—. In one embodiment, L is —CH$_2$—O—(CH$_2$)$_3$—. In one embodiment, L is —CH$_2$—O—(CH$_2$)$_3$—. In one embodiment, L is —(CH$_2$)$_2$—O—(CH$_2$)$_2$—. In one embodiment, L is —(CH$_2$)$_3$—O—(CH$_2$)—. In one embodiment, L is (cis)-CH=CH—(CH$_2$)$_4$—. In one embodiment, L is (cis)-CH$_2$—CH=CH—(CH$_2$)$_3$—. In one embodiment, L is (cis)-(CH$_2$)$_2$—CH=CH—(CH$_2$)$_2$—. In one embodiment, L is (cis)-(CH$_2$)$_3$—CH=CH—CH$_2$—. In one embodiment, L is (cis)-(CH$_2$)$_4$—CH=CH—. In one embodiment, L is (trans)-CH=CH—(CH$_2$)$_4$—. In one embodiment, L is (trans)-CH$_2$—CH=CH—(CH$_2$)$_3$—. In one embodiment, L is (trans)-(CH$_2$)$_2$—CH=CH—(CH$_2$)$_2$—. In one embodiment, L is (trans)-(CH$_2$)$_3$—CH=CH—CH$_2$—. In one embodiment, L is (trans)-(CH$_2$)$_4$—CH=CH—.

In one embodiment, m is an integer of 0 to 5 and X is a substituent as defined herein.

In one embodiment, m is an integer of 0 to 5 and X is halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl.

In one embodiment, m is an integer of 0 to 3 and X is halogen, C1-6alkyl, C1-6 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-6alkyl.

In one embodiment, m is an integer of 0 to 3 and X is F, Cl, C1-3alkyl, C1-3 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-3alkyl.

In one embodiment, m is an integer of 0 to 2 and X is F, Cl, C1-3alkyl, C1-3 alkoxy, or hydroxyl. In one embodiment, m is an integer of 0 or 1 and X is F, Cl, C1-3alkyl, C1-3 alkoxy, or hydroxyl. In one embodiment, m is an integer of 0 or 1 and X is F, Cl, C1-3 alkoxy, or hydroxyl. In one embodiment, m is an integer of 0 or 1 and X is F, Cl, methoxy, or hydroxyl.

In one embodiment,

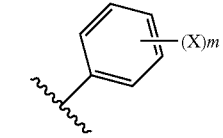

is

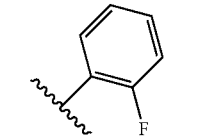 X1

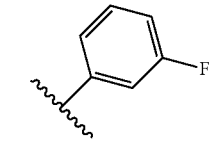 X2

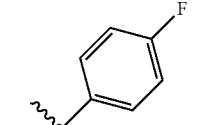 X3

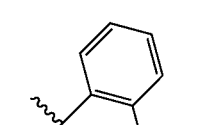 X4

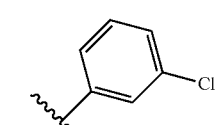 X6

-continued

X7 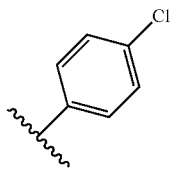

X8 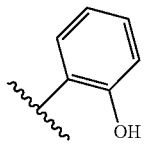

X9 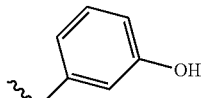

X10 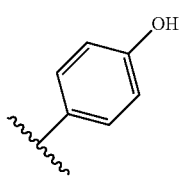

X11 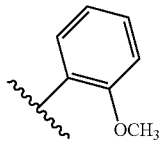

X12 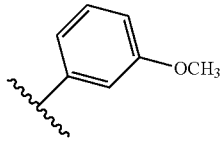

X13 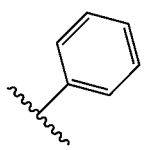

or

X14

In one embodiment, n is an integer of 0 to 4 and Ra is a substituent as defined herein.

In one embodiment, n is an integer of 0 to 4 and Ra is halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl.

In one embodiment, n is an integer of 0 to 3 and Ra is halogen, C1-6alkyl, C1-6 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-6alkyl.

In one embodiment, n is an integer of 0 to 3 and Ra is F, Cl, C1-3alkyl, C1-3 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-3alkyl.

In one embodiment, n is an integer of 0 to 2 and Ra is F, Cl, C1-3alkyl, C1-3 alkoxy, or hydroxyl. In one embodiment, n is an integer of 0 or 1 and Ra is F, Cl, C1-3alkyl, C1-3 alkoxy, or hydroxyl. In one embodiment, n is an integer of 0 or 1 and Ra is F, Cl, or C1-3 alkoxy. In one embodiment, n is 1 and Ra is F, Cl, or methoxy. In one embodiment, n is 1 and Ra is Cl, preferably Cl at position C-5. In one embodiment, n is 0.

In one embodiment, Rb is H or F. In one embodiment, Rb is H.

In one embodiment, R$_1$ is H, a straight or branched alkyl, or lower cycloalkyl; R$_2$ is a lower straight or branched alkyl or lower cycloalkyl; L is an alkylene chain of 4-7 members, a CH(OH)-alkylene chain (the alkylene comprising 4-6 members), an alkenylene chain of 4-6 members or an alkylene-O-alkylene chain of 4-6 members; m is an integer of 0 to 5 and X is halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl; n is an integer of 0 to 4 and Ra is halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl; and Rb is H or F.

In one embodiment, R$_1$ is H, a straight or branched alkyl, or lower cycloalkyl; R$_2$ is a lower straight or branched alkyl or lower cycloalkyl; L is an alkylene chain of 4-6 members, an alkenylene chain of 4-6 members or an alkylene-O-alkylene chain of 4-6 members; m is an integer of 0 to 5 and X is halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl; n is an integer of 0 to 4 and Ra is halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl; and Rb is H or F.

In one embodiment, R$_1$ is a lower straight or branched alkyl; R$_2$ is a lower straight or branched alkyl; L is an alkylene chain of 4-6 members or a CH(OH)-alkylene chain (the alkylene comprising 4-6 members); m is an integer of 0 to 3 and X is halogen, C1-6alkyl, C1-6 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-6alkyl; n is an integer of 0 to 3 and Ra is halogen, C1-6alkyl, C1-6 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-6alkyl; and Rb is H.

In one embodiment, R$_1$ is a lower straight or branched alkyl; R$_2$ is a lower straight or branched alkyl; L is an alkylene chain of 4-6 members; m is an integer of 0 to 3 and X is halogen, C1-6alkyl, C1-6 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-6alkyl; n is an integer of 0 to 3 and Ra is halogen, C1-6alkyl, C1-6 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-6alkyl; and Rb is H.

In one embodiment, $R_1$ is a methyl, ethyl, n-propyl or isopropyl; $R_2$ is a methyl, ethyl, n-propyl or isopropyl; L is —CH(OH)—(CH$_2$)$_6$—, —CH(OH)—(CH$_2$)$_5$—, m is an integer of 0 to 2 and X is F, Cl, C1-3alkyl, C1-3 alkoxy, or hydroxyl; n is an integer of 0 to 2 and Ra is F, Cl, C1-3alkyl, C1-3 alkoxy, or hydroxyl; and Rb is H.

In one embodiment, $R_1$ is a methyl, ethyl, n-propyl or isopropyl; $R_2$ is a methyl, ethyl, n-propyl or isopropyl; L is —CH(OH)—(CH$_2$)$_6$—, —CH(OH)—(CH$_2$)$_5$—, n is an integer of 0 to 2 and Ra is F, Cl, C1-3alkyl, C1-3 alkoxy, or hydroxyl; Rb is H; and

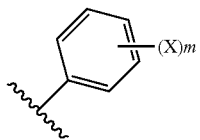

is any one of X1-X14.

In one embodiment, $R_1$ is a methyl, ethyl, n-propyl or isopropyl; $R_2$ is a methyl, ethyl, n-propyl or isopropyl; L is —CH(OH)—(CH$_2$)$_6$—, —(CH$_2$)$_7$—, —(CH$_2$)$_6$—, —CH(OH)—(CH$_2$)$_5$—, —CH$_2$—O—(CH$_2$)$_3$—, —(CH$_2$)$_2$—O—(CH$_2$)$_2$—, —(CH$_2$)$_3$—O—(CH$_2$)—, —CH═CH—(CH$_2$)$_2$—, —CH$_2$—CH═CH—(CH$_2$)$_3$—, —(CH$_2$)$_2$—CH═CH—(CH$_2$)$_2$—, or —(CH$_2$)$_3$—CH═CH—CH$_2$—; m is an integer of 0 to 2 and X is F, Cl, C1-3alkyl, C1-3 alkoxy, or hydroxyl; n is an integer of 0 to 2 and Ra is F, Cl, C1-3alkyl, C1-3 alkoxy, or hydroxyl; and Rb is H.

In one embodiment, $R_1$ is a methyl, ethyl, n-propyl or isopropyl; $R_2$ is a methyl, ethyl, n-propyl or isopropyl; L is —CH(OH)—(CH$_2$)$_6$—, —(CH$_2$)$_7$—, —(CH$_2$)$_6$—, —CH(OH)—(CH$_2$)$_5$—, —CH$_2$—O—(CH$_2$)$_3$—, —(CH$_2$)$_2$—O—(CH$_2$)$_2$—, —(CH$_2$)$_3$—O—(CH$_2$)—, —CH═CH—(CH$_2$)$_4$—, —CH$_2$—CH═CH—(CH$_2$)$_3$—, —(CH$_2$)$_2$—CH═CH—(CH$_2$)$_2$—, or —(CH$_2$)$_3$—CH═CH—CH$_2$—; n is an integer of 0 to 2 and Ra is F, Cl, C1-3alkyl, C1-3 alkoxy, or hydroxyl; Rb is H; and

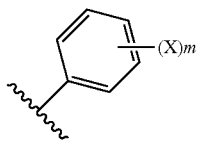

is any one of X1-X14.

In one embodiment, $R_1$ is a methyl, ethyl, n-propyl or isopropyl; $R_2$ is a methyl, ethyl, n-propyl or isopropyl; L is —(CH$_2$)$_6$—, —CH$_2$—O—(CH$_2$)$_3$—, —(CH$_2$)$_2$—O—(CH$_2$)$_2$—, —(CH$_2$)$_3$—O—(CH$_2$)—, —CH═CH—(CH$_2$)$_4$—, —CH$_2$—CH═CH—(CH$_2$)$_3$—, —(CH$_2$)$_2$—CH═CH—(CH$_2$)$_2$—, or —(CH$_2$)$_3$—CH═CH—CH$_2$—; m is an integer of 0 to 2 and X is F, Cl, C1-3alkyl, C1-3 alkoxy, or hydroxyl; n is an integer of 0 to 2 and Ra is F, C1-3alkyl, C1-3 alkoxy, or hydroxyl; and Rb is H.

In one embodiment, $R_1$ is a methyl, ethyl, n-propyl or isopropyl; $R_2$ is a methyl, ethyl, n-propyl or isopropyl; L is —CH(OH)—(CH$_2$)$_6$—, —(CH$_2$)$_7$—, —(CH$_2$)$_6$—, —CH(OH)—(CH$_2$)$_5$—, —(CH$_2$)$_5$—, or —(CH$_2$)$_4$—; m is an integer of 0 or 1 and X is F, Cl, C1-3 alkoxy, or hydroxyl; n is 1 and Ra is F, Cl, or methoxy; and Rb is H.

In one embodiment, $R_1$ is a methyl, ethyl, n-propyl or isopropyl; $R_2$ is a methyl, ethyl, n-propyl or isopropyl; L is —CH(OH)—(CH$_2$)$_6$—, —(CH$_2$)$_7$—, —(CH$_2$)$_6$—, —CH(OH)—(CH$_2$)$_5$—, —(CH$_2$)$_5$—, or —(CH$_2$)$_4$—; n is 1 and Ra is F, Cl, or methoxy; Rb is H; and

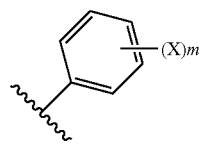

is any one of X1-X14.

In one embodiment, $R_1$ is a methyl, ethyl, n-propyl or isopropyl; $R_2$ is a methyl, ethyl, n-propyl or isopropyl; L is —CH(OH)—(CH$_2$)$_6$—, or —CH(OH)—(CH$_2$)$_5$—, m is an integer of 0 or 1 and X is F, Cl, C1-3 alkoxy, or hydroxyl; n is 1 and Ra is F, Cl, or methoxy; and Rb is H.

In one embodiment, $R_1$ is a methyl, ethyl, n-propyl or isopropyl; $R_2$ is a methyl, ethyl, n-propyl or isopropyl; L is —CH(OH)—(CH$_2$)$_6$—, or —CH(OH)—(CH$_2$)$_5$—; n is 1 and Ra is F, Cl, or methoxy; Rb is H; and

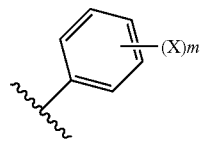

is any one of X1-X14.

In one embodiment, $R_1$ is a methyl, ethyl, n-propyl or isopropyl; $R_2$ is a methyl, ethyl, n-propyl or isopropyl; L is —(CH$_2$)$_7$—, —(CH$_2$)$_6$—, —(CH$_2$)$_5$—, or —(CH$_2$)$_4$—; m is an integer of 0 or 1 and X is F, Cl, C1-3 alkoxy, or hydroxyl; n is 1 and Ra is F, Cl, or methoxy; and Rb is H.

In one embodiment, $R_1$ is a methyl, ethyl, n-propyl or isopropyl; $R_2$ is a methyl, ethyl, n-propyl or isopropyl; L is —(CH$_2$)$_7$—, —(CH$_2$)$_6$—, —(CH$_2$)$_5$—, or —(CH$_2$)$_4$—; n is 1 and Ra is F, Cl, or methoxy; Rb is H; and

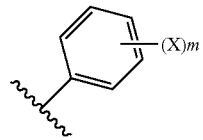

is any one of X1-X14.

In one embodiment, $R_1$ is a methyl, ethyl, n-propyl or isopropyl; $R_2$ is a methyl, ethyl, n-propyl or isopropyl; L is —(CH$_2$)$_6$—, —(CH$_2$)$_5$—, or —(CH$_2$)$_4$—; m is an integer of 0 or 1 and X is F, Cl, C1-3 alkoxy, or hydroxyl; n is 1 and Ra is F, Cl, or methoxy; and Rb is H.

In one embodiment, R₁ is a methyl; R₂ is a methyl; L is —(CH₂)₇—, m is an integer of 0 or 1 and X is F, Cl, methoxy, or hydroxyl; n is 1 and Ra is Cl, preferably Cl at position C-5 and Rb is H.

In one embodiment, R₁ is a methyl; R₂ is a methyl; L is —(CH₂)₆—, m is an integer of 0 or 1 and X is F, Cl, methoxy, or hydroxyl; n is 1 and Ra is Cl, preferably Cl at position C-5 and Rb is H.

In one embodiment, R₁ is a methyl; R₂ is a methyl; L is —(CH₂)₇—, —CH(OH)—(CH₂)₆—, or —(CH₂)₆—, or —CH(OH)—(CH₂)₅—; n is 1 and Ra is Cl, and

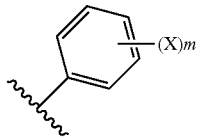

is any one of X1-X14.

The term "alkyl", as used herein, is understood as referring to a saturated, monovalent unbranched or branched hydrocarbon chain. Examples of alkyl groups include, but are not limited to, C1-10 alkyl groups, provided that branched alkyls comprise at least 3 carbon atoms, such as C3-10. Lower straight alkyl may have 1 to 6 or preferably 1 to 3 carbon atoms; whereas branched lower alkyl comprise C3-6. Examples of alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl. The term "alkyl" is also meant to include alkyls in which one or more hydrogen atom is replaced by a halogen, ie. an haloalkyl including fluoroalkyls of all alkyls defined above: straight or branched fluoroalkyls and straight or branched lower fluoroalkyls, such as trifluoromethyl, difluoromethyl, fluoromethyl, trichloromethyl, dichloromethyl, chloromethyl, trifluoroethyl, difluoroethyl, fluoroethyl.

The term "alkylene", as used herein, is understood as referring to an alkyl residue being bivalent. In the context of use in the definition of variable L herein, an alkylene is connected to both the C-2 position of the indole residue and the phenyl group.

The terms "alkenyl" represent optionally substituted linear or branched hydrocarbon moiety which has one or more double bonds, preferably one, in the chain. The number of carbon atoms can be the same as those in "alkyl" provided that there is at least 2 carbon atoms.

The term "alkenylene", as used herein, is understood as referring to an alkenyl residue being bivalent. In the context of use in the definition of variable L herein, an alkenylene is connected to both the C-2 position of the indole residue and the phenyl group.

The terms "alkoxy," represent an alkyl, alkenyl or alkynyl moiety, respectively, which is covalently bonded to the adjacent atom through an oxygen atom.

The term "aryl" represents carbocyclic moiety containing at least one benzenoid-type ring (i.e., may be monocyclic or polycyclic). Examples include but are not limited to phenyl, tolyl, dimethylphenyl, aminophenyl, anilinyl, naphthyl, anthryl, phenanthryl or biphenyl. Preferably, the aryl comprises 6 to 10 or more preferably 6 carbon atoms.

The term "cycloalkyl" represents optionally substituted cyclic hydrocarbon moiety having 3 to 10 carbon atoms. Examples of "cycloalkyl" groups include but are not limited to cyclopropyl, cyclobutyl, cyclopentyl, and cyclohexyl. Lower cycloalkyls comprise 3 to 6, or alternatively any of 3, 4, 5 or 6 carbon atoms. This term includes without limitation, for example, cyclopropyl, cyclobutyl, cyclopentyl and cyclohexyl.

The term "heteroaryl" represents a 5 to 11 membered aromatic cyclic moiety wherein said cyclic moiety is comprising at least one heteroatom selected from oxygen (O), sulfur (S) or nitrogen (N). Heteroaryls may be monocyclic or polycyclic rings. Heteroaryls may be 5 to 6 membered monocyclic ring or 5 membered monocyclic ring or 6 membered monocyclic ring. membered monocyclic ring may be 7 to 12 membered bicyclic ring or 9 to 10 membered bicyclic ring. When heteroaryl is a polycyclic ring, the rings comprise at least one ring comprising the heteroatom and the other rings may be cycloalkyl, aryl or heterocycle and the point of attachment may be on any available atom. This term includes without limitation, for example, furyl, thienyl, pyrrolyl, imidazolyl, oxazolyl, thiazolyl, triazolyl, tetrazolyl, pyridyl, pyrazinyl, pyrimidinyl, pyridazinyl, quinolinyl, isoquinolinyl, indolyl.

The term "heterocycle" represents a 3 to 11 membered saturated, partially saturated (i.e. comprising one or more double bonds provided that it is not aromatic) cyclic moiety wherein said cyclic moiety is comprising at least one heteroatom selected from oxygen (O), sulfur (S) or nitrogen (N). Heterocycles may be monocyclic or polycyclic rings. Heterocycles may be 3 to 6 membered monocyclic ring or 5 to 6 membered monocyclic ring. When heterocycle is a polycyclic ring, the rings comprise at least one ring comprising the heteroatom and the other rings may be cycloalkyl, aryl or heterocycle and the point of attachment may be on any available atom. This term includes without limitation, for example, aziridinyl, oxiranyl, thiiranyl, azirinyl, oxirenyl, thiirenyl, azetidinyl, oxetanyl, oxetyl, pyrrolidinyl, oxolanyl, thiolanyl, piperidinyl, oxanyl, thianyl, azepanyl, oxepanyl, morpholinyl, piperazinyl, homopiperazinyl.

As used herein, the expression "alkyl", "alkylene", "alkenyl", "alkenylene", "alkoxy", "aryl", "cycloalkyl", "heteroaryl", "heterocycle", "alkoxy," "alkenyloxy," and "alkynyloxy" (including lower alkyl and lower cycloalkyl) are all independently optionally substituted by one or more substituents. In the context of use in the definition of L, "alkylene" and "alkenylene" are preferably unsubstituted or substituted by one or more fluoride atoms, preferably "alkylene" and "alkenylene" are unsubstituted.

The term "optionally substituted", "optionally substituent" or "substituent" (such as for the definition of X, Ra, R2, R3, R4 and R5 herein above) represents at each occurrence and independently, one or more halogen, amino, amidino, amido, azido, cyano, guanido, hydroxyl, nitro, nitroso, urea, OS(O)₂Rm (wherein Rm is selected from C1-6alkyl, C6-10aryl or 3-10 membered heterocycle), OS(O)₂ORn (wherein Rn is selected from H, C1-6alkyl, C6-10aryl or 3-10 membered heterocycle), S(O)₂ORp (wherein Rp is selected from H, C1-6alkyl, C6-10aryl and 3-10 membered heterocycle), S(O)₀₋₂Rq (wherein Rq is selected from H, C1-6alkyl, C6-10aryl or 3-10 membered heterocycle), OP(O)ORsORt, P(O)ORsORt (wherein Rs and Rt are each independently selected from H or C1-6alkyl), C1-6alkyl, C6-10 aryl-C1-6alkyl, C6-10aryl, C1-6alkoxy, C6-10aryl- C1-6alkyloxy, C6-10aryloxy, 3-10 membered heterocycle, C(O)Ru (wherein Ru is selected from H, C1-6alkyl, C6-10aryl, C6-10aryl-C1-6alkyl or 3-10 membered heterocycle), C(O)ORv (wherein Rv is selected from H, C1-6alkyl, C6-10aryl, C6-10aryl-C1-6alkyl or 3-10 membered heterocycle), NRxC(O)Rw (wherein Rx is H or C1-6alkyl and Rw is selected from H, C1-6alkyl, C6-10aryl, C6-10aryl-C1-6alkyl or 3-10 membered heterocycle, or Rx and Rw are taken together with the atoms to which they are attached to form a 3 to 10 membered heterocycle) or SO2NRyRz (wherein Ry and Rz are each independently selected from H, C1-6alkyl, C6-10aryl, C3-10heterocycle or C6-10aryl-C1-6alkyl).

In another embodiment, the term "optionally substituted", "optionally substituent" or "substituent" preferably represents halogen, C1-6alkyl, C2-6alkenyl, C2-6alkynyl, C1-6 alkoxy, C2-6alkenyloxy, C2-6 alkynyloxy, —NR40R41, —C(O)NR40R41, —NR40COR41, carboxy, azido, cyano, hydroxyl, nitro, nitroso, —OR40, —SR40, —S(O)$_{0-2}$R40, —C(O)R40, —C(O)OR40 or —SO$_2$NR40R41; wherein R40 and R41 are each independently H, C1-6alkyl, C2-6alkenyl or C2-6alkynyl.

In still another embodiment, the term "optionally substituted", "optionally substituent" or "substituent" preferably represents halogen, C1-6alkyl, C2-6alkenyl, C1-6 alkoxy, —NR40R41, —C(O)NR40R41, —NR40COR41, carboxy, hydroxyl, nitro, —SR40, —S(O)$_{0-2}$R40, —C(O)R40, —C(O)OR40 or —SO$_2$NR40R41; wherein R40 and R41 are each independently H, or C1-6alkyl.

The term "independently" means that a substituent can be the same or a different definition for each item.

The expression "protecting group" includes any suitable protecting groups for protecting the indicated moiety. Examples of "protecting group" for protecting hydroxyl moiety include but are not limited to benzyl, substituted benzyl such as para-methoxybenzyl (PMB), or other standard hydroxyl protecting groups, to the extent that the group is compatible with the relevant chemical transformation. More examples of protecting groups can be found in Green et al., "Protective Groups in Organic Chemistry", (Wiley, 4$^{th}$ ed. 2007) and Harrison et al. "Compendium of Synthetic Organic Methods" (John Wiley and Sons, 1996).

The compounds as defined herein may include a chiral center which gives rise to enantiomers. The compounds may thus exist in the form of two different optical isomers, that is (+) or (−) enantiomers. Chiral centers in the compounds described herein may be designated as (R) or (S), in accordance with established nomenclature criteria. Each individual enantiomers as well as enantiomer mixtures thereof, including racemic or any ratio mixtures of individual enantiomers, are included within the scope of the invention. The single enantiomer can be obtained by methods well known to those of ordinary skill in the art, including chiral synthesis or other separation/purification methods such as chiral HPLC, enzymatic resolution and chiral auxiliary derivatization.

It will also be appreciated that the compounds in accordance with the present disclosure can contain more than one chiral centre. The compounds of the present disclosure may thus exist in the form of different diastereomers. All such diastereomers and mixtures thereof are included within the scope of the invention. The single diastereomer can be obtained by methods well known in the art, such as HPLC, crystallization and chromatography.

There is also provided pharmaceutically acceptable salts of the compounds of the present disclosure. What is meant by the term pharmaceutically acceptable salts of the compounds is that they are derived from pharmaceutically acceptable inorganic and organic acids and bases.

For example, conventional non-toxic salts include those derived from inorganic acids such as hydrochloric, hydrobromic, sulfuric, sulfamic, phosphoric, nitric, perchloric and the like, as well as salts prepared from organic acids such as formic, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, benzenesulphonic, naphthalene 2 sulphonic, ethane disulfonic, oxalic, isethionic, trifluoroacetic and the like.

Other acids, while not in themselves pharmaceutically acceptable, may be useful as intermediates in obtaining the compounds of the disclosure and their pharmaceutically acceptable acid addition salts. Salts derived from appropriate bases include alkali metal, alkaline earth metal or ammonium salts. The salt(s) must be "acceptable" in the sense of not being deleterious to the patient thereof.

The pharmaceutically acceptable salts of the compounds of this disclosure can be synthesized from the compounds of this disclosure which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The term "solvate" means that a compound as defined herein incorporates one or more pharmaceutically acceptable solvents including water to give rise to hydrates. The solvate may contain one or more molecules of solvent per molecule of compound or may contain one or more molecules of compound per molecule of solvent. Illustrative non-limiting examples of hydrates include monohydrate, dihydrate, trihydrate and tetrahydrate or semi-hydrate. In one embodiment, the solvent may be held in the crystal in various ways and thus, the solvent molecule may occupy lattice positions in the crystal, or they may form bonds with salts of the compounds as described herein. The solvate(s) must be "acceptable" in the sense of not being deleterious to the recipient thereof. The solvation may be assessed by methods known in the art such as Loss on Drying techniques (LOD).

It will be appreciated by those skilled in the art that the compounds in accordance with the present disclosure can exist in several different crystalline forms due to a different arrangement of molecules in the crystal lattice. This may include solvate or hydrate (also known as pseudopolymorphs) and amorphous forms. All such crystalline forms and polymorphs are included within the scope of the disclosure. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC) differential thermal analysis (DTA), thermogravimetric analysis (TGA)), Raman spectroscopy, comparative intrinsic dissolution rate, scanning electron microscopy (SEM).

When there is a sulfur atom present, the sulfur atom can be at different oxidation levels, ie. S, SO, or SO$_2$. All such oxidation levels are within the scope of the present disclosure. When there is a nitrogen atom present, the nitrogen atom can be at different oxidation levels, ie. N or NO. All such oxidation levels are within the scope of the present disclosure.

Some of the compounds described herein contain one or more double bonds, and unless specified otherwise, are meant to include both E and Z geometric isomers in any proportion.

In one aspect, there is provided a compound of formula ii

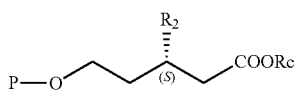

ii wherein P is a protecting group, R2 is as defined previously and Rc is a lower straight or branched alkyl or lower cycloalkyl. Preferably, P is a hydrogen labile protecting group. Preferably, R2 is methyl, Rc is methyl and P is a benzyl (CH2-Ph) group.

In one aspect, there is provided a compound of formula iii

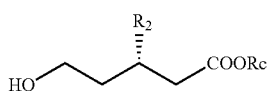

iii wherein R2 and Rc are as defined previously.

In one aspect, there is provided a compound of formula iv

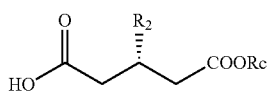

iv wherein $R_2$ and Rc are as defined previously.

Previous syntheses of compound ii commenced with the stereoselective hydrolysis of a symmetrical dimethyl ester of glutaric acid using pig liver esterase (PLE) to obtain the chiral synthon which gave unsatisfactory enantiomeric ratio for the purpose of industrial applications (such as ratio of R/S:90/10). Furthermore, this procedure is not well suited for the larger scale synthesis. Other synthesis of the chiral compound ii have also been reported, using 3-methyl glutaric anhydride as a starting material.

In one aspect, there is provided a process for preparing a compound of formula ii:

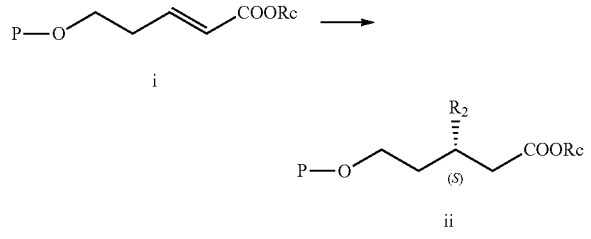

comprising an enantioselective conjugate addition of $R_2$—MgBr to the α,β-unsaturated ester compound i. Preferably, the (S|R) ratio in compound ii is at least 90/10, preferably higher than about 95/5, more preferably higher than about 97/3 or more preferably about 98/2.

Preferably, the enantioselective conjugate addition is conducted using a chiral (S) BINAP reagent, such as (S)-Tol-BINAP and a suitable Cu(I) salt such as CuBr. Preferably $R_2$—MgBr is Me-MgBr. Preferably, the reaction is conducted at low temperature, such as about −20° C. When (S)-Tol-BINAP is used, the amount is preferably less than 6 mol % and more preferably about 4.5 mol %. When CuBr is used, the amount is preferably less than about 3 mol %, and more preferably less than about 2.5 mol %. When Me-MgBr is used, the amount is about 3 equivalent, (such as 3.2 equivalent).

The following table is representative of results obtained for the above enantioselective conjugate addition:

| (S)-Tol-BINAP | CuX | MeMgBr | Temperature | S/R | Yield ** |
|---|---|---|---|---|---|
| 4.5 mol % | (X=Br) 2.5 mol % | 3.2 equiv. | −20° C. | 97.5/2.5 | 50% |
| 4.5 mol % | (X=Br) 2 mol % | 3.2 equiv. | −20° C. | 98.4/1.6 | 50% |

*S/R ratio was calculated using chiral HPLC by comparison with the racemic compound.

** Isolated yield.

Under the prefered conditions, the reaction allows to obtain an enantioselectivity of 98-99%.

In one aspect, there is provided a process for preparing a compound of this disclosure in accordance with the following steps:

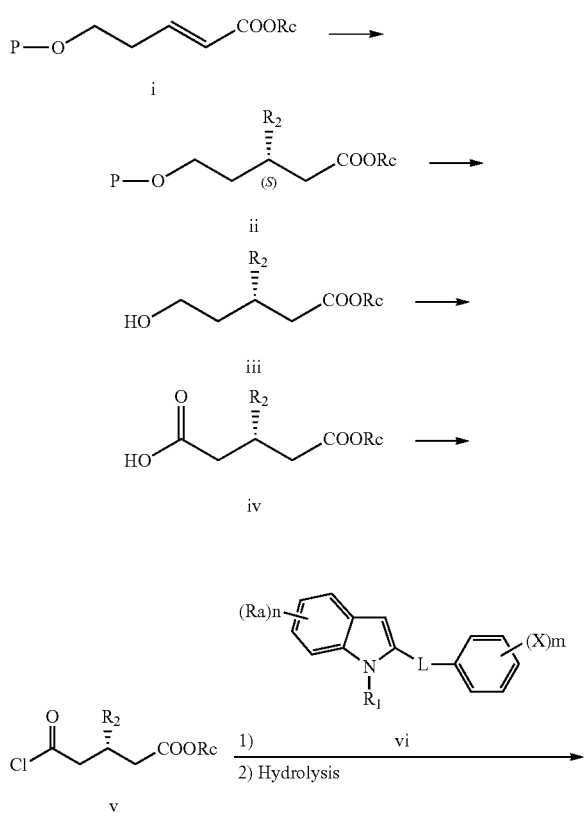

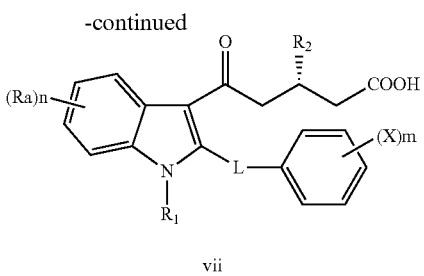

vii

In one embodiment, the steps comprise preparing compound ii as described above; deprotecting group P; oxydizing oxidizing the primary —OH group of compound iii to provide compound iv; converting compound iv to acyl chloride v; effecting a Friedel-crafts acylation of an indole derivative vi with acyl chloride v; and hydrolyzing the ester —COORc to provide said compound vii.

In one embodiment, the protecting group P is a hydrogen-labile group, such as a benzyl derivative, and the deprotection conditions can conveniently be $H_2$ and a suitable catalyst, such as Pd/C in a suitable solvent such as EtOAc:EtOH. Compound iii can be oxidized using standard and known oxidation methods of primary alcohol, provided that the method is compatible with the other functional groups. Suitable oxidation conditions may be PDC oxidation. Compound iv may be converted using standard acyl chloride forming conditions compatible with the other functional groups, such as $(COCl)_2$ and a catalytic amount of DMF. The Friedel-crafts acylation of compound vi requires a suitable lewis acid, an example of which is $Me_2AlCl$. The ester —COORc hydrolysis may conveniently be effected using $BBr_3$.

As defined herein "subject" refers to both human and non-human subjects. Preferably the subject is human. Although not limited to such subject (or patient), the compound, composition, combination or method as defined herein are expected to be particularly useful to the treatment of patients who have suffered a previous episode associated with diseases described herein, or are otherwise considered to be at increased risk of said diseases.

As used herein, "treatment" or "treating" refers to at least controlling or ameliorating at least one disease described herein, at least for the duration of said treatment.

As used herein, "prevention" or "prophylaxis" treatment (which may be used interchangeably) is understood to mean that the occurrence of at least one disease described herein, is prevented, at least for the duration of said treatment. A preventive treatment would preferably i) reduce the occurrences of a further episode, ii) reduce its severity or iii) prevent occurrences of further episodes, at least for the duration of the therapy.

In another embodiment, the present disclosure provides a combination comprising a therapeutically effective amount of a compound, as defined herein, and a therapeutically effective amount of one or more therapeutic agents useful in the method of the present disclosure.

The second therapeutic agent may be, for example, an agent having analgesic, anti-inflammatory and/or anti-allergic properties. Non-limiting examples of second agents contemplated for use in the methods of the invention include: cyclooxygenase inhibitors, non-steroidal anti-inflammatory drugs (NSAIDs) and peripheral analgesic agents. Compounds and pharmaceutical compositions comprising the compounds of the invention may also be used in combination with leukotriene modifiers, e.g. inhibitors of the biosynthesis of the leukotrienes, such as zileuton (Zyflo®), and leukotriene antagonists such as montelukast (Singulair®) and zafirlukast (Accolate®). Other types of agents which may be useful in combination with the compounds of the present invention include anti-cholinergics, bronchodilators, corticosteroids, beta-2 agonists and other anti-asthmatic drugs such as calcium antagonists. The second therapeutic agent is preferably glucocorticoids, cysLT1 antagonists and beta-2 agonists.

In the context of asthma, nonselective NSAIDs would probably not be desirable, however, they may be useful in other non-allergic diseases. Selective COX-2 inhibitors are tolerated by asthmatics who are sensitive to nonselective NSAIDs and as such may therefore be useful. Examples of NSAIDs which may be co-administered include, but are not limited to: acetyl salicylic acid, amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, diclofenac, difisalamine, difenpyramide, emorfazone, enfenamic acid, enolioam, epirizole, etersalate, etodolac, etofenamate, fanetizole mesylate, fenclorac, fenbufen, fenoprofen, flurbiprofen, fendosal, fenflumizole, feprazone, floctafenine, flunixin, flunoxaprofen, fluproquazone, fopirtoline, fosfosal, furcloprofen, glucametacin, guaimesal, ibuprofen, ibuproxam, indomethacin, isofezolac, isonixim, isoprofen, isoxicam, ketoprofen, lefetamine HCl, leflunomide, lofemizole, lonazolac calcium, lotifazole, loxoprofen, lysin clonixinate, meclofenamate sodium, meseclazone, nabumetone, nictindole, nimesulide, naproxen, phenylbutazone, piroxicam, sulindac, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolmetin, tolpadol, tryptamid and ufenamate.

It will be clear to a person of ordinary skill that the amounts and/or ratios of therapeutic agents will be readily adjusted. It will be understood that the scope of combinations described herein is not particularly limited, but includes in principle any therapeutic agent useful for preventing or treating the diseases described herein.

It will also be appreciated that the amounts and/or ratios of therapeutic agents for use in treatment will vary not only with the particular agent selected but also with the route of administration, the nature of the condition for which treatment is required and the age and condition of the patient and will be ultimately at the discretion of the attendant physician.

The compounds defined herein can be administered concurrently to the one or more agents used herein in the methods and combinations. The desired doses may conveniently be presented in a single dose or as divided dose administered at appropriate intervals, for example as two, three, four or more doses per day or continuously such as in a perfusion. The compound can be administered on a dosage regimen distinct to the one or more agents used herein in the methods and combinations. Alternatively, the compound can be administered sequentially or concurrently in distinct formulations or in a common formulation.

Pharmaceutical compositions may comprise pharmaceutically acceptable carrier(s) and/or excipient(s). Many pharmaceutically acceptable carrier(s) and/or excipient(s) are known in the art. It will be understood by those in the art that a pharmaceutically acceptable carrier must be compatible with the other ingredients of the formulation and tolerated by a subject in need thereof. or liquid preparations, such as oral or sterile parenteral solutions or suspensions. The proportion of each carrier is determined by the solubility and chemical nature of the agent(s), the route of administration, and standard pharmaceutical practice.

In order to ensure consistency of administration, in an embodiment of the present disclosure, the pharmaceutical composition is in the form of a discrete dosage units and may be prepared by any of the methods well known in the art of pharmacy. All methods include the step of bringing into association the active compound with a liquid carrier or solid carrier or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations according to the disclosure may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Metabolites of arachidonic acid such as 5-oxo-ETE and other eicosanoids are potent chemoattractants for eosinophils and neutrophils both in vitro and in vivo, and stimulate a variety of responses in these cells, such as actin polymerization, calcium mobilization, integrin expression and degranulation (Powell and Rokach, Progress in *Lipid Research* 52: 651-665 (2013). Through their effects on both cell migration and survival, eicosanoids such as 5-oxo-ETE are involved in the pathogenesis of diseases involving eosinophils, including asthma and other inflammatory diseases.

Accordingly the compounds, combinations and compositions provided herein are useful for the treatment or prevention of diseases or conditions involving 5-oxo-ETE.

Accordingly there is provided compounds, combinations, compositions and methods as defined herein that may provide treatment or prevention of eosinophilic and inflammatory conditions.

There are many diseases or conditions that are inflammatory in their nature. For example, inflammatory diseases that affect the population include asthma, allergic rhinitis, chronic obstructive pulmonary disease, idiopathic pulmonary fibrosis, and rhinitis. Inflammation is also a common cause of pain. Inflammatory pain may arise for numerous reasons, such as infection, surgery or other trauma.

The term "inflammation" will be understood by those skilled in the art to include any condition characterised by a localised or a systemic protective response, which may be elicited by physical trauma, infection, chronic diseases, such as those mentioned hereinbefore, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white blood cells, loss of function and/or any other symptoms known to be associated with inflammatory conditions. The term "inflammation" will thus also be understood to include any inflammatory disease, disorder or condition per se, any condition that has an inflammatory component associated with it, and/or any condition characterised by inflammation as a symptom, insofar as it is related to a respiratory disease or condition, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

In an aspect, there is provided compounds, combinations, compositions and methods as defined herein that may provide treatment or prevention of respiratory disease or condition such as asthma, chronic obstructive pulmonary disease, pulmonary fibrosis, allergic rhinitis, rhinitis, and any other respiratory disease or condition with an inflammatory component, characterized by inflammation or characterized by eosinophilia.

In one embodiment, there is provided compounds, combinations, compositions and methods as defined herein that may provide treatment or prevention of asthma, which method comprises administration of a compound or composition of the disclosure to a subject.

Asthma is a common chronic disorder of the airways that is complex and characterized by variable and recurring symptoms including airflow obstruction, bronchoconstriction and an underlying inflammation. Treatment regimens for asthma vary depending on the severity of the condition. As used herein, the term "asthma" includes all types of asthma, including without limitation: mild, moderate and severe asthma; exercise-induced asthma; aspirin-induced asthma; extrinsic or allergic asthma; intrinsic or non-allergic asthma; occupational asthma; cough-variant asthma; nocturnal asthma; child-onset asthma; and adult-onset asthma.

In one embodiment, there is provided compounds, combinations, compositions and methods as defined herein that may provide treatment or prevention of chronic obstructive pulmonary disease (COPD). COPD refers to a group of diseases of the lungs in which the airways become narrowed, typically due to an abnormal inflammatory response in the lungs. Non-limiting examples of COPD include bronchitis and emphysema. Idiopathic pulmonary fibrosis (IPF) is another lung disease also involving eicosanoids.

In one embodiment, there is provided compounds, combinations, compositions and methods as defined herein that may provide treatment or prevention of allergic rhinitis. Allergic rhinitis is an inflammation of the nasal passages, usually associated with watery nasal discharge and itching of the nose and eyes. Allergies occur when the immune system overreacts to particles in the air and produces an allergic reaction.

In accordance with another aspect, there is provided compounds, combinations, compositions and methods as defined herein that may provide treatment or prevention of a disease or condition involving eicosanoids such as 5-oxo-ETE and 5-HETE.

In accordance with another aspect, there is provided compounds, combinations, compositions and methods as defined herein that may be useful for inhibiting the effect of eicosanoids such as 5-oxo-ETE and 5-HETE and 5-oxo-15-HETE.

In accordance with another aspect, there is provided compounds, combinations, compositions and methods as defined herein that may be useful for antagonizing the 5-oxo-ETE receptors, such as the OXE receptor.

It should be understood that, in addition to blocking biological responses to 5-oxo-ETE, 5-oxo-15-HETE and 5-HETE, the compounds and compositions of the invention may block biological responses to other related eicosanoids which can also act as ligands for the OXE receptor. Thus "eicosanoid", as used herein, means a substance derived from a fatty acid having 20 carbon atoms, such as eicosanoic acid, and in an aspect, a fatty acid in which the 8th position is unsaturated. Non-limiting examples of eicosanoids which are encompassed in the methods presented herein include 5-oxo-ETE, 5-HETE, 5-HPETE, arachidonic acid, 5-oxo-ETrE (5-oxo-6E,8Z,11Z-eicosatrienoic acid), 5-HETrE (5-hydroxy-6E,8Z,11Z-eicosatrienoic acid), eicosa-5Z, 8Z, 11Z-trienoic acid, 5-oxo-EDE (5-oxo-6E,8Z-eicosadienoic acid), and eicosa-5Z,8Z-dienoic acid. In addition, certain 18-carbon polyunsaturated fatty acids are included, e.g. 5-oxo-ODE (5-oxo-6E,8Z-octadecadienoic acid), 5-HODE (5-hydroxy-6E,8Z-octadecadienoic acid), and sebaleic acid (5Z,8Z-octadecadienoic acid).

As mentioned above, eicosanoids acting through the OXE receptor elicit migration of eosinophils and neutrophils. There is therefore provided compounds, combinations, compositions and methods as defined herein that may provide inhibition of migration of eosinophils and neutrophils. As such, treatment or prevention of disease states that may be alleviated by inhibition of eosinophil or neutrophil migration is also encompassed.

It has been shown that 5-oxo-ETE can stimulate proliferation of prostate tumor cells and the OXE receptor is expressed on prostate tumor cells. Metabolites of arachidonic acid including HETEs and oxo-ETEs have been shown to increase growth and promote survival of a variety of cancers, including lung, pancreatic and prostate cancer. Moreover 5-hydroxyeicosatetraenoids are the principal arachidonic acid metabolite in prostate cancer cells (see e.g. WO 2007/025254 and US 2005/0106603 for review of the role of G-protein coupled eicosanoid receptors in cancer). These findings indicate a potential role for the 5-oxo-ETE receptor antagonists of the compounds defined herein in treatment or prevention of certain cancers, as well as induction of apoptosis in these cancer cells. Thus in an embodiment, there is provided compounds, combinations, compositions and methods as defined herein that may be useful in the treatment or prevention of cancer, including lung, pancreatic and/or prostate cancer. In an aspect, there is provided herein a method that may be useful for the treatment or prevention of lung, pancreatic and/or prostate cancer. In another aspect, there is provided a method that may be useful for inducing apoptosis in a cancer cell, e.g. a lung, pancreatic and/or prostate cancer cells.

In an aspect, there is provided compounds, combinations, compositions and methods as defined herein that may be useful in the treatment or prevention of viral infections (e.g. influenza, common cold).

In an aspect, there is provided compounds, combinations, compositions and methods as defined herein for that may be useful in the treatment or prevention of atopic dermatitis, psoriasis and/or acne.

5-LO products have been considered a factor in the development of tissue inflammation. Synthesis of leukotrienes and 5 oxo-ETE is controlled by the enzyme 5-lipoxygenase.

The pharmacologic role of 5-LO products has been investigated in psoriasis. It has been suggested that the inhibition of 5-LO products may be useful in the treatment of psoriasis.

Tissue inflammation is a component of the acne process. Therefore, inhibitors of 5-lipoxygenase products may be useful compounds in the treatment of acne vulgaris.

Atopic dermatitis is a chronic, relapsing skin condition. The pathophysiology is believed to involve the release of inflammatory mediators. 5-LO products are believed to play a role in inflammatory and atopic conditions. Modulators of 5-LO products may therefore be useful in the treatment of atopic dermatitis.

The following examples are provided to further illustrate details for the preparation and use of the compounds of the present disclosure. They are not intended to be limitations on the scope of the instant disclosure in any way, and they should not be so construed. Furthermore, the compounds described in the following examples are not to be construed as forming the only genus that is considered as the disclosure, and any combination of the compounds or their moieties may itself form a genus.

EXAMPLES

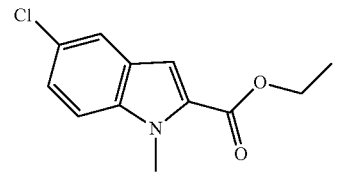 [SMILES: CCOC(=O)c1cc2cc(Cl)ccc2n1C]

Synthesis of ethyl
5-chloro-1-methyl-1H-indole-2-carboxylate (2)

To a stirred solution of ethyl 5-chloro-1H-indole-2-carboxylate (1 g, 4.48 mmol) in DMF (10 ml) was added NaH (0.215 g, 5.4 mmol, 60% dispersion in mineral oil) at 0° C., and stirred for 30 min followed by the addition of MeI (0.764 mg, 5.4 mmol). After stirred at room temperature for about 20 min, the reaction mixture was quenched with 4 N HCl at 0° C. and extracted with $Et_2O$ for four times. The organic layers were combined, washes with brine, and dried over $Na_2SO_4$. The solvent were evaporated under reduced pressure and the crude was purified using silica gel chromatography (10% EtOAc/hexane) to afford ethyl 5-chloro-1H-indole-2-carboxylate (1 g, 94%). $^1H$ NMR (400 MHz, $CDCl_3$): δ 7.64 (s, 1H), 7.30 (d, 2H), 7.22 (s, 1H), 4.38 (q, 2H), 4.06 (s, 3H), 1.41 (t, 3H). $^{13}C$ NMR: 161.95, 137.92, 129.20, 126.66, 126.19, 125.35, 121.62, 111.39, 109.30, 60.75, 31.84, 14.35.

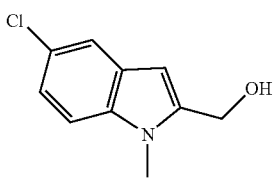

Synthesis of (5-chloro-1-methyl-1H-indol-2-yl) methanol (3)

To a stirred solution of ethyl 5-chloro-1H-indole-2-carboxylate (100 mg, 0.48 mmol) in THF (1 ml) was added LiAlH$_4$ (47.1 mg, 1.24 mmol) slowly at −20° C. Once the addition was complete the reaction mixture was allowed to warm to rt and stirred for 4 h. Water was added and the organic layer was dried over Na$_2$SO$_4$. The solvents were evaporated under reduced pressure to get the crude product (89 mg), which was used without any further purification. $^1$H NMR (400 MHz, CDCl$_3$): δ 7.54 (s, 1H), 7.23 (d, 1H), 7.19-7.14 (m, 1H), 6.40 (s, 1H), 4.79 (s, 2H), 3.80 (s, 3H). $^{13}$C NMR: 140.22, 136.85, 128.40, 125.53, 122.59, 120.45, 110.50, 101.28, 57.76, 30.35.

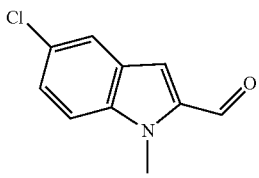

Synthesis of 5-chloro-1-methyl-1H-indole-2-carbaldehyde (4)

To a stirred solution of crude (5-chloro-1-methyl-1H-indol-2-yl)methanol (17.55 g, 89.7 mmol) in dichloromethane (150 mL) was added activated MnO$_2$ (86.94 g, 897 mmol) and stirred at rt for 30 h. The reaction mixture was filtered through celite. The solvents were evaporated under reduced pressure to afford 5-chloro-1-methyl-1H-indole-2-carbaldehyde as a solid (17.5 g, 97%). HRMS (ESI) m/z calcd for [C$_{10}$H$_8$ClNO]$^+$: 194.0367 found 194.0255. $^1$H NMR (400 MHz, CDCl$_3$): δ 9.89 (s, 1H), 7.70 (s, 1H), 7.35 (q, 2H), 7.18 (s, 1H), 4.08 (s, 3H). $^{13}$C NMR: 182.88, 139.03, 136.43, 127.28, 126.97, 126.61, 122.33, 116.25, 111.58, 31.73.

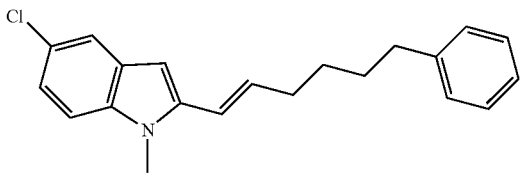 [SMILES: Cn1c(/C=C/CCCCc2ccccc2)cc2cc(Cl)ccc21]

Synthesis of 5-chloro-1-methyl-2-(6-phenylhex-1-en-1-yl)-1H-indole (6, n=4, R=H)

To a suspension of triphenyl(5-phenylpentyl)phosphonium bromide (1.6 g, 3.2 mmol) in THF (40 mL) was added LiHMDS (1.0 M in THF, 3.1 mL, 3.1 mmol) at −78° C. The mixture was stirred for 30 min, cooled back to −78° C., and 5-chloro-1-methyl-1H-indole-2-carbaldehyde (0.47 g, 2.4 mmol) in THF (15 ml) was added dropwise. The reaction mixture was allowed to warm to rt and stirred for 3 h. Saturated NH$_4$Cl solution was added, and the organic layer was extracted with EtOAc. The combined organic layers were washed with brine, dried over Na$_2$SO$_4$ and the solvents were evaporated under reduced pressure. The crude was purified by silica gel chromatography (10% EtOAc/Hexane) to afford 32 as a white solid (0.723 g, 93%). $^1$H NMR (400 MHz, CDCl$_3$): δ 7.48 (d, 1H), 7.31-7.26 (m, 2H), 7.17 (dd, 4H), 7.09 (d, 1H), 6.48 (s, 1H), 6.34 (m, 2H), 3.68 (s, 3H), 2.70-2.62 (m, 2H), 2.32-2.27 (m, 2H), 1.70 (dt, 2H), 1.61-1.49 (m, 2H). $^{13}$C NMR: 142.47, 140.02, 135.26, 135.18, 128.89, 128.41, 128.31, 125.72, 125.23, 121.27, 119.30, 118.56, 109.95, 97.32, 35.80, 33.29, 31.02, 29.95, 28.77.

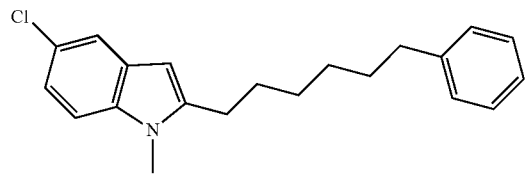 [SMILES: Cn1c(CCCCCCc2ccccc2)cc2cc(Cl)ccc21]

Synthesis of 5-chloro-1-methyl-2-(6-phenylhexyl)-1H-indole (9, n=4, R=H)

To a stirred solution of (E)-5-chloro-1-methyl-2-(6-phenylhex-1-en-1-yl)-1H-indole (0.651 g, 2.0 mmol) in EtOH (6 mL) was added 10% Pd/C (65 mg) under H$_2$ atm. The reaction mixture was stirred at rt for 3 h and then filtered. The residue was washed with EtOAc, and the combined filtrate was concentrated under reduced pressure to afford 5-chloro-1-methyl-2-(6-phenylhexyl)-1H-indole as a white solid (0.611 g, 94%). HRMS (ESI) m/z calcd for [C$_{21}$H$_{24}$ClNO]$^+$: 326.1676 found 326.1843. $^1$H NMR (400 MHz, CDCl$_3$): δ 7.47 (s, 1H), 7.28 (d, 1H), 7.21-7.13 (m, 5H), 7.08 (dd, 1H), 6.17 (s, 1H), 3.63 (s, 3H), 2.72-2.65 (m, 2H), 2.61 (t, 2H), 1.80-1.60 (m, 4H), 1.44 (dd, 4H).

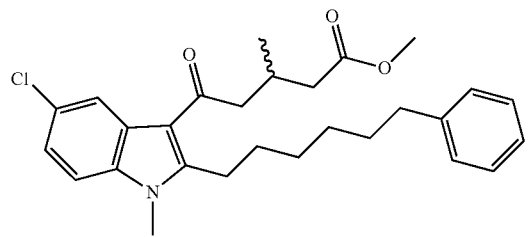 [SMILES: COC(=O)CC(C)CC(=O)c1c(CCCCCCc2ccccc2)n(C)c2ccc(Cl)cc12]

Synthesis of methyl 5-(5-chloro-1-methyl-2-(6-phenylhexyl)-1H-indol-3-yl)-3-methyl-5-oxopentanoate (11, n=4, R=H)

To a stirred solution of 5-methoxy-3-methyl-5-oxopentanoic acid (1.24 g, 7.75 mmol) in dichloromethane (10 ml) was added one drop of DMF followed by 7.8 ml of oxalyl chloride solution (2.0 M in dichloromethane, 15.6 mmol) at 0° C. The reaction mixture was stirred for 4 h in rt and the crude was evaporated under reduced pressure to obtain methyl 5-chloro-3-methyl-5-oxopentanoate. To a stirred solution of 5-chloro-1-methyl-2-(6-phenylhexyl)-1H-indole (2 g, 6.14 mmol) in dichloromethane was added Me₂AlCl (1.0 M in hexane, 12.3 mL, 12.3 mmol) at 0° C. After 45 min, 5-chloro-3-methyl-5-oxopentanoate (1.31 g, 7.36 mmol) in CH₂Cl₂ (10 mL) was added dropwise at rt and the reaction mixture stirred for 1 h. The reaction was quenched by adding water and extracted with EtOAc. The organic layers were combined, washed with brine and dried over Na₂SO₄. The solvents were evaporated under reduced pressure and the crude was purified by silica gel chromatography using 20% EtOAc/Hex as eluent to afford 5-(5-chloro-1-methyl-2-(6-phenylhexyl)-1H-indol-3-yl)-3-methyl-5-oxopentanoate (2.6 g, 90%). ¹H NMR (400 MHz, CDCl₃): δ 7.89 (d, 1H), 7.30-7.21 (m, 4H), 7.21-7.13 (m, 3H), 3.69 (s, 3H), 3.68 (s, 3H), 3.20-3.12 (m, 2H), 3.02 (dd, 1H), 2.89 (dd, 1H), 2.75 (dd, 1H), 2.60 (t, 2H), 2.52 (dd, 1H), 2.32 (dd, 1H), 1.69-1.58 (m, 4H), 1.53-1.34 (m, 4H), 1.09 (d, 3H). ¹³C NMR: 194.91, 173.17, 150.63, 142.69, 135.10, 128.39 (s), 128.24, 127.83, 126.92, 125.62, 122.17, 120.43, 113.23, 110.59, 51.46, 49.37, 41.12, 35.92, 31.39, 29.66 (s), 29.61, 29.08, 29.05, 26.50, 26.28, 20.35.

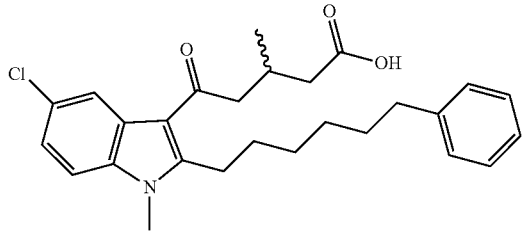 [SMILES: CC(CC(=O)O)CC(=O)c1c(CCCCCCc2ccccc2)n(C)c2ccc(Cl)cc12]

Synthesis of 5-(5-chloro-1-methyl-2-(6-phenyl-hexyl)-1H-indol-3-yl)-3-methyl-5-oxopentanoic acid (15)

To a stirred solution of 5-(5-chloro-1-methyl-2-(6-phenylhexyl)-1H-indol-3-yl)-3-methyl-5-oxopentanoate (1.14 g, 2.44 mmol) in THF/H₂O (4/1, 10 ml) was added LiOH (1.02 g, 24.4 mmol). The reaction mixture was stirred for 48 h in rt and the THF was evaporated under reduced pressure. The aqueous layer was acidified with 4 N HCl and then extracted with EtOAc, the organic layers were combined, washed with brine and dried over Na₂SO₄. The solvents were evaporated under reduced pressure to afford 5-(5-chloro-1-methyl-2-(6-phenylhexyl)-1H-indol-3-yl)-3-methyl-5-oxopentanoic acid (1.05 g, 95%). HRMS (ESI) m/z calcd for [C₂₇H₃₂ClNO₃+H]⁺: 454.2143, found 454.2357. ¹H NMR (400 MHz, CDCl₃): δ 7.88 (d, J=0.9 Hz, 1H), 7.26-7.21 (m, 4H), 7.08 (d, J=8.2 Hz, 2H), 3.69 (s, 3H), 3.16 (t, J=7.7 Hz, 2H), 3.05-2.93 (m, 2H), 2.76-2.68 (m, 1H), 2.62-2.53 (m, 3H), 2.36 (dd, J=15.2, 7.3 Hz, 1H), 1.64-1.56 (m, 4H), 1.51-1.43 (m, 2H), 1.41-1.33 (m, 2H), 1.13 (d, J=6.7 Hz, 3H). ¹³C NMR: 195.37, 176.70, 151.09, 141.08, 135.16, 131.30, 129.74, 128.33, 128.05, 126.90, 122.35, 120.39, 113.07, 110.70, 49.06, 40.90, 35.22, 31.23, 29.66, 29.59, 28.97, 28.91, 26.53, 26.32, 20.50.

Compounds 12-14 and 17-25 were prepared in a similar manner as for compound 15 above and had the following characterization:

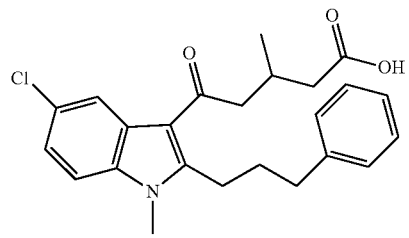 [SMILES: CC(CC(=O)O)CC(=O)c1c(CCCc2ccccc2)n(C)c2ccc(Cl)cc12]

5-(5-chloro-1-methyl-2-(3-phenylpropyl)-1H-indol-3-yl)-3-methyl-5-oxopentanoic acid (12)

¹H NMR (400 MHz, CDCl₃): δ 7.89 (s, 1H), 7.36 (s, 1H), 7.29 (t, 2H), 7.20 (t, 5H), 3.56 (s, 3H), 3.25-3.13 (m, 2H), 2.97 (qd, 2H), 2.79 (q, 2H), 2.71 (dt, 1H), 2.45 (ddd, 2H), 2.02-1.89 (m, 2H), 1.14 (d, 3H). ¹³C NMR: 178.10, 172.09, 142.89, 142.21, 136.50, 129.35, 128.41, 128.33, 128.26, 125.79, 123.46, 120.73, 115.23, 107.98, 44.92, 40.33, 35.71, 31.06, 30.45, 28.41, 27.17, 20.06.

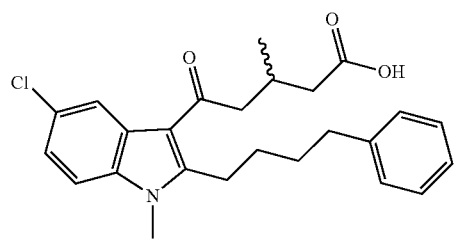 [SMILES: CC(CC(=O)O)CC(=O)c1c(CCCCc2ccccc2)n(C)c2ccc(Cl)cc12]

methyl 5-(5-chloro-1-methyl-2-(4-phenylbutyl)-1H-indol-3-yl)-3-methyl-5-oxopentanoic acid (13): ¹H NMR (400 MHz, CDCl₃)

δ 7.88 (s, 1H), 7.25 (m, 5H), 7.17 (m, 3H), 3.65 (s, 3H), 3.25-3.15 (m, 2H), 3.07-2.91 (m, 2H), 2.70 (dt, J=15.0, 7.1 Hz, 3H), 2.55 (dd, J=15.2, 5.4 Hz, 1H), 2.34 (dd, J=15.2, 7.3 Hz, 1H), 1.80 (dt, J=15.0, 7.6 Hz, 2H), 1.71-1.59 (m, 2H), 1.13 (d, J=6.6 Hz, 3H). ¹³C NMR: 195.16, 178.25, 150.70, 142.06, 135.11, 128.40, 128.31, 127.96, 126.87, 125.78, 122.28, 120.38, 113.15, 110.66, 49.10, 40.95, 35.56, 31.28, 29.61, 28.53, 26.38, 26.15, 20.37.

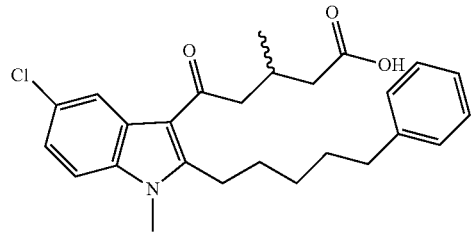 [SMILES: CC(CC(=O)O)CC(=O)c1c(CCCCCc2ccccc2)n(C)c2ccc(Cl)cc12]

5-(5-chloro-1-methyl-2-(5-phenylpentyl)-1H-indol-3-yl)-3-methyl-5-oxopentanoic acid (14)

¹H NMR (400 MHz, CDCl₃): δ 7.89 (s, 1H), 7.25 (m, Hz, 4H), 7.17 (dd, J=12.1, 6.4 Hz, 3H), 3.68 (s, 3H), 3.23-3.12 (m, 2H), 2.99 (qd, J=16.1, 6.9 Hz, 2H), 2.82-2.68 (m, 1H), 2.66-2.52 (m, 3H), 2.35 (dd, J=15.2, 7.4 Hz, 1H), 1.73-1.60 (m, 4H), 1.51 (dd, J=14.2, 7.3 Hz, 2H), 1.14 (d, J=6.7 Hz, 3H). ¹³C NMR: 195.12, 178.28, 150.86, 142.49, 135.11, 128.45, 128.27, 127.95, 126.90, 125.68, 122.26, 120.40, 113.11, 110.65, 49.09, 40.96, 35.82, 31.24, 29.61, 29.37, 28.91, 26.41, 26.26, 20.37.

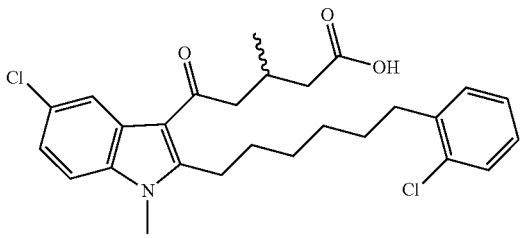 [SMILES: CC(CC(=O)O)CC(=O)c1c(CCCCCCc2ccccc2Cl)n(C)c2ccc(Cl)cc12]

5-(5-chloro-2-(6-(2-chlorophenyl)hexyl)-1-methyl-1H-indol-3-yl)-3-methyl-5-oxopentanoic acid (17)

¹H NMR (400 MHz, CDCl₃): δ 7.89 (s, 1H), 7.31 (d, 1H), 7.25-7.06 (m, 5H), 3.70 (s, 3H), 3.21-3.13 (m, 2H), 2.99 (qd, 2H), 2.73 (ddd, 3H), 2.56 (dd, 1H), 2.36 (dd, 1H), 1.69-1.58 (m, 4H), 1.55-1.38 (m, 4H), 1.14 (d, 3H). ¹³C NMR: 195.33, 176.94, 151.11, 140.18, 135.15, 133.84, 130.35, 129.39, 128.02, 127.14, 126.92, 126.69, 122.32, 120.40, 113.06, 110.68, 49.02, 40.91, 33.54, 29.66, 29.65, 29.55, 29.09, 28.96, 26.51, 26.33, 20.49.

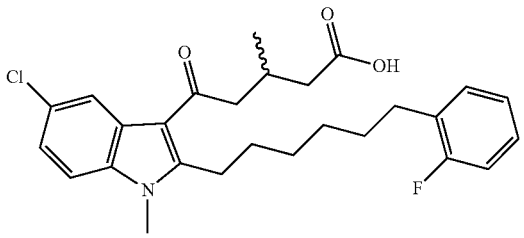 [SMILES: CC(CC(=O)O)CC(=O)c1c(CCCCCCc2ccccc2F)n(C)c2ccc(Cl)cc12]

5-(5-chloro-2-(6-(2-fluorophenyl)hexyl)-1-methyl-1H-indol-3-yl)-3-methyl-5-oxopentanoic acid (18)

¹H NMR (400 MHz, CDCl₃): δ 7.89 (s, 1H), 7.22-7.07 (m, 4H), 7.05-6.90 (m, 2H), 3.64 (s, 3H), 3.18-3.07 (m, 2H), 3.01 (dd, J=16.0, 6.7 Hz, 1H), 2.89 (dd, J=16.0, 6.7 Hz, 1H), 2.74 (dq, J=13.1, 6.4 Hz, 1H), 2.66-2.52 (m, 3H), 2.34 (dd, J=15.3, 7.6 Hz, 1H), 1.60 (dt, =14.6, 7.5 Hz, 4H), 1.47 (dd, J=14.4, 7.1 Hz, 2H), 1.43-1.32 (m, 2H), 1.12 (d, 6.6 Hz, 3H). ¹³C NMR: 193.27, 176.95, 159.48, 149.03, 133.28, 128.80 (d,), 127.56, 126.07, 125.52, 125.11, 122.06, 120.40, 118.58, 113.27, 111.27, 108.85, 47.27, 39.20, 28.23, 27.78, 27.71, 27.20, 27.15, 27.09, 24.55, 24.47, 18.52.

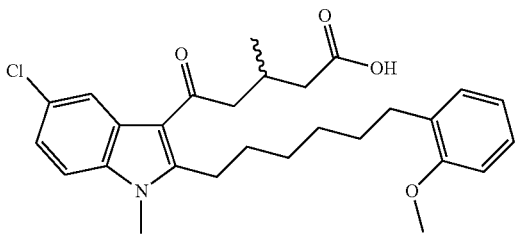 [SMILES: COc1ccccc1CCCCCCc1c(C(=O)CC(C)CC(=O)O)c2cc(Cl)ccc2n1C]

5-(5-chloro-2-(6-(2-methoxyphenyl)hexyl)-1-methyl-1H-indol-3-yl)-3-methyl-5-oxopentanoic acid (19)

¹H NMR (400 MHz, CDCl₃): δ 7.90 (d, J=1.1 Hz, 1H), 7.26-7.10 (m, 4H), 6.88-6.81 (m, 2H), 3.80 (s, 3H), 3.69 (s, 3H), 3.15 (t, J=7.6 Hz, 2H), 3.02 (dd, J=16.4, 7.1 Hz, 1H), 2.94 (dd, J=16.0, 6.6 Hz, 1H), 2.77-2.69 (m, 1H), 2.59-2.52 (m, 3H), 2.35 (dd, J=16.0, 7.4 Hz, 1H), 2.94 (dd, J=16.0, 6.5 Hz, 1H), 2.77-2.69 (m, 1H), 2.61-2.53 (m, 3H), 2.35 (dd, J=15.2, 7.4 Hz, 1H), 1.66-1.55 (m, 4H), 1.53-1.45 (m, 2H), 1.43-1.37 (m, 2H), 1.33 (d, J=6.7 Hz, 3H). ¹³C NMR: 195.14, 178.30, 157.42, 150.0, 135.13, 131.09, 129.75, 127.94, 126.97, 126.85, 122.25, 120.45, 120.33, 113.11, 110.63, 110.24, 55.27, 49.08, 41.0, 30.12, 29.77, 29.72, 29.64, 29.34, 29.10, 26.43, 26.37, 20.39.

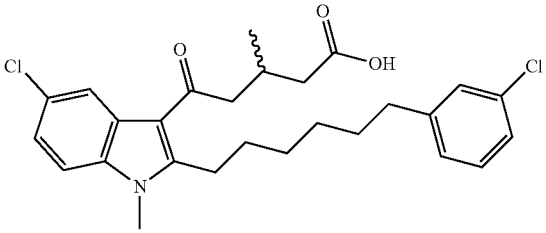 [SMILES: CC(CC(=O)O)CC(=O)c1c(CCCCCCc2cccc(Cl)c2)n(C)c2ccc(Cl)cc12]

5-(5-chloro-2-(6-(3-chlorophenyl)hexyl)-1-methyl-1H-indol-3-yl)-3-methyl-5-oxopentanoic acid (20)

¹H NMR (400 MHz, CDCl₃): δ 7.88 (s, 1H), 7.19 (m, 5H), 7.03 (d, =7.3 Hz, 1H), 3.70 (s, 3H), 3.21-3.11 (m, 2H), 3.06-2.94 (m, 2H), 2.72 (dd, =13.1, 6.6 Hz, 1H), 2.56 (dt, J=12.1, 6.4 Hz, 3H), 2.37 (dd, J=15.1, 7.2 Hz, 1H), 1.62 (dt, J=15.2, 7.6 Hz, 4H), 1.53-1.44 (m, 2H), 1.43-1.34 (m, 2H), 1.15 (d, J=6.7 Hz, 3H). ¹³C NMR: 195.48, 175.89, 151.19, 144.70, 135.17, 133.98, 129.51, 128.49, 128.09, 126.90, 126.63, 125.83, 122.38, 120.38, 113.04, 110.72, 49.00, 40.84, 35.56, 31.06, 29.67, 29.57, 28.94, 28.92, 26.60, 26.33, 20.56.

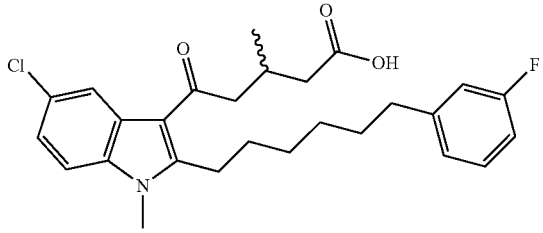 [SMILES: CC(CC(=O)O)CC(=O)c1c(CCCCCCc2cccc(F)c2)n(C)c2ccc(Cl)cc12]

5-(5-chloro-2-(6-(3-fluorophenyl)hexyl)-1-methyl-1H-indol-3-yl)-3-methyl-5-oxopentanoic acid (21)

¹H NMR (400 MHz, CDCl₃): 7.88 (s, 1H), 7.25-7.11 (m, 3H), 6.92 (d, J=7.6 Hz, 1H), 6.84 (t, J=7.9 Hz, 2H), 3.68 (s, 3H), 3.23-3.10 (m, 2H), 2.98 (ddd, =37.3, 16.1, 6.8 Hz, 2H), 2.73 (dq, J=13.2, 6.6 Hz, 1H), 2.63-2.52 (m, 3H), 2.35 (dd, J=15.2, 7.4 Hz, 1H), 1.68-1.55 (m, 4H), 1.54-1.43 (m, 2H), 1.38 (dt, J=14.0, 7.0 Hz, 2H), 1.13 (d, J=6.7 Hz, 3H). ¹³C NMR: 195.18, 177.95, 162.86, 150.92, 145.26, 135.11, 129.59, 127.96, 126.88, 124.04, 122.27, 120.38, 115.13, 113.08, 112.45, 110.66, 49.09, 40.95, 35.61, 31.03, 29.62, 29.58, 28.96, 28.93, 26.40, 26.29, 20.39.

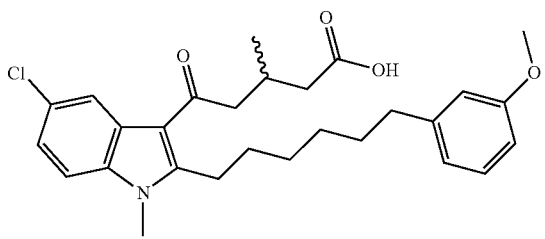 [SMILES: COc1cccc(CCCCCCc2c(C(=O)CC(C)CC(=O)O)c3cc(Cl)ccc3n2C)c1]

5-(5-chloro-2-(6-(3-methoxyphenyl)hexyl)-1-methyl-1H-indol-3-yl)-3-methyl-5-oxopentanoic acid (22)

¹H NMR (400 MHz, CDCl₃): δ 7.89 (d, J=1.2, Hz, 1H), 7.20 (ddd, J=16.5, 10.5, 8.2 Hz, 3H), 6.79-6.68 (m, 3H), 3.79 (s, 3H), 3.69 (s, 3H), 3.21-3.11 (m, 2H), 2.98 (qd, J=16.0, 6.8 Hz, 2H), 2.73 (dq, =13.3, 6.6 Hz, 1H), 2.64-2.51 (m, 3H), 2.36 (dd, J=15.2, 7.4 Hz, 1H), 1.69-1.57 (m, 4H), 1.53-1.44 (m, 2H), 1.44-1.34 (m, 2H), 1.14 (d, J=6.7 Hz, 3H). ¹³C NMR: 195.29, 177.11, 159.55, 151.05, 144.35, 135.14, 129.19, 128.01, 126.92, 122.30, 120.86, 120.41, 114.22, 113.07, 110.82, 110.66, 55.12, 49.03, 40.90, 35.93, 31.23, 29.65, 29.03, 29.01, 26.49, 26.33, 20.46.

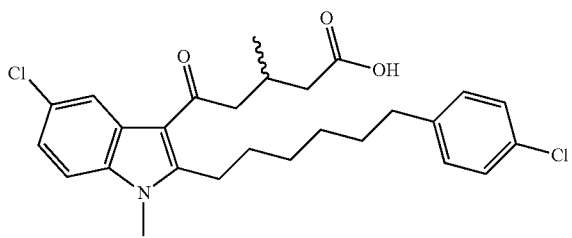 [SMILES: CC(CC(=O)O)CC(=O)c1c(CCCCCCc2ccc(Cl)cc2)n(C)c2ccc(Cl)cc12]

5-(5-chloro-2-(6-(4-chlorophenyl)hexyl)-1-methyl-1H-indol-3-yl)-3-methyl-5-oxopentanoic acid (23)

¹H NMR (400 MHz, CDCl₃): δ 7.87 (d, 1H), 7.25-7.20 (m, 4H), 7.08 (d, 2H), 3.70 (s, 3H), 3.22-3.10 (m, 2H), 3.00 (d, 2H), 2.71 (td, 1H), 2.60-2.51 (m, 3H), 2.37 (dd, 1H), 1.70-1.55 (m, 4H), 1.53-1.43 (m, 2H), 1.38 (dd, 2H), 1.16 (d, 3H). ¹³C NMR: 200.78, 151.32, 141.06, 131.32, 129.74, 128.34, 128.14, 126.90, 124.63, 122.41, 120.48, 120.37, 112.99, 110.74, 48.96, 35.22, 34.15, 31.23, 29.68, 29.59, 28.94, 28.90, 28.63, 26.68, 20.63.

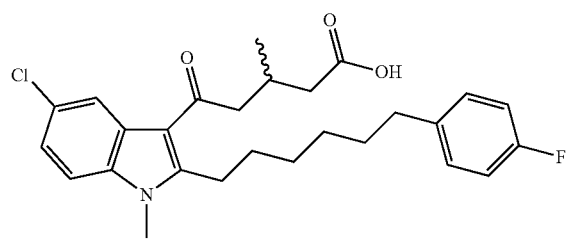 [SMILES: CC(CC(=O)O)CC(=O)c1c(CCCCCCc2ccc(F)cc2)n(C)c2ccc(Cl)cc12]

5-(5-chloro-2-(6-(4-fluorophenyl)hexyl)-1-methyl-1H-indol-3-yl)-3-methyl-5-oxopentanoic acid (24)

¹H NMR (400 MHz, CDCl₃): δ 11.02 (br s, 1H), 7.88 (d, J=1.1 Hz, 1H), 7.27-7.17 (m, 2H), 7.09 (q, J=5.6 Hz, 2H), 6.92 (t, J=8.7 Hz, 2H), 3.67 (s, 3H), 3.14 (t, J=7.6 Hz, 2H), 3.02 (dd, J=16.0, 6.9 Hz, 1H), 2.91 (dd, J=16.0, 6.7 Hz, 1H), 2.78-2.68 (m, 1H), 2.59-2.54 (m, 3H), 2.34 (dd, J=15.3, 7.5 Hz, 1H), 1.64-1.55 (m, 4H), 1.51-1.42 (m, 2H), 1.40-1.33 (m, 2H), 1.25 (d, J=6.6 Hz, 3H). ¹³C NMR: 195.15, 178.15, 162.34, 159.93, 150.89, 138.27, 138.24, 135.12, 129.69, 129.62, 127.95, 126.91, 122.26, 120.40, 115.03, 114.82, 113.12, 110.66, 49.13, 40.99, 35.06, 31.47, 29.62, 29.00, 28.94, 26.41, 26.29, 20.42.

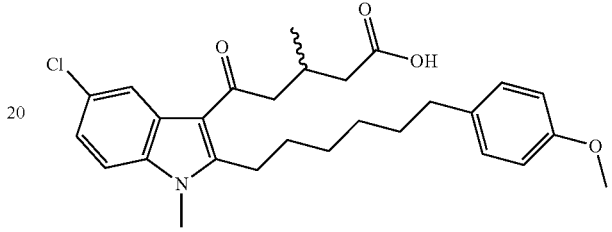

5-(5-chloro-2-(6-(4-methoxyphenyl)hexyl)-1-methyl-1H-indol-3-yl)-3-methyl-5-oxopentanoic acid (25)

¹H NMR (400 MHz, CDCl₃): δ 11.04 (br s, 1H), 7.89 (d, J=1.0 Hz, 1H), 7.27-7.18 (m, 2H), 7.07 (d, J=8.5 Hz, 2H), 6.81 (d, J=8.5 Hz, 2H), 3.77 (s, 3H), 3.68 (s, 3H), 3.15 (t, J=7.7 Hz, 2H), 3.02 (dd, J=16.4, 7.0 Hz, 1H), 2.93 (dd, J=16.0, 6.6 Hz, 1H), 2.77-2.67 (m, 1H), 2.59-2.52 (m, 3H), 2.35 (dd, J=15.2, 7.4 Hz, 1H), 1.65-1.55 (m, 4H), 1.51-1.44 (m, 2H), 1.41-1.34 (m, 2H), 1.13 (d, J=6.6 Hz, 3H). ¹³C NMR: 195.19, 177.88, 157.62, 150.99, 135.14, 134.79, 129.25, 127.98, 126.94, 122.28, 120.42, 113.68, 113.10, 110.65, 55.26, 49.08, 40.96, 34.96, 31.61, 29.67, 29.65, 29.04, 28.98, 26.45, 26.34, 20.42.

Scheme 2. Synthesis of Wittig Salt (5)

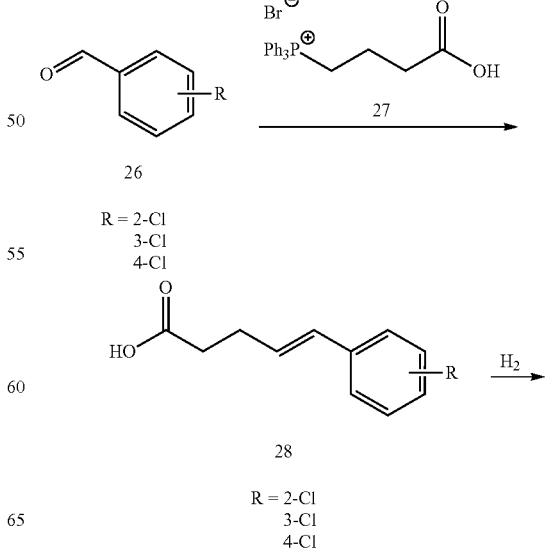

R = 2-Cl
3-Cl
4-Cl

R = 2-Cl
3-Cl
4-Cl

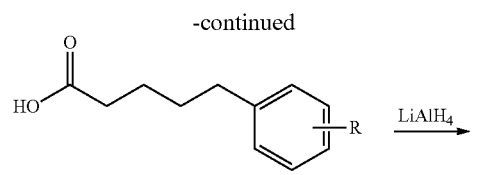

29

R = 2-Cl
3-Cl
4-Cl

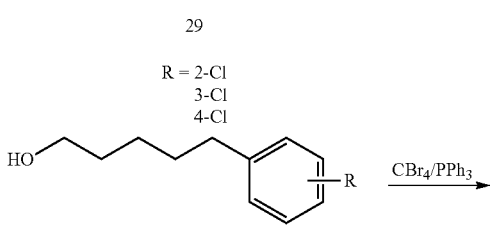

30

R = H
2-Cl
3-Cl
4-Cl

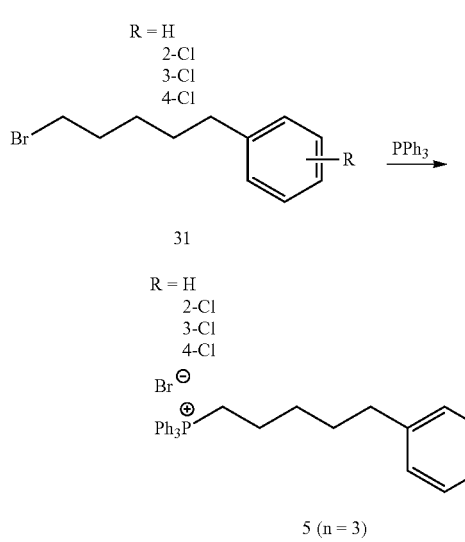

31

R = H
2-Cl
3-Cl
4-Cl 5 (n = 3)

R = H
2-Cl
3-Cl
4-Cl

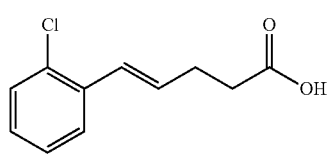 [SMILES: O=C(O)CC/C=C/c1ccccc1Cl]

Synthesis of 5-(2-chlorophenyl)pent-4-enoic acid (28)

To a suspension of 27 (25 g, 58.2 mmol) in THF (20 mL) was added t-BuOK (1.0 M in THF, 120 mL, 120 mmol) at 0° C. The mixture was stirred for 30 min, cooled back to 0° C., and 2-chlorobenzaldehyde (8.2 g, 58.34 mmol) in THF (20 ml) was added dropwise. The reaction mixture was allowed to warm to rt and stirred for 4 h. Saturated NH$_4$Cl solution was added at 0° C. and the crude was acidified to pH=3. The organic layer was extracted with EtOAc, and the combined organic layers were washed with brine, dried over Na$_2$SO$_4$ and evaporated under reduced pressure. The crude was purified by silica gel chromatography (20% EtOAc/Hexane) to afford 5-(2-chlorophenyl)pent-4-enoic acid as orange solid (12 g, 95%). $^1$H NMR (400 MHz, CDCl$_3$): δ 7.49 (dd, 1H), 7.33 (dd, 1H), 7.18 (m, 2H), 6.83 (d, 1H), 6.26-6.14 (m, 1H), 2.66-2.41 (m, 4H). $^{13}$C NMR: 178.45, 135.40, 132.73, 130.94, 129.62, 128.27, 127.56, 126.79, 126.75, 33.55, 28.06.

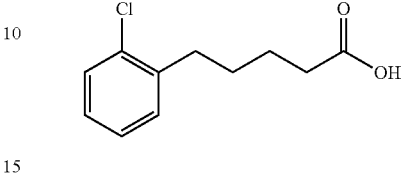

Synthesis of 5-(2-chlorophenyl)pentanoic acid (29)

To a stirred solution of 28 (12 g, 56.4 mmol) in benzene (120 mL) was added 10% Pd/C (1.2 g) under H$_2$ atm. The reaction mixture was stirred at rt for 8 h and then filtered. The residue was washed with EtOAc, and the combined filtrate was concentrated under reduced pressure to afford 5-(2-chlorophenyl)pentanoic acid as a liquid (12 g, 99%). $^1$H NMR (400 MHz, CDCl$_3$): δ 7.33 (d, 1H), 7.23-7.10 (m, 3H), 2.75 (t, 2H), 2.40 (t, 2H), 1.77-1.61 (m, 4H). $^{13}$C NMR: 179.83, 139.57, 133.90, 130.34, 129.50, 127.35, 126.76, 33.85, 33.20, 29.10, 24.34.

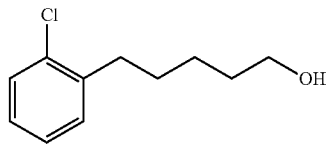 [SMILES: OCCCCCc1ccccc1Cl]

Synthesis of 5-(2-chlorophenyl)pentan-1-ol (30)

To a stirred solution of 29 (12 g, 55.9 mmol) in THF (120 ml) was added LiAlH$_4$ (4.64 g, 122.2 mmol) slowly at −20° C. Once the addition was complete the reaction mixture was allowed to warm to rt and stirred for 4 h. Water was added and the organic layer was dried over Na$_2$SO$_4$. The solvents were evaporated under reduced pressure to get the crude product (10.7 g, 88%), which was used without any further purification. $^1$H NMR (400 MHz, CDCl$_3$): δ 7.33 (dd, 1H), 7.23-7.09 (m, 3H), 3.65 (t, 2H), 2.80-2.69 (m, 2H), 1.72-1.55 (m, 4H), 1.51-1.39 (m, 2H). $^{13}$C NMR: 140.09, 133.89, 130.35, 129.45, 127.19, 126.69, 62.93, 33.56, 32.59, 29.56, 25.52.

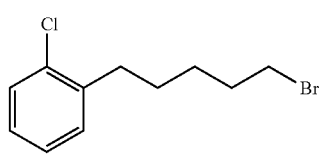 [SMILES: Clc1ccccc1CCCCCBr]

Synthesis of 1-(5-bromopentyl)-2-chlorobenzene (31)

To a stirred solution of 5-(2-chlorophenyl)pentan-1-ol (4.38 g, 22 mmol) in dichloromethane (40 ml) was added PPh₃ (6.93 g, 26.4 mmol) followed by CBr₄ (6.57 g, 19.8 mmol) at 0° C. The reaction mixture was allowed to warm to rt and stirred for 20 min. The solvents were evaporated under reduced pressure and the crude was purified by silica gel chromatography (100% Hexane) to afford 1-(5-bromopentyl)-2-chlorobenzene as a liquid (5.6 g, 97.3%). ¹H NMR (400 MHz, CDCl₃): δ 7.36-7.30 (m, 1H), 7.23-7.09 (m, 3H), 3.41 (t, 2H), 2.82-2.66 (m, 2H), 1.99-1.85 (m, 2H), 1.73-1.58 (m, 2H), 1.57-1.46 (m, 2H). ¹³C NMR: 139.86, 133.89, 130.35, 129.49, 127.30, 126.75, 33.78, 33.43, 32.61, 28.92, 27.93.

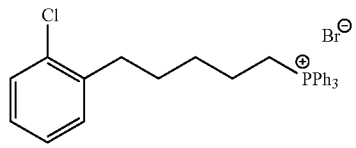

Synthesis of (5-(2-chlorophenyl)pentyl)triphenylphosphonium bromide (5, n=3, R=2-Cl)

To a stirred solution of 31 (4.84 g, 18.5 mmol) in acetonitrile (40 ml) was added PPh₃ (9.7 g, 37 mmol). The reaction mixture was reflux at 65° C. for 2 days. The solvent was evaporated under reduced pressure and the crude was purified by silica gel chromatography (10% MeOH/dichloromethane) to afford (5-(2-chlorophenyl)pentyl)triphenylphosphonium bromide as a white solid (7.4 g, 90%). ¹H NMR (400 MHz, CDCl₃): δ 7.90-7.66 (m, 15H), 7.25 (d, 1H), 7.21-7.05 (m, 3H), 3.85 (td, 2H), 2.72-2.58 (m, 2H), 1.75-1.50 (m, 6H). ¹³C NMR: 139.68, 134.97 (d), 133.72 (d), 130.66, 130.47 (d), 129.27, 127.24, 126.84, 118.85, 118.00, 32.99, 29.86 (d), 29.25, 22.97, 22.50.

Scheme 3. Synthesis of Wittig Salt (7)

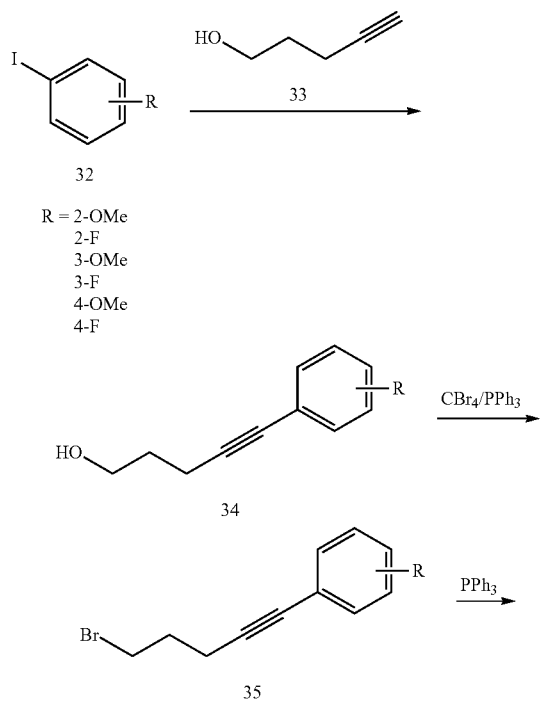

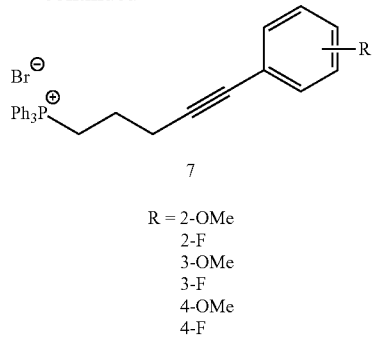

R = 2-OMe
2-F
3-OMe
3-F
4-OMe
4-F

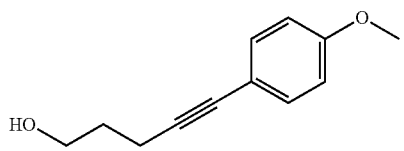

Synthesis of 5-(4-Methoxy-phenyl)-pent-4-yn-1-ol (34, R=4-OMe)

4-Iodo anisole 32 (8.7 g, 37.17 mmol), pent-4-yn-1-ol 33 (3.0 g, 35.66 mmol), Pd(OAc)₂ (320 mg, 1.42 mmol), PPh₃ (935 mg, 3.81 mmol), and CuI (678 mg, 5.25 mmol) in anhydrous diethylamine (15 mL) were stirred under argon for 3 h. The solvent was removed under reduced pressure and the residue was dissolved in EtOAc, washed with H₂O, dried over Na₂SO₄, and concentrated. The resulting solid was chromatographed (25% EtOAc/Hexanes) to give the product 34 (6.0 mg, 89%) as a wine red color liquid. ¹H NMR (400 MHz, CDCl₃): δ 7.32 (d, J=8.7 Hz, 2H), 6.80 (d, J=8.7 Hz, 2H), 3.80 (m, 5H), 2.51 (t, J=6.9 Hz, 2H), 1.85-1.82 (m, 2H). ¹³C NMR: 159.08, 132.87, 115.91, 113.85, 87.84, 80.80, 61.59, 55.22, 31.50, 15.95.

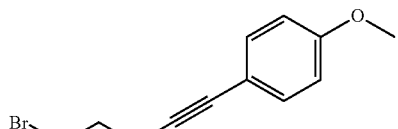

Synthesis of 1-(5-Bromo-pent-1-ynyl)-4-methoxybenzene (35, R=4-OMe)

To a stirred solution of 34 (R=4-methoxy) (6 g, 31.54 mmol) in dichloromethane (40 ml) was added PPh₃ (9.9 g, 37.74 mmol) followed by CBr₄ (10.4 g, 31.35 mmol) at 0° C. After stirring at 0° C. for 20 min, the reaction mixture were evaporated under reduced pressure and the crude was purified by silica gel chromatography (5% EtOAc/Hexanes) to afford 35 (R=4-OMe) as a light yellow liquid (7.4 g, 94%). ¹H NMR (400 MHz, CDCl₃): δ 7.32 (d, J=8.7 Hz, 2H), 6.81 (d, J=8.8 Hz, 2H), 3.79 (s, 3H), 3.57 (t, J=6.5 Hz, 2H), 2.58 (t, J=6.7 Hz, 2H), 2.13-2.10 (m, 2H). ¹³C NMR: 159.21, 132.91, 115.70, 113.85, 86.30, 81.36, 55.23, 32.52, 31.67, 18.15.

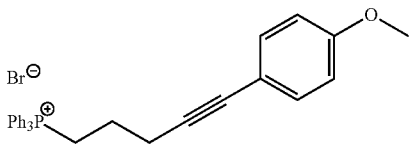

Synthesis of (5-(4-methoxyphenyl)pent-4-yn-1-yl) triphenylphosphonium bromide (7, R=4-OMe)

To a stirred solution of 35 (R=4-OMe) (7.0 g, 27.65 mmol) in acetonitrile (50 ml) was added PPh₃ (8.7 g, 33.16 mmol). The reaction mixture was reflux at 65° C. for 2 days. The solvent was evaporated under reduced pressure and the crude was purified by silica gel chromatography (10% MeOH/CH₂Cl₂) to afford 7 (R=4-OMe) as a solid (11.4 g, 80%). ¹H NMR (400 MHz, CDCl₃): δ 7.89-7.77 (m, 9H) 7.71-7.66 (m, 6H), 7.28 (d, J=7.2 Hz, 2H), 6.80 (d, J=8.8 Hz, 2H), 4.12-4.04 (m, 2H), 3.80 (s, 3H), 2.87 (t, J=6.4 Hz, 2H), 2.02-1.92 (m, 2H). ¹³C NMR: 59.35, 135.15, 135.13, 133.74, 133.64, 132.95, 130.62, 130.50, 118.57, 117.71, 115.35, 113.94, 86.72, 82.05, 55.34, 50.55, 22.42, 20.13.

Synthesis of 5-(5-chloro-2-(5-(4-hydroxyphenyl)pentyl)-1-methyl-1H-indol-3-yl)-3-methyl-5-oxopentanoic acid (39)

To a stirred solution of 25 (113 mg, 0.23 mmol) in CH₂Cl₂ (1 mL) was added BBr₃ (1.0 M in CH₂Cl₂, 0.7 mL, 0.7 mmol) at 0° C. The reaction mixture was stirred at rt for 1 h and then quenched by adding water. The aqueous layer was extracted with EtOAc, and the combined filtrate was concentrated under reduced pressure. The crude was purified by silica gel chromatography (50% EtOAc/Hexane) to afford 5-(5-chloro-2-(5-(4-hydroxyphenyl)pentyl)-1-methyl-1H-indol-3-yl)-3-methyl-5-oxopentanoic acid (12 mg, 11%). ¹H NMR (400 MHz, CDCl₃): δ 7.88 (d, J=1.0 Hz, 1H), 7.26-7.21 (m, 2H), 7.01 (d, J=8.2 Hz, 2H), 6.74 (d, J=8.3 Hz, 2H), 3.70 (s, 3H), 3.16 (t, J=7.4 Hz, 2H), 3.0 (d, J=6.8 Hz, 2H), 2.76-2.69 (m, 1H), 2.57-2.51 (m, 3H), 2.35 (dd, J=15.0, 7.2 Hz, 1H), 1.63-1.54 (m, 4H), 1.50-1.43 (m, 2H), 1.40-1.36 (m, 2H), 1.15 (d, J=6.6 Hz, 3H). ¹³C NMR: 195.66, 175.49, 153.60, 151.37, 135.18, 134.70, 129.42, 128.11, 126.93, 122.39, 120.39, 115.09, 113.0, 110.73, 48.95, 40.85, 34.92, 31.48, 29.71, 29.58, 28.96, 28.83, 26.65, 26.34, 20.58.

Compounds 37 and 38 were prepared in a similar manner as for compound 39 above and had the following characterization:

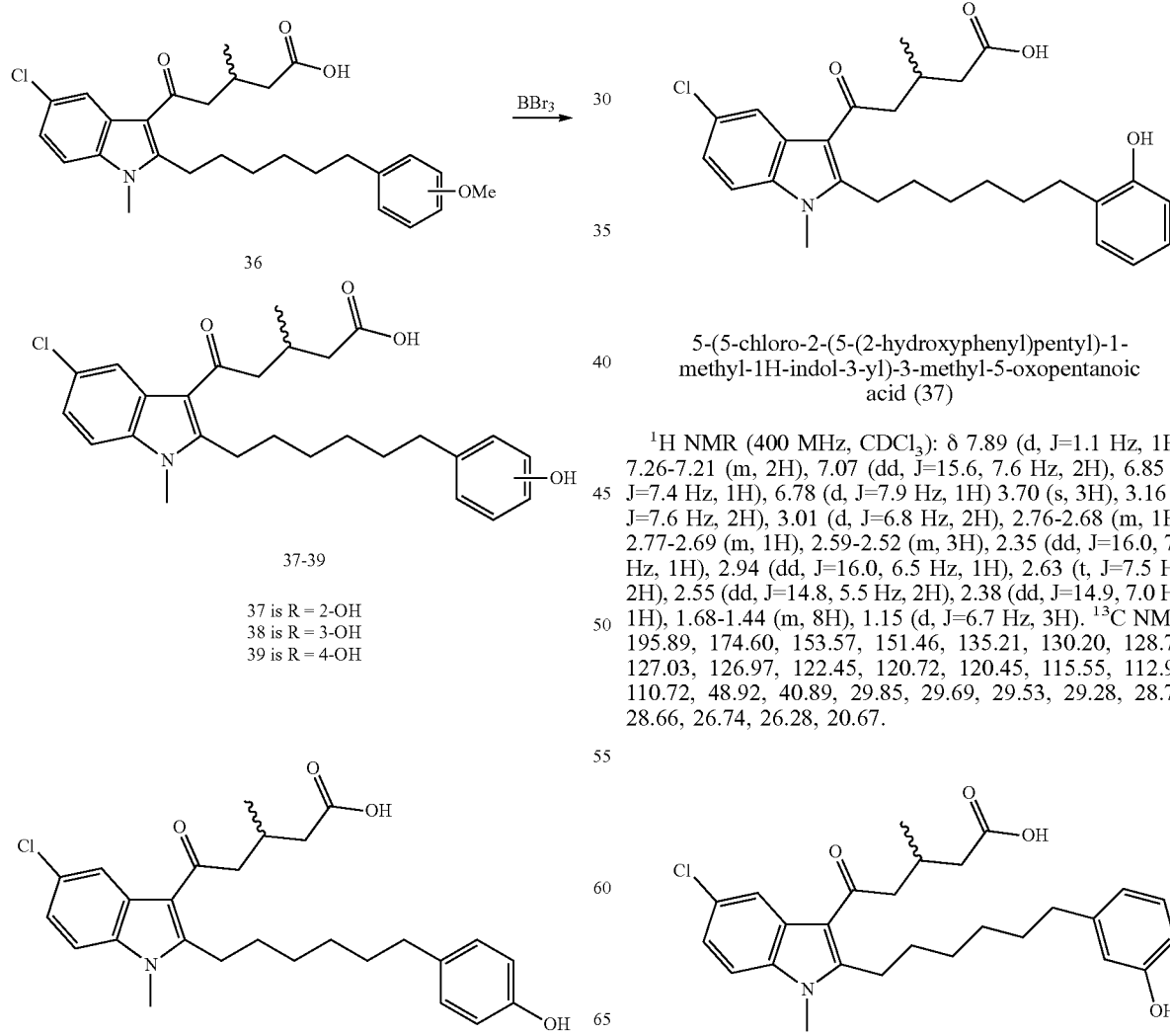

Scheme 4. Synthesis of Phenol Derivatives (37, 38, and 39)

37-39

37 is R = 2-OH
38 is R = 3-OH
39 is R = 4-OH

5-(5-chloro-2-(5-(2-hydroxyphenyl)pentyl)-1-methyl-1H-indol-3-yl)-3-methyl-5-oxopentanoic acid (37)

¹H NMR (400 MHz, CDCl₃): δ 7.89 (d, J=1.1 Hz, 1H), 7.26-7.21 (m, 2H), 7.07 (dd, J=15.6, 7.6 Hz, 2H), 6.85 (t, J=7.4 Hz, 1H), 6.78 (d, J=7.9 Hz, 1H) 3.70 (s, 3H), 3.16 (t, J=7.6 Hz, 2H), 3.01 (d, J=6.8 Hz, 2H), 2.76-2.68 (m, 1H), 2.77-2.69 (m, 1H), 2.59-2.52 (m, 3H), 2.35 (dd, J=16.0, 7.4 Hz, 1H), 2.94 (dd, J=16.0, 6.5 Hz, 1H), 2.63 (t, J=7.5 Hz, 2H), 2.55 (dd, J=14.8, 5.5 Hz, 2H), 2.38 (dd, J=14.9, 7.0 Hz, 1H), 1.68-1.44 (m, 8H), 1.15 (d, J=6.7 Hz, 3H). ¹³C NMR: 195.89, 174.60, 153.57, 151.46, 135.21, 130.20, 128.75, 127.03, 126.97, 122.45, 120.72, 120.45, 115.55, 112.97, 110.72, 48.92, 40.89, 29.85, 29.69, 29.53, 29.28, 28.73, 28.66, 26.74, 26.28, 20.67.

5-(5-chloro-2-(6-(3-hydroxyphenyl)hexyl)-1-methyl-1H-indol-3-yl)-3-methyl-5-oxopentanoic acid (38)

$^1$H NMR (400 MHz, CDCl$_3$): δ 7.87 (d, J=1.0 Hz, 1H), 7.26-7.19 (m, 2H), 7.12 (t, J=7.8 Hz, 1H), 6.76-6.63 (m, 3H), 3.70 (s, 3H), 3.17 (dd, J=13.5, 7.3 Hz, 2H), 3.04-2.99 (m, 2H), 2.78-2.66 (m, 1H), 2.61-2.50 (m, 3H), 2.37 (dd, J=15.1, 7.1 Hz, 1H), 1.68-1.56 (m, 4H), 1.54-1.44 (m, 2H), 1.40 (dd, J=14.5, 7.5 Hz, 2H), 1.16 (d, =6.7 Hz, 3H). $^{13}$C NMR: 196.03, 175.77, 155.83, 151.61, 144.36, 135.22, 129.40, 128.20, 126.93, 122.46, 120.71, 120.38, 115.40, 112.90, 112.72, 110.78, 49.09, 41.01, 35.42, 30.60, 29.69, 29.32, 28.65, 28.42, 26.68, 26.37, 20.69.

Scheme 5. Synthesis of S-isomers (46-55)

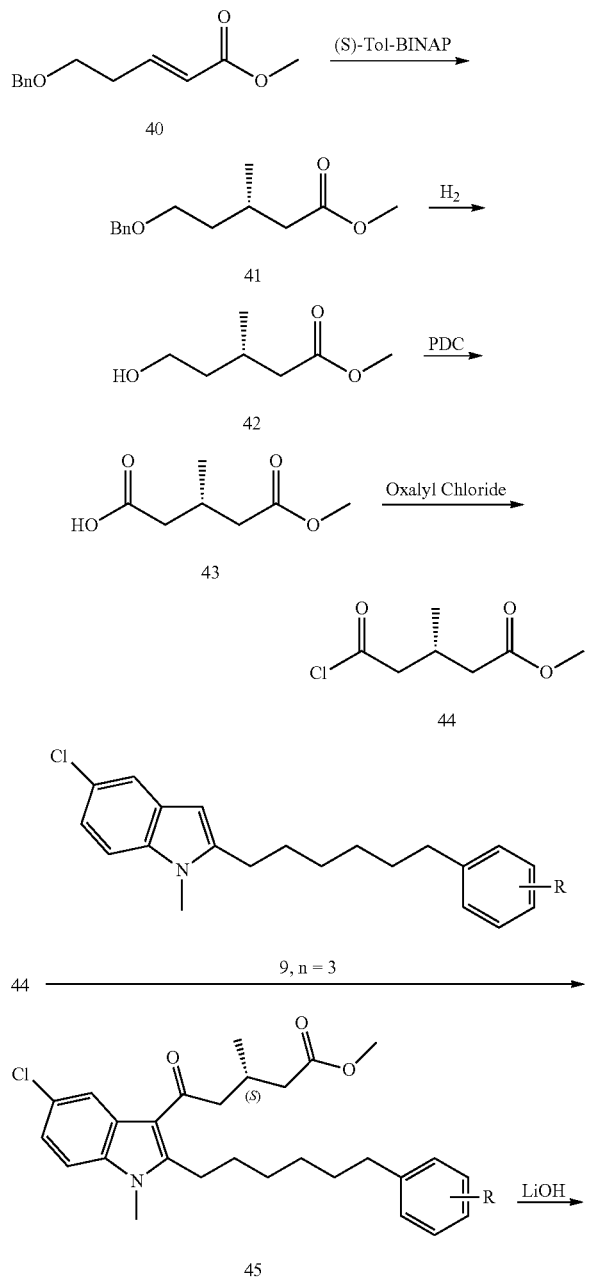

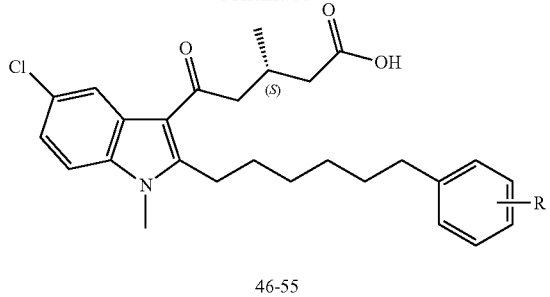

46 is R = H       51 is R = 3-F
47 is R = 2-Cl    52 is R = 3-OMe
48 is R = 2-F     53 is R = 4-Cl
49 is R = 2-OMe   54 is R = 4-F
50 is R = 3-Cl    55 is R = 4-OMe

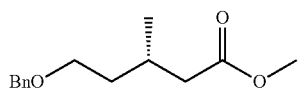 [SMILES: COC(=O)C[C@@H](C)CCOCc1ccccc1]

Synthesis of (S)-methyl 5-(benzyloxy)-3-methylpentanoate (41)

In a round bottom flask equipped with septum and stirring bar, (S)-Tol-BINAP (555 mg, 0.817 mmol) and CuBr (65 mg, 0.454 mmol) were dissolved in t-BuOMe (10 mL) and stirred under organ at rt until a bright yellow suspension was observed. The mixture was then cooled to –20° C. and MeMgBr (Aldrich, 3.0 M solution in Et$_2$O, 19.38 mL, 58.15 mmol) was added carefully into the reaction mixture. After stirring for 45 min, a solution of methyl (E)-5-(benzyloxy)pent-2-enoate (4.0 g, 18.17 mmol) in t-BuOMe (15 mL) was added dropwise over 0.5 h. After stirring at –20° C. for 2 h, MeOH (5 mL) and sat. NH$_4$Cl (10 mL) were sequentially added, and the mixture was warmed to rt. The aqueous layer was extracted with EtOAc (2×25 mL) and the combined organic extracts were dried over anhydrous Na$_2$SO$_4$. The solvents were evaporated under reduced pressure and purified by silica gel column chromatography using 4% EtOAc/n-Hexane to afford desired product (2.15 g, 50%) as colorless oil. HRMS (ESI) m/z calcd for [C$_{14}$H$_{20}$O$_3$+H]$^+$: 237.1491, found 237.1761. $^1$H NMR (400 MHz, CDCl$_3$): δ 7.36-7.26 (m, 5H), 4.49 (s, 2H), 3.65 (s, 3H), 3.51 (t, J=8.0 Hz, 2H), 2.35 (q, J=8.0 Hz, 1H), 2.18-2.11 (m, 2H), 1.72-1.64 (m, 1H), 1.56-1.48 (m, 1H), 0.96 (d, J=8.0 Hz, 3H). $^{13}$C NMR: 173.44, 138.55, 128.37, 127.62, 127.53, 72.92, 68.23, 51.38, 41.52, 36.32, 27.69, 19.83.

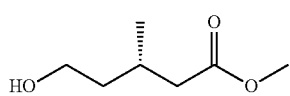

Synthesis of (S)-methyl 5-hydroxy-3-methylpentanoate (42)

A stirred solution of (9-methyl 5-(benzyloxy)-3-methylpentanoate (2.1 g, 8.89 mmol) and 10% Pd/C (210 mg) in 12 mL of anhydrous EtOAc, and 3 mL of absolute ethanol and was hydrogenated at 1 atm and at room temperature for 6 h. The reaction mixture was filtered through Celite pad and the filtrate was concentrated under reduced pressure to yielded primary alcohol as colorless liquid which was directly used for the next step without further purification (1.09 g, 85%). HRMS (ESI) m/z calcd for [C$_7$H$_{14}$O$_3$+H]$^+$: 147.1021, found 147.1249. $^1$H NMR (400 MHz, CDCl$_3$): δ 3.68 (s, 3H), 3.67 (t, J=12.0 Hz, 2H), 2.38-2.32 (m, 1H), 2.24-2.13 (m, 2H), 1.77-1.66 (m, 2H), 1.25 (br s, 1H), 0.97 (d, J=4.0 Hz, 3H). $^{13}$C NMR: 173.77, 60.44, 51.53, 41.39, 39.45, 26.99, 20.09.

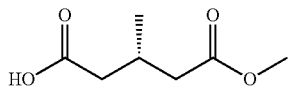

Synthesis of
(S)-5-methoxy-3-methyl-5-oxopentanoic acid (43)

Solid pyridinium dichromate (PDC) (12.87 g, 34.22 mmol) was added to a solution of alcohol (9-methyl 5-hydroxy-3-methylpentanoate (1.0 g, 6.84 mmol) in anhydrous DMF (10 mL) at 0° C. The resulting mixture was stir at rt for 12 h. Ice cold water (20 mL) was added and the resulting mixture was extracted with EtOAc and the combined organic layers washed with brine and dried over anhydrous Na$_2$SO$_4$. The solvents were evaporated under reduced pressure and purified by silica gel column chromatography using 30% EtOAc/n-Hexane to afford (S)-5-methoxy-3-methyl-5-oxopentanoic acid (986 mg, 90%) as colorless oil. HRMS (ESI) m/z calcd for [C$_7$H$_{12}$O$_4$+H]$^+$: 161.0814, found 161.0815. $^1$H NMR (400 MHz, CDCl$_3$): δ 10.78 (br s, 1H), 3.68 (s, 3H), 2.52-2.40 (m, 3H), 2.29 (dd, J=16.0, 8.0 Hz, 2H), 1.04 (d, J=4.0 Hz, 3H). $^{13}$C NMR: 178.42, 172.88, 51.59, 40.50, 40.57, 27.17, 19.81.

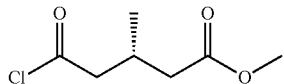

Synthesis of (R)-methyl
5-chloro-3-methyl-5-oxopentanoate (44)

To a stirred solution of (9-5-methoxy-3-methyl-5-oxopentanoic acid (900 mg, 1.62 mmol) in CH$_2$Cl$_2$ (15 mL) was added oxalyl chloride (2.0 M in CH$_2$Cl$_2$, 6.24 mL, 12.49 mmol) dropwise followed by a drop of DMF at 0° C. The reaction mixture was stirred at rt for 3 h. The solvents were evaporated in vacuo. The crude acid chloride was used further without any purification.

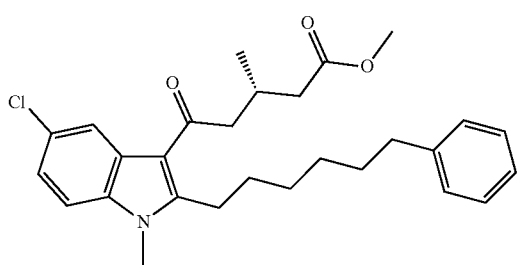 [SMILES: COC(=O)C[C@@H](C)CC(=O)c1c(CCCCCCc2ccccc2)n(C)c2ccc(Cl)cc12]

Synthesis of methyl (S)-5-(5-chloro-1-methyl-2-(6-phenylhexyl)-1H-indol-3-yl)-3-methyl-5-oxopentanoate (45)

To a stirred solution of 5-chloro-1-methyl-2-(6-phenylhexyl)-1H-indole (1 g, 3.1 mmol) in dichloromethane was added Me$_2$AlCl (1.0 M in hexane, 6.2 mL, 6.2 mmol) at 0° C. After 45 min, 5-chloro-3-methyl-5-oxopentanoate (655 mg, 3.68 mmol) in CH$_2$Cl$_2$ (6 mL) was added dropwise at rt and the reaction mixture stirred for 1 h. The reaction was quenched by adding water and extracted with EtOAc. The organic layers were combined, washed with brine and dried over Na$_2$SO$_4$. The solvents were evaporated under reduced pressure and the crude was purified by silica gel chromatography using 20% EtOAc/Hex as eluent to afford (S)-5-(5-chloro-1-methyl-2-(6-phenylhexyl)-1H-indol-3-yl)-3-methyl-5-oxopentanoate (1.3 g, 90%). $^1$H NMR (400 MHz, CDCl$_3$): δ 7.89 (d, 1H), 7.30-7.21 (m, 4H), 7.21-7.13 (m, 3H), 3.69 (s, 3H), 3.68 (s, 3H), 3.20-3.12 (m, 2H), 3.02 (dd, 1H), 2.89 (dd, 1H), 2.75 (dd, 1H), 2.60 (t, 2H), 2.52 (dd, 1H), 2.32 (dd, 1H), 1.69-1.58 (m, 4H), 1.53-1.34 (m, 4H), 1.09 (d, 3H). $^{13}$C NMR: 194.91, 173.17, 150.63, 142.69, 135.10, 128.39 (s), 128.24, 127.83, 126.92, 125.62, 122.17, 120.43, 113.23, 110.59, 51.46, 49.37, 41.12, 35.92, 31.39, 29.66 (s), 29.61, 29.08, 29.05, 26.50, 26.28, 20.35.

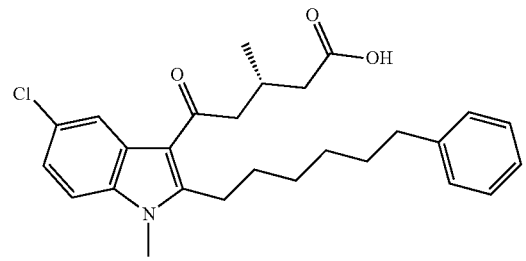 [SMILES: C[C@H](CC(=O)O)CC(=O)c1c(CCCCCCc2ccccc2)n(C)c2ccc(Cl)cc12]

Synthesis of (S)-5-(5-chloro-1-methyl-2-(6-phenylhexyl)-1H-indol-3-yl)-3-methyl-5-oxopentanoic acid (46)

To a stirred solution of (S)-5-(5-chloro-1-methyl-2-(6-phenylhexyl)-1H-indol-3-yl)-3-methyl-5-oxopentanoate (507 mg, 1.2 mmol) in THF/H$_2$O (4/1, 6 ml) was added LiOH (500 mg, 24.4 mmol). The reaction mixture was stirred for 48 h in rt and the THF was evaporated under reduced pressure. The aqueous layer was acidified with 4 N HCl and then extracted with EtOAc, the organic layers were combined, washed with brine and dried over Na$_2$SO$_4$. The solvents were evaporated under reduced pressure to afford 5-(5-chloro-1-methyl-2-(6-phenylhexyl)-1H-indol-3-yl)-3-methyl-5-oxopentanoic acid (1.05 g, 95%). HRMS (ESI) m/z calcd for [C$_{27}$H$_{32}$ClNO$_3$+H]$^+$: 454.2143, found 454.2357. $^1$H NMR (400 MHz, CDCl$_3$): δ 11.05 (br s, 1H) 7.89 (d, J=0.9 Hz, 1H), 7.26-7.20 (m, 2H), 7.18-7.13 (m, 5H), 3.64 (s, 3H), 3.12 (t, J=7.6 Hz, 2H), 3.01 (dd, J=16.0, 6.6 Hz, 1H), 2.90 (dd, J=16.0, 6.7 Hz, 1H), 2.79-2.68 (m, 1H), 2.61-2.53 (m, 3H), 2.33 (dd, J=15.3, 7.5 Hz, 1H), 1.66-1.56 (m, 4H), 1.51-1.44 (m, 2H), 1.42-1.33 (m, 2H), 1.12 (d, J=6.8 Hz, 3H). $^{13}$C NMR: 195.11, 178.65, 150.90, 142.71, 135.13, 128.42 128.27, 127.94, 126.96, 125.64, 122.25, 120.04, 113.13, 110.67, 49.12, 41.03, 35.93, 31.40, 29.67, 29.63, 29.07, 29.05, 26.41, 26.33, 20.38.

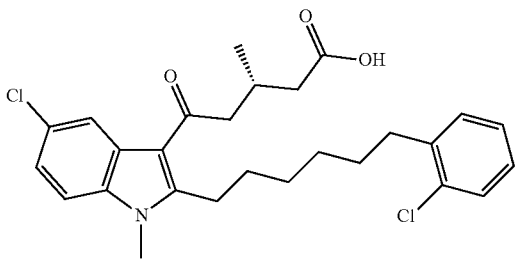

(S)-5-(5-chloro-2-(6-(2-chlorophenyl)hexyl)-1-methyl-1H-indol-3-yl)-3-methyl-5-oxopentanoic acid (47)

¹H NMR (400 MHz, CDCl₃): δ 7.89 (s, 1H), 7.31 (d, 1H), 7.25-7.06 (m, 5H), 3.70 (s, 3H), 3.21-3.13 (m, 2H), 2.99 (qd, 2H), 2.73 (ddd, 3H), 2.56 (dd, 1H), 2.36 (dd, 1H), 1.69-1.58 (m, 4H), 1.55-1.38 (m, 4H), 1.14 (d, 3H). ¹³C NMR: 195.33, 176.94, 151.11, 140.18, 135.15, 133.84, 130.35, 129.39, 128.02, 127.14, 126.92, 126.69, 122.32, 120.40, 113.06, 110.68, 49.02, 40.91, 33.54, 29.66, 29.65, 29.55, 29.09, 28.96, 26.51, 26.33, 20.49.

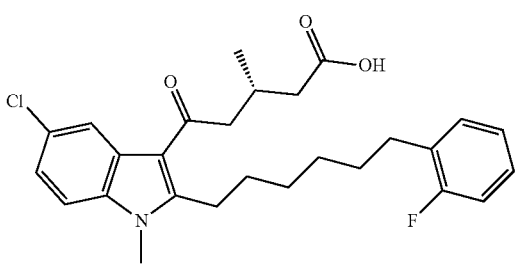 [SMILES: C[C@H](CC(=O)O)CC(=O)c1c(CCCCCCc2ccccc2F)n(C)c2ccc(Cl)cc12]

(S)-5-(5-chloro-2-(6-(2-fluorophenyl)hexyl)-1-methyl-1H-indol-3-yl)-3-methyl-5-oxopentanoic acid (48)

The enantiomer was obtained by chiral HPLC separation from compound 18 as first eluting compound.

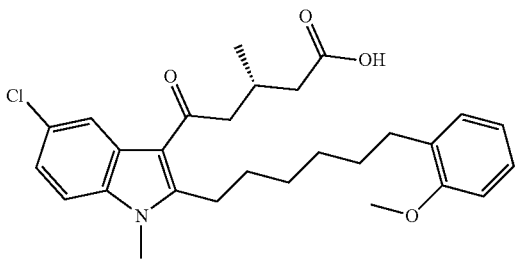 [SMILES: COc1ccccc1CCCCCCc1c(C(=O)C[C@H](C)CC(=O)O)c2cc(Cl)ccc2n1C]

(S)-5-(5-chloro-2-(6-(2-methoxyphenyl)hexyl)-1-methyl-1H-indol-3-yl)-3-methyl-5-oxopentanoic acid (49): ¹H NMR (400 MHz, CDCl₃): δ 7.90 (d, J=1.1 Hz, 1H), 7.26-7.10 (m, 4H), 6.88-6.81 (m, 2H), 3.80 (s, 3H), 3.69 (s, 3H), 3.15 (t, J=7.6 Hz, 2H), 3.02 (dd, J=16.0, 7.1 Hz, 1H), 2.94 (dd, J=16.0, 6.5 Hz, 1H), 2.77-2.69 (m, 1H), 2.59-2.52 (m, 3H), 2.35 (dd, J=16.0, 6.5 Hz, 1H), 2.94 (dd, J=16.0, 7.4 Hz, 1H), 2.77-2.69 (m, 1H), 2.61-2.53 (m, 3H), 2.35 (dd, J=15.2, 7.4 Hz, 1H), 1.66-1.55 (m, 4H), 1.53-1.45 (m, 2H), 1.43-1.37 (m, 2H), 1.33 (d, J=6.7 Hz, 3H). ¹³C NMR: 195.14, 178.30, 157.42, 150.0, 135.13, 131.09, 129.75, 127.94, 126.97, 126.85, 122.25, 120.45, 120.33, 113.11, 110.63, 110.24, 55.27, 49.08, 41.0, 30.12, 29.77, 29.72, 29.64, 29.34, 29.10, 26.43, 26.37, 20.39.

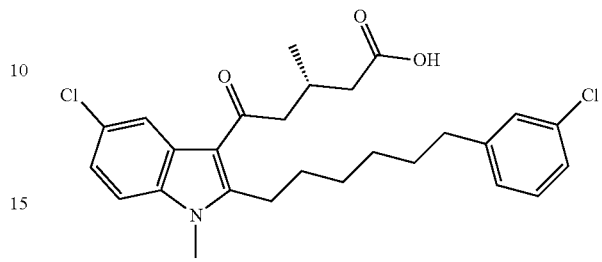

(S)-5-(5-chloro-2-(6-(3-chlorophenyl)hexyl)-1-methyl-1H-indol-3-yl)-3-methyl-5-oxopentanoic acid (50)

1H NMR (400 MHz, CDCl3): δ 7.88 (d, J=1.8 Hz, 1H), 7.25-7.11 (m, 5H), 7.03 (d, J=7.3 Hz, 1H), 3.70 (s, 3H), 3.22-3.12 (m, 2H), 2.99 (qd, J=16.1, 6.9 Hz, 2H), 2.73 (h, J=6.7 Hz, 1H), 2.63-2.50 (m, 3H), 2.36 (dd, J=15.2, 7.3 Hz, 1H), 1.61 (p, J=7.6 Hz, 4H), 1.48 (p, J=7.1 Hz, 2H), 1.39 (q, J=7.6 Hz, 2H), 1.14 (d, J=6.7 Hz, 3H). 13C NMR: 195.13, 178.32, 150.88, 144.72, 135.12, 133.95, 129.50, 128.48, 127.96, 126.90, 126.63, 125.81, 122.27, 120.40, 113.11, 110.67, 49.12, 40.99, 35.57, 31.08, 29.65, 29.58, 28.98, 26.40, 26.30, 20.41.

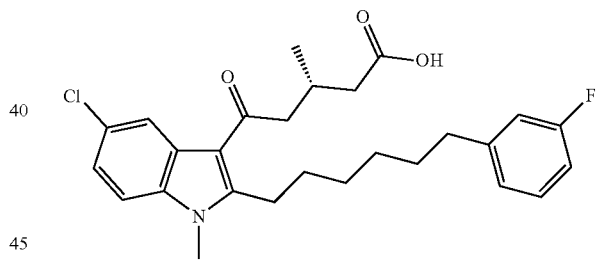

(S)-5-(5-chloro-2-(6-(3-fluorophenyl)hexyl)-1-methyl-1H-indol-3-yl)-3-methyl-5-oxopentanoic acid (51)

The enantiomer was obtained by chiral HPLC separation from compound 21 as first eluting compound.

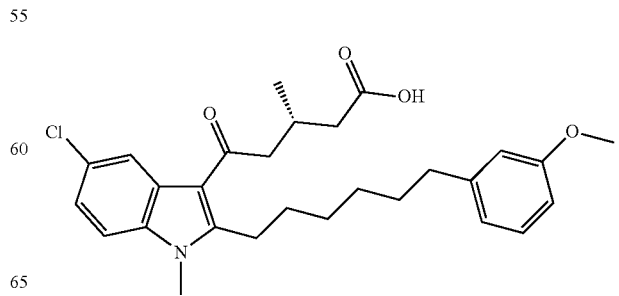

(S)-5-(5-chloro-2-(6-(3-methoxyphenyl)hexyl)-1-methyl-1H-indol-3-yl)-3-methyl-5-oxopentanoic acid (52)

The enantiomer was obtained by chiral HPLC separation from compound 22 as first eluting compound.

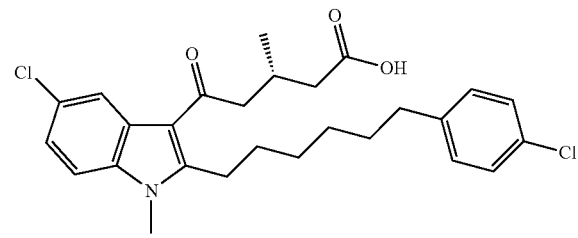 [SMILES: C[C@H](CC(=O)O)CC(=O)c1c(CCCCCCc2ccc(Cl)cc2)n(C)c2ccc(Cl)cc12]

(S)-5-(5-chloro-2-(6-(4-chlorophenyl)hexyl)-1-methyl-1H-indol-3-yl)-3-methyl-5-oxopentanoic acid (53)

$^1$H NMR (400 MHz, CDCl$_3$): The compound was prepared in accordance with Scheme 5. δ 7.87 (d, 1H), 7.25-7.20 (m, 4H), 7.08 (d, 2H), 3.70 (s, 3H), 3.22-3.10 (m, 2H), 3.00 (d, 2H), 2.71 (td, 1H), 2.60-2.51 (m, 3H), 2.37 (dd, 1H), 1.70-1.55 (m, 4H), 1.53-1.43 (m, 2H), 1.38 (dd, 2H), 1.16 (d, 3H). $^{13}$C NMR: 200.78, 151.32, 141.06, 131.32, 129.74, 128.34, 128.14, 126.90, 124.63, 122.41, 120.48, 120.37, 112.99, 110.74, 48.96, 35.22, 34.15, 31.23, 29.68, 29.59, 28.94, 28.90, 28.63, 26.68, 20.63.

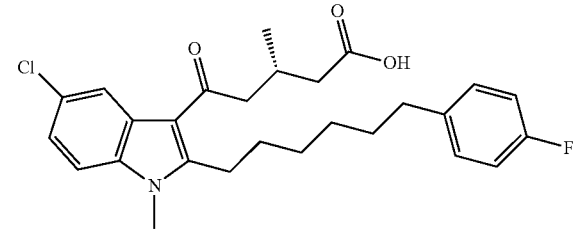 [SMILES: C[C@H](CC(=O)O)CC(=O)c1c(CCCCCCc2ccc(F)cc2)n(C)c2ccc(Cl)cc12]

(S)-5-(5-chloro-2-(6-(4-fluorophenyl)hexyl)-1-methyl-1H-indol-3-yl)-3-methyl-5-oxopentanoic acid (54)

$^1$H NMR (400 MHz, CDCl$_3$): The compound was prepared in accordance with Scheme 5. δ 11.03 (br s, 1H), 7.88 (d, J=1.0 Hz, 1H), 7.26-7.19 (m, 2H), 7.09 (q, J=5.7 Hz, 2H), 6.93 (t, J=8.6 Hz, 2H), 3.68 (s, 3H), 3.15 (t, J=7.7 Hz, 2H), 3.02 (dd, J=16.0, 7.0 Hz, 1H), 2.93 (dd, J=16.0, 6.6 Hz, 1H), 2.77-2.69 (m, 1H), 2.59-2.53 (m, 3H), 2.35 (dd, J=15.2, 7.4 Hz, 1H), 1.65-1.56 (m, 4H), 1.51-1.44 (m, 2H), 1.41-1.33 (m, 2H), 1.13 (d, J=6.6 Hz, 3H). $^{13}$C NMR: 195.20, 177.78, 162.35, 159.93, 150.96, 138.26, 138.22, 135.13, 129.68, 129.61, 127.99, 126.90, 122.29, 120.40, 115.03, 114.82, 113.10, 110.66, 49.10, 40.95, 35.06, 31.47, 29.61, 29.00, 28.93, 26.44, 26.31, 20.42.

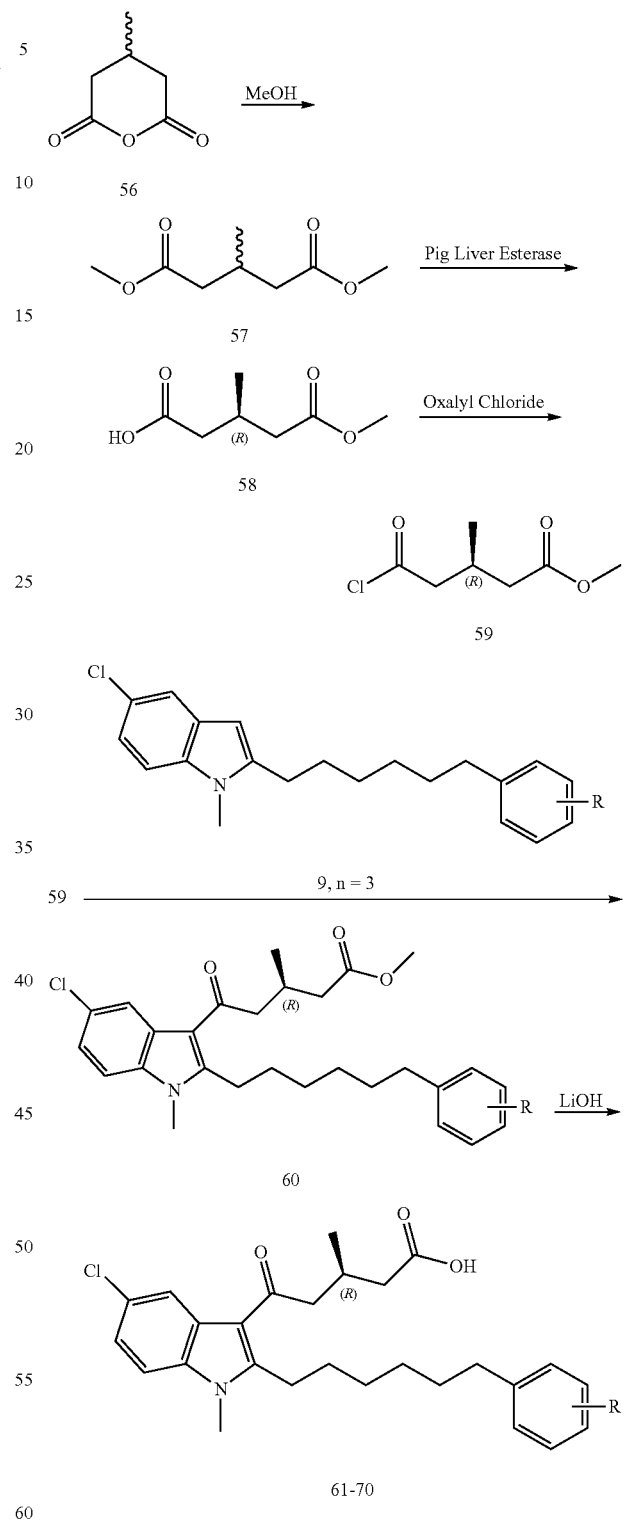

Scheme 6. Synthesis of R-Synthon (61-70)

61 is R = H
62 is R = 2-Cl
63 is R = 2-F
64 is R = 2-OMe
65 is R = 3-Cl
66 is R = 3-F
67 is R = 3-OMe
68 is R = 4-Cl
69 is R = 4-F
70 is R = 4-OMe

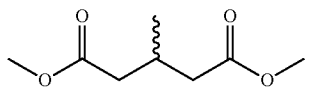

Dimethyl 3-methylpentanedioate (57)

To a 50 ml round bottom flask containing 3-Methyl glutaric anhydride 56 (400 mg, 3.12 mmol) was added methanol (7 mL), conc. HCl (5 drops) and conc. $H_2SO_4$ (5 drops). The reaction mixture was refluxed at 70° C. for 12 h. After that the mixture was cooled to rt and the solvents were evaporated to obtain the crude that was purified by silica gel column chromatography using 30% EtOAc/n-Hex to afford 57 (530 mg, 98%) as a colorless liquid. HRMS (ESI) m/z calcd for $[C_8H_{14}O_4+H]^+$: 175.0970, found 175.0972. $^1$H NMR (400 MHz, $CDCl_3$): δ 3.67 (s, 6H), 2.47 (dt, J=13.1, 6.7 Hz, 1H), 2.42 (d, J=5.7 Hz, 1H), 2.38 (d, J=6.2 Hz, 1H), 2.27 (d, J=7.3 Hz, 1H), 1.02 (d, J=8.0 Hz, 3H). $^{13}$C NMR: 172.81, 51.49, 40.62, 27.48, 19.89.

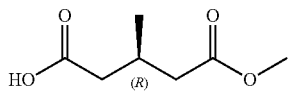

(R)-5-methoxy-3-methyl-5-oxopentanoic acid (58)

To a stirred solution of 57 (450 mg, 2.58 mmol) in a 100 mL round bottom flask was added 0.03 M $KH_2PO_4$ buffer (10 ml) followed by Pig liver esterase (10.4 mg) at 0° C. The reaction mixture was allowed to warm to rt and stirred for 10 min. The pH of the reaction mixture was adjusted to 7 by adding 0.5 M aqueous solution of NaOH drop wise over a period of 7 h. The reaction mixture was cooled to −78° C. and then stored in a refrigerator for overnight. Brine (7 mL) of was added and the resulting cold solution was washed with ether (3×20 mL) and then acidified to pH<2.5 with concentrated HCl. The aqueous layer was extracted with ether (2×20 mL), dried over $Na_2SO_4$ and concentrated in vacuo to yield 57 (370 mg, 89.6%) that was used without any further purification. HRMS (ESI) m/z calcd for $[C_7H_{12}O_4+H]^+$: 161.0814, found 161.0815. $^1$H NMR (400 MHz, $CDCl_3$): δ 8.04 (br s, 1H), 3.68 (s, 3H), 2.49-2.40 (m, 3H), 2.28 (dd, J=14.8, 6.6 Hz, 2H), 1.03 (d, J=5.6 Hz, 3H). $^{13}$C NMR: 177.09, 173.10, 51.66, 40.65, 40.57, 27.24, 19.84.

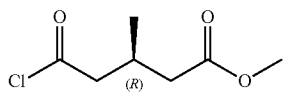

(S)-methyl 5-chloro-3-methyl-5-oxopentanoate (59)

To a stirred solution of 58 (700 mg, 4.37 mmol) in anhydrous $CH_2Cl_2$ (10 mL) was added oxalyl chloride (2.0 M in $CH_2Cl_2$, 2.62 ml, 5.24 mmol) dropwise at 0° C. followed by a drop of DMF. The reaction mixture was allowed to warm to rt and stirred for 3 h. The solvents were evaporated under reduced pressure and the crude acid chloride 59 was used for further without any purification.

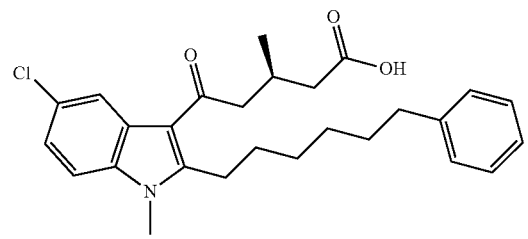 [SMILES: C[C@@H](CC(=O)O)CC(=O)c1c(CCCCCCc2ccccc2)n(C)c2ccc(Cl)cc12]

(R)-5-(5-chloro-1-methyl-2-(6-phenylhexyl)-1H-indol-3-yl)-3-methyl-5-oxopentanoic acid (61)

The enantiomer was obtained by chiral HPLC separation from compound 15 as second eluting compound.

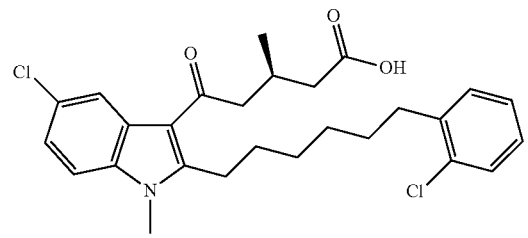

(R)-5-(5-chloro-2-(6-(2-chlorophenyl)hexyl)-1-methyl-1H-indol-3-yl)-3-methyl-5-oxopentanoic acid (62)

The enantiomer was obtained by chiral HPLC separation from compound 17 as second eluting compound.

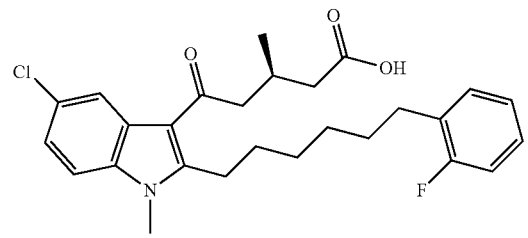 [SMILES: C[C@@H](CC(=O)O)CC(=O)c1c(CCCCCCc2ccccc2F)n(C)c2ccc(Cl)cc12]

(R)-5-(5-chloro-2-(6-(2-fluorophenyl)hexyl)-1-methyl-1H-indol-3-yl)-3-methyl-5-oxopentanoic acid (63)

The enantiomer was obtained by chiral HPLC separation from compound 18 as second eluting compound.

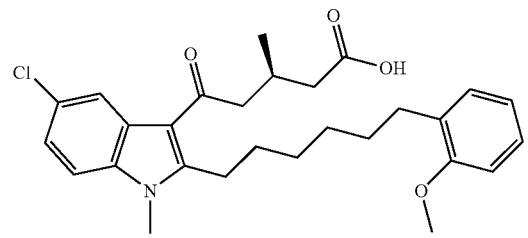 [SMILES: COc1ccccc1CCCCCCc1c(C(=O)C[C@@H](C)CC(=O)O)c2cc(Cl)ccc2n1C]

(R)-5-(5-chloro-2-(6-(2-methoxyphenyl)hexyl)-1-methyl-1H-indol-3-yl)-3-methyl-5-oxopentanoic acid (64)

The enantiomer was obtained by chiral HPLC separation from compound 19 as second eluting compound.

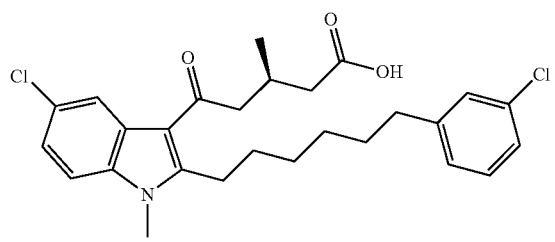 [SMILES: C[C@@H](CC(=O)O)CC(=O)c1c(CCCCCCc2cccc(Cl)c2)n(C)c2ccc(Cl)cc12]

(R)-5-(5-chloro-2-(6-(3-chlorophenyl)hexyl)-1-methyl-1H-indol-3-yl)-3-methyl-5-oxopentanoic acid (65)

The enantiomer was obtained by chiral HPLC separation from compound 20 as second eluting compound.

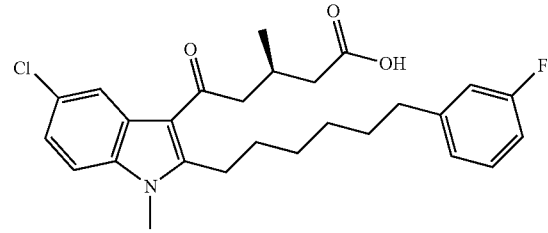 [SMILES: COc1cccc(CCCCCCc2c(C(=O)C[C@@H](C)CC(=O)O)c3cc(Cl)ccc3n2C)c1]

(R)-5-(5-chloro-2-(6-(3-fluorophenyl)hexyl)-1-methyl-1H-indol-3-yl)-3-methyl-5-oxopentanoic acid (66)

The enantiomer was obtained by chiral HPLC separation from compound 21 as second eluting compound.

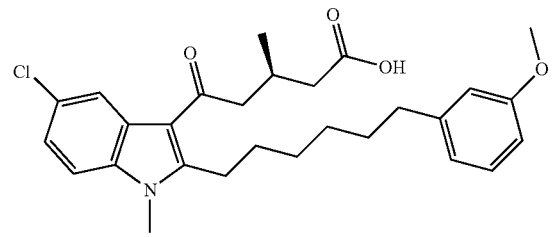

(R)-5-(5-chloro-2-(6-(3-methoxyphenyl)hexyl)-1-methyl-1H-indol-3-yl)-3-methyl-5-oxopentanoic acid (67)

The enantiomer was obtained by chiral HPLC separation from compound 22 as second eluting compound.

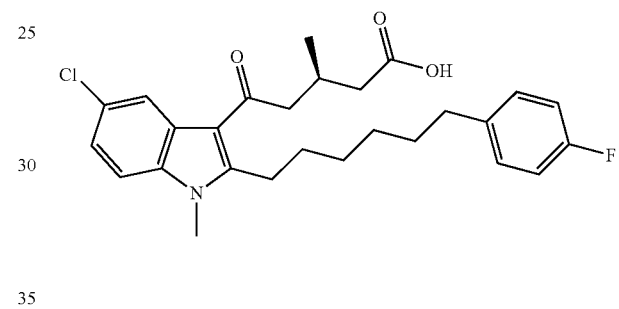

(R)-5-(5-chloro-2-(6-(4-fluorophenyl)hexyl)-1-methyl-1H-indol-3-yl)-3-methyl-5-oxopentanoic acid (69)

The enantiomer was obtained by chiral HPLC separation from compound 24 as second eluting compound.

Scheme 8. Synthesis of Ether Derivatives

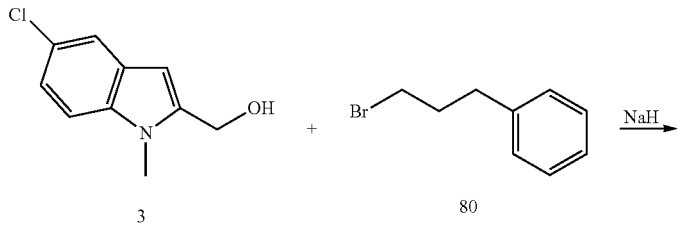

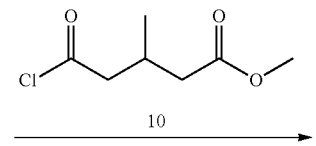

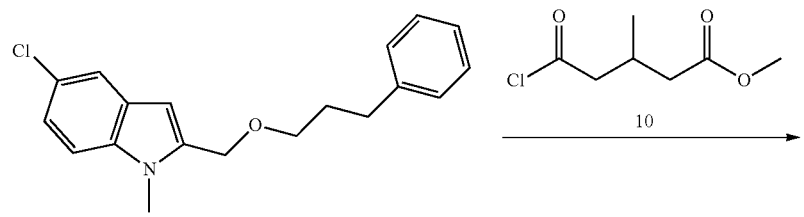

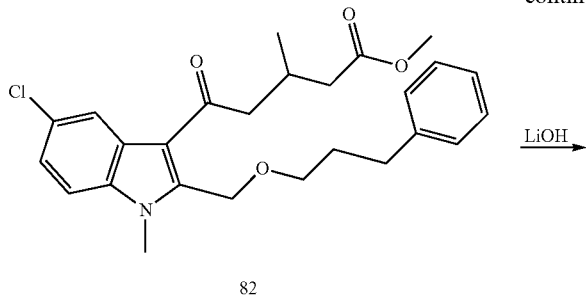

82

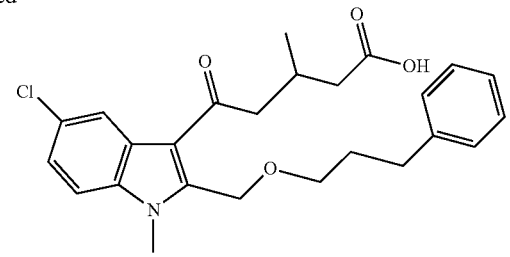

83

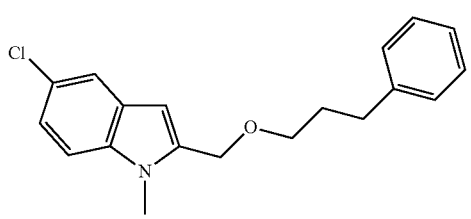 [SMILES: Cn1c(COCCCc2ccccc2)cc2cc(Cl)ccc21]

Synthesis of 5-chloro-1-methyl-2-((3-phenyl-propoxy)methyl)-1H-indole (81)

To a stirred solution of ethyl (5-chloro-1-methyl-1H-indol-2-yl)methanol (300 mg, 1.4 mmol) in DMF (10 ml) was added NaH (0.167 g, 7 mmol, 60% dispersion in mineral oil) and DMAP (0.205 g, 1.7 mmol) at 0° C., and stirred at rt for 30 min followed by the addition of (3-bromopropyl)benzene (0.28 g, 1.4 mmol). After stirred at room temperature for about 4 h, the reaction mixture was quenched with water at 0° C. and extracted with EtOAc. The organic layers were combined, washes with brine, and dried over $Na_2SO_4$. The solvent were evaporated under reduced pressure and the crude was purified using silica gel chromatography (40% EtOAc/hexane) to afford 5-chloro-1-methyl-2-((3-phenylpropoxy)methyl)-1H-indole (320 mg, 73%). $^1$H NMR (400 MHz, $CDCl_3$): δ 7.53 (d, J=1.6 Hz, 1H), 7.24-7.20 (m, 3H), 7.19-7.14 (m, 2H), 7.12 (d, J=6.9 Hz, 2H), 6.39 (s, 1H), 4.62 (s, 2H), 3.77 (s, 3H), 3.47 (t, J=6.3 Hz, 2H), 2.69-2.60 (m, 2H), 1.90 (tt, J=12.8, 6.4 Hz, 2H). $^{13}$C NMR: 141.75, 137.46, 136.53, 128.42, 128.35, 128.13, 125.85, 125.11, 122.09, 120.04, 110.14, 102.27, 69.07, 64.83, 32.38, 31.31, 30.10.

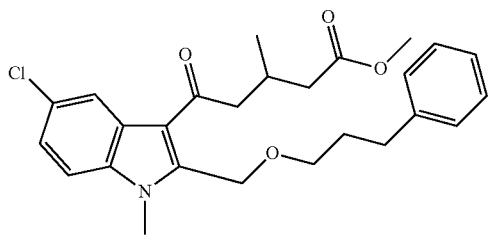 [SMILES: COC(=O)CC(C)CC(=O)c1c(COCCCc2ccccc2)n(C)c2ccc(Cl)cc12]

Synthesis of methyl methyl 5-(5-chloro-1-methyl-2-((3-phenylpropoxy)methyl)-1H-indol-3-yl)-3-methyl-5-oxopentanoate (82)

To a stirred solution of 5-methoxy-3-methyl-5-oxopentanoic acid (500 mg, 3 mmol) in dichloromethane (5 ml) was added one drop of DMF followed by 3.1 ml of oxalyl chloride solution (2.0 M in dichloromethane, 6.2 mmol) at 0° C. The reaction mixture was stirred for 4 h in rt and the crude was evaporated under reduced pressure to obtain methyl 5-chloro-3-methyl-5-oxopentanoate. To a stirred solution of 5-chloro-1-methyl-2-((3-phenylpropoxy)methyl)-1H-indole (300 mg, 0.95 mmol) in dichloromethane was added $Me_2AlCl$ (1.0 M in hexane, 1 mL, 1 mmol) at 0° C. After stirred at rt for 1 h, the reaction was quenched with water, extracted with EtOAc, the organic layers were combined, washed with brine and dried over $Na_2SO_4$. The solvents were evaporated under reduced pressure and the crude was purified by silica gel chromatography using 30% EtOAc/Hex as eluent to afford 5-(5-chloro-1-methyl-2-((3-phenylpropoxy)methyl)-1H-indol-3-yl)-3-methyl-5-oxopentanoate (240 mg, 57%). $^1$H NMR (400 MHz, $CDCl_3$): δ 7.94 (d, J=1.3 Hz, 1H), 7.30 (m, 2H), 7.23 (m, 2H), 7.16 (d, J=7.2 Hz, 1H), 7.11 (d, J=7.0 Hz, 2H), 5.11 (s, 2H), 3.84 (s, 3H), 3.68 (s, 3H), 3.55 (t, J=6.3 Hz, 2H), 3.06 (dd, J=16.3, 6.4 Hz, 1H), 2.92 (dd, J=16.3, 7.1 Hz, 1H), 2.74 (dq, J=13.3, 6.7 Hz, 1H), 2.69-2.61 (m, 2H), 2.51 (dd, J=15.0, 6.0 Hz, 1H), 2.31 (dd, J=15.0, 7.6 Hz, 1H), 1.96-1.84 (m, 2H), 1.08 (d, J=6.7 Hz, 3H). $^{13}$C NMR: 195.79, 173.09, 143.48, 141.67, 135.54, 128.37, 128.33, 128.00, 126.30, 125.84, 123.30, 120.96, 115.41, 110.96, 69.82, 62.17, 51.49, 49.49, 41.02, 32.36, 31.35, 30.60, 26.57, 20.28.

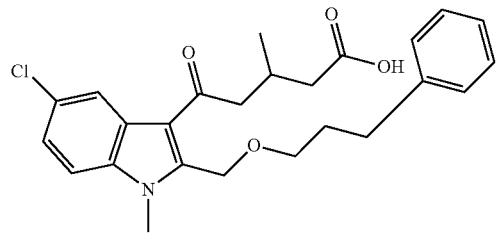 [SMILES: CC(CC(=O)O)CC(=O)c1c(COCCCc2ccccc2)n(C)c2ccc(Cl)cc12]

Synthesis of 5-(5-chloro-1-methyl-2-((3-phenyl-propoxy)methyl)-1H-indol-3-yl)-3-methyl-5-oxopentanoic acid (83)

To a stirred solution of 5-(5-chloro-1-methyl-2-((3-phenylpropoxy)methyl)-1H-indol-3-yl)-3-methyl-5-oxopentanoate (120 mg, 0.34 mmol) in $THF/H_2O$ (4/1, 1 ml) was added LiOH (41 mg, 1.7 mmol). The reaction mixture was stirred for 16 h in rt and the THF was evaporated under reduced pressure. The aqueous layer was acidified with 4 N HCl and then extracted with EtOAc, the organic layers were combined, washed with brine and dried over $Na_2SO_4$. The solvents were evaporated under reduced pressure to afford 5-(5-chloro-1-methyl-2-((3-phenylpropoxy)methyl)-1H-indol-3-yl)-3-methyl-5-oxopentanoic acid (104 mg, 69%). $^1$H NMR (400 MHz, $CDCl_3$): δ 7.94 (d, J=1.2 Hz, 1H), 7.32-7.28 (m, 2H), 7.24-7.10 (m, 5H), 5.10 (q, J=12.8 Hz, 2H), 3.84 (s, 3H), 3.56 (t, J=6.3 Hz, 2H), 3.07 (dd, J=16.1, 7.0 Hz, 1H), 2.97 (dd, J=16.1, 6.5 Hz, 1H), 2.77-2.70 (m, 1H), 2.65 (t, J=7.4 Hz, 2H), 2.54 (dd, J=15.2, 5.8 Hz, 1H), 2.36 (dd, J=15.2, 7.2 Hz, 1H), 1.94-1.87 (m, 2H), 1.13 (d, J 6.7 Hz, 3H). $^{13}$C NMR: 196.04, 176.97, 143.67, 141.65, 135.55, 128.38, 128.35, 128.14, 126.31, 125.85, 123.39, 120.95, 115.30, 111.02, 69.88, 62.16, 49.26, 40.76, 32.34, 31.32, 30.63, 26.51, 20.37.
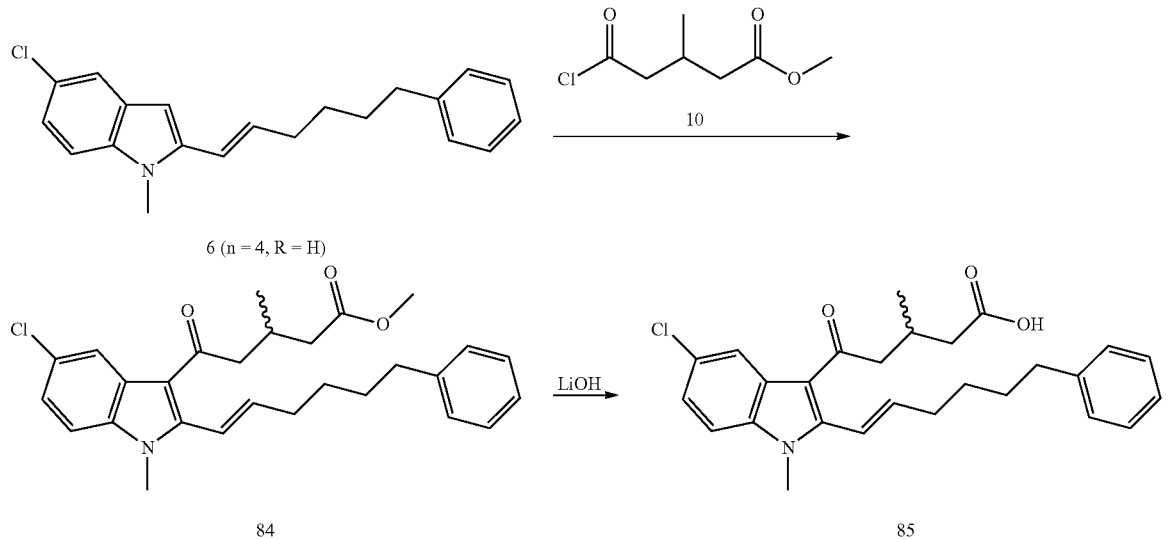
Scheme 9. Synthesis of 85
(E)-5-(5-chloro-1-methyl-2-(6-phenylhex-1-en-1-yl)-1H-indol-3-yl)-3-methyl-5-oxopentanoic acid (85)
$^1$H NMR (400 MHz, CDCl$_3$): δ 8.22 (s, 1H), 7.29 (d, J=8 Hz, 2H), 7.24-7.17 (m, 5H), 6.70 (d, J=16 Hz, 1H), 6.05 (dt, J=16 Hz, 1H), 3.68 (s, 3H), 2.88 (d, J=7 Hz, 2H), 2.72-2.58 (m, 3H), 2.48 (dd, J=15.0, 5.7 Hz, 1H), 2.40 (dd, J=7 Hz, 2H), 2.30 (dd, J=7 Hz, 1H), 1.79-1.68 (m, 2H), 1.60 (dt, J=15, 7.5 Hz, 2H), 1.06 (d, J=7 Hz, 3H). $^{13}$C NMR: 196.01, 176.85, 145.02, 142.90, 142.22, 135.64, 128.40, 128.37, 128.30, 127.31, 125.84, 123.37, 121.48, 119.93, 114.27, 110.70, 48.32, 40.87, 35.72, 33.48, 31.31, 31.13, 28.34, 27.08, 20.38.
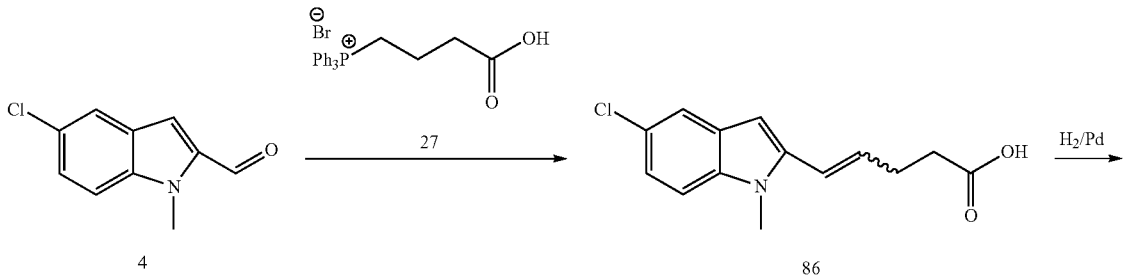
Scheme 10. Synthesis of 5-alkene compound (Racemic 94)
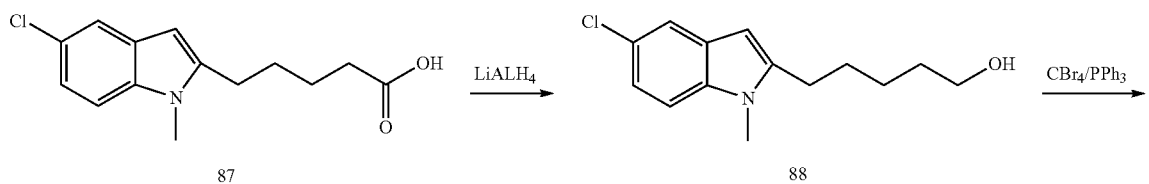

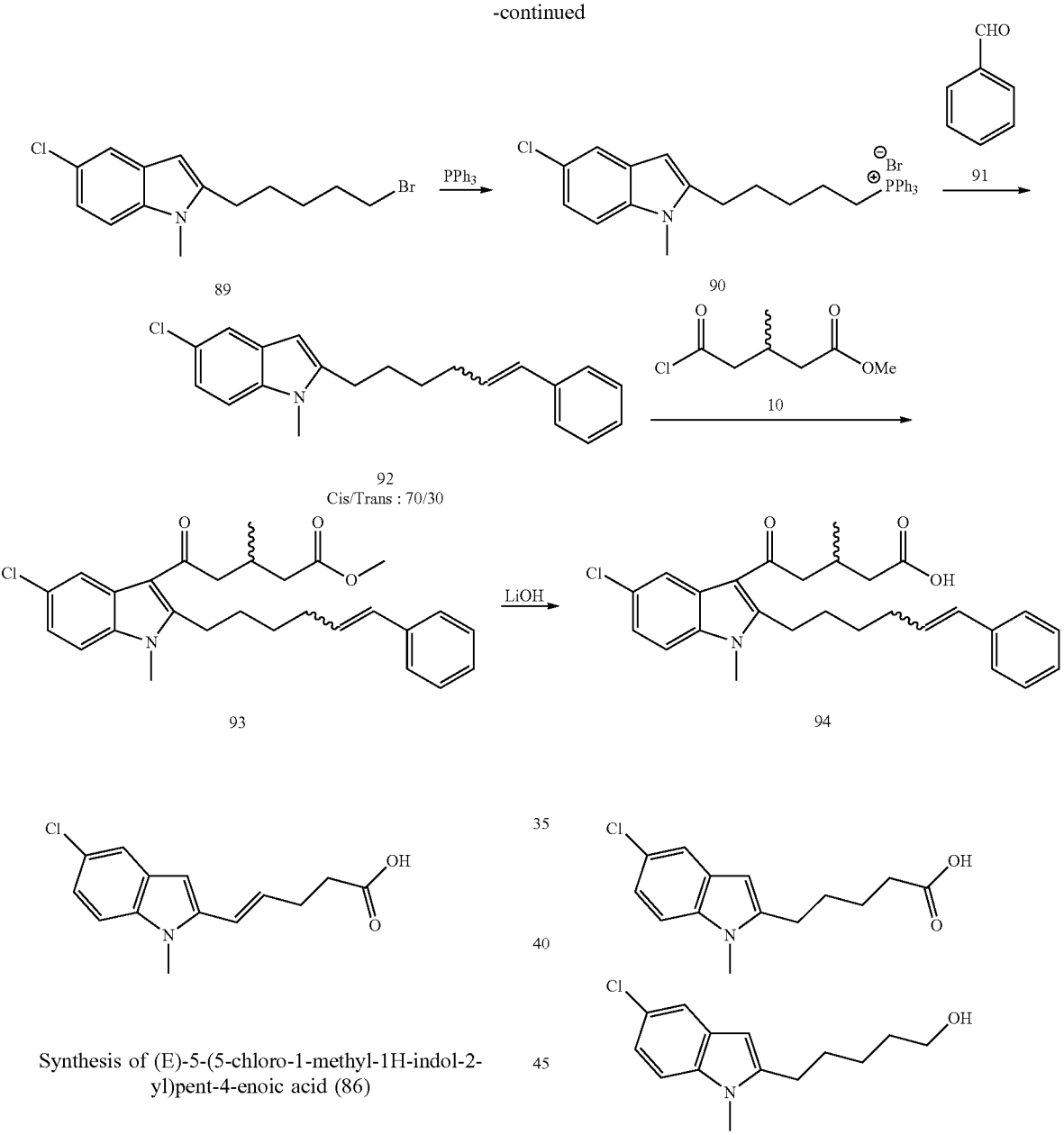

Synthesis of (E)-5-(5-chloro-1-methyl-1H-indol-2-yl)pent-4-enoic acid (86)

To a suspension of 27 (12 g, 27.9 mmol) in THF (10 mL) was added t-BuOK (1.0 M in THF, 55 mL, 55 mmol) at 0° C. The mixture was stirred for 30 min, cooled back to 0° C., and the aldehyde 4 (2 g, 10 mmol) in THF (20 ml) was added dropwise. The reaction mixture was allowed to warm to rt and stirred for 4 h. Saturated NH$_4$Cl solution was added at 0° C. and the crude was acidified to pH=3. The organic layer was extracted with EtOAc, and the combined organic layers were washed with brine, dried over Na$_2$SO$_4$ and evaporated under reduced pressure. The crude was purified by silica gel chromatography (30% EtOAc/Hexane) to afford 86 (2.4 g, 90%). $^1$H NMR (400 MHz, CDCl$_3$): δ 7.49 (d, J=1.5 Hz, 1H), 7.12 (m, 3H), 6.50 (d, J=14.0 Hz, 2H), 6.35-6.24 (m, 1H), 3.68 (s, 3H), 2.67-2.54 (m, 4H). $^{13}$C NMR: 177.77, 139.32, 132.12, 125.35, 121.60, 120.00, 119.47, 110.05, 97.87, 33.75, 33.35, 29.98, 28.26, 22.48.

Synthesis of 5-(5-chloro-1-methyl-1H-indol-2-yl)pentan-1-ol (88)

To a stirred solution of 86 (2 g, 7.6 mmol) in EtOH (15 mL) was added 10% Pd/C (0.2 g) under H$_2$ atm. The reaction mixture was stirred at rt for 8 h and then filtered. The residue was washed with EtOAc, and the combined filtrate was concentrated under reduced pressure to afford 87 (2 g, 99%). The crude acid 87 was used further without any purification. To a stirred solution of 87 (1.1 g, 4.1 mmol) in THF (15 ml) was added LiAlH$_4$ (300 mg, 4.9 mmol) slowly at −20° C. Once the addition was complete the reaction mixture was allowed to warm to rt and stirred for 4 h. Water was added and the organic layer was dried over Na$_2$SO$_4$. The solvents were evaporated under reduced pressure to get the crude product (908 mg, 88%), which was used without any further purification. $^1$H NMR (400 MHz, CDCl$_3$): δ 7.45 (s, 1H), 7.08 (m, 2H), 6.16 (s, 1H), 3.63 (t, J=6.4 Hz, 2H), 3.58 (s, 3H), 2.69 (t, J=7.6 Hz, 2H), 1.73 (dt, J=15.2, 7.6 Hz, 2H), 1.61 (dt, J=13.6, 6.6 Hz, 2H), 1.55-1.42 (m, 2H). $^{13}$C NMR: 142.61, 135.73, 128.82, 124.79, 120.59, 119.02, 109.65, 98.40, 62.70, 32.46, 29.53, 28.21, 26.77, 25.55.

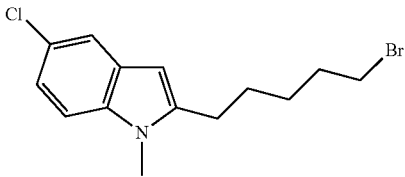 [SMILES: Cn1c(CCCCCBr)cc2cc(Cl)ccc21]

Synthesis of 2-(5-bromopentyl)-5-chloro-1-methyl-1H-indole (89)

To a stirred solution of 88 (500 mg, 2.0 mmol) in dichloromethane (10 ml) was added PPh$_3$ (522 mg, 2.0 mmol) followed by CBr$_4$ (331.65 mg, 1.8 mmol) at 0° C. The reaction mixture was allowed to warm to rt and stirred for 20 min. The solvents were evaporated under reduced pressure and the crude was purified by silica gel chromatography (5% EtOAc/Hexane) to afford 89 (570 mg, 91%). $^1$H NMR (400 MHz, CDCl$_3$): δ 7.47 (d, J=1.3 Hz, 1H), 7.15 (d, J=8.6 Hz, 1H), 7.08 (dd, J=8.6, 1.6 Hz, 1H), 6.18 (s, 1H), 3.63 (s, 3H), 3.42 (t, J=6.7 Hz, 2H), 2.73 (t, J=7.6 Hz, 2H), 2.01-1.87 (m, 2H), 1.80-1.69 (m, 2H), 1.64-1.54 (m, 2H). $^{13}$C NMR: 142.26, 135.75, 128.80, 124.90, 120.72, 119.10, 109.65, 98.49, 33.59, 32.51, 29.59, 27.91, 27.58, 26.67.

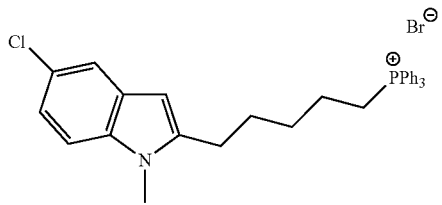

Synthesis of (5-(5-chloro-1-methyl-1H-indol-2-yl)pentyl)triphenylphosphonium bromide (90)

To a stirred solution of 89 (560 mg, 1.8 mmol) in acetonitrile (10 ml) was added PPh$_3$ (562 mg, 2.1 mmol). The reaction mixture was reflux at 65° C. for 2 days. The solvent was evaporated under reduced pressure and the crude was purified by silica gel chromatography (10% MeOH/dichloromethane) to afford 90 (929 mg, 90%). $^1$H NMR (400 MHz, CDCl$_3$): δ 7.86-7.61 (m, 15H), 7.37 (d, J=1.6 Hz, 1H), 7.11 (d, J=8.7 Hz, 1H), 7.02 (dd, J=8.6, 1.9 Hz, 1H), 6.06 (s, 1H), 3.72 (dd, J=15.8, 12.8 Hz, 2H), 3.59 (s, 3H), 2.69 (t, J=7.2 Hz, 2H), 1.85-1.57 (m, 6H). $^{13}$C NMR: 142.51, 135.71, 135.08, 133.60, 130.53, 128.74, 124.65, 120.51, 118.75, 117.77, 109.81, 98.44, 30.06, 29.86, 28.11, 26.48, 22.94, 22.48.

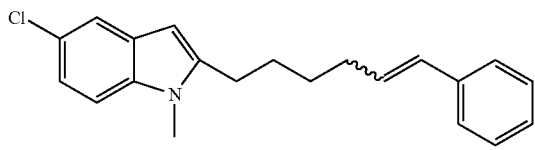 [SMILES: Cn1c(CCCCC=Cc2ccccc2)cc2cc(Cl)ccc21]

Synthesis of (Z)-5-chloro-1-methyl-2-(6-phenylhex-5-en-1-yl)-1H-indole (92)

To a suspension of 90 (2 g, 3.5 mmol) in THF (1 mL) was added LiHMDS (1.0 M in THF, 5.6 mL, 5.6 mmol) at −78° C. The mixture was stirred for 30 min, cooled back to −78° C., and the aldehyde 91 (0.2 g, 1.9 mmol) in THF (2 ml) was added dropwise. The reaction mixture was allowed to warm to rt and stirred for 4 h. Saturated NH$_4$Cl solution was added at −78° C. The organic layer was extracted with EtOAc, and the combined organic layers were washed with brine, dried over Na$_2$SO$_4$ and evaporated under reduced pressure. The crude was purified by silica gel chromatography (20% EtOAc/Hexane) to afford 92 (Cis/Trans:70/30) (0.18 g, 30%). $^1$H NMR (400 MHz, CDCl$_3$): δ 7.38 (s, 1H), 7.26-7.12 (m, 5H), 7.06-6.98 (m, 2H), 6.37-6.30 (m, 1H), 6.07 (s, 1H), 5.60-5.54 (m, 1H), 3.49 (s, 3H), 2.59 (t, J=7.4 Hz, 2H), 2.35-2.29 (m, 2H), 1.73-1.62 (m, 2H), 1.57-1.45 (m, 2H). $^{13}$C NMR: 137.65, 137.75, 130.32, 131.95, 128.74, 128.51, 128.15, 126.93, 125.93, 122.03, 117.07, 32.65, 30.26, 29.71, 28.69, 28.31.

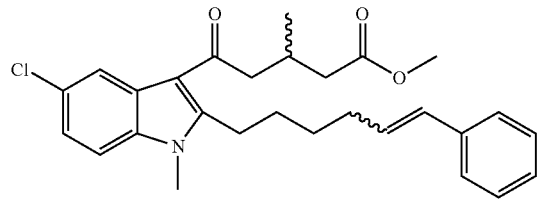 [SMILES: COC(=O)CC(C)CC(=O)c1c(CCCCC=Cc2ccccc2)n(C)c2ccc(Cl)cc12]

Synthesis of 5-[5-Chloro-1-methyl-2-(6-phenyl-hex-5-enyl)-1H-indol-3-yl]-3-methyl-5-oxopentanoic acid methyl ester (93)

To a stirred solution of 5-methoxy-3-methyl-5-oxopentanoic acid (100 mg, 0.624 mmol) in dichloromethane (10 ml) was added one drop of DMF followed by 0.62 ml of oxalyl chloride solution (2.0 M in dichloromethane, 1.24 mmol) at 0° C. The reaction mixture was stirred for 4 h in rt and the crude was evaporated under reduced pressure to obtain 10. To a stirred solution of 92 (150 mg, 0.463 mmol) in dichloromethane was added Me$_2$AlCl (1.0 M in hexane, 0.926 mL, 0.926 mmol) at 0° C. After 45 min, compound 10 (98 mg, 0.55 mmol) in CH$_2$Cl$_2$ (10 mL) was added dropwise at rt and the reaction mixture stirred for 1 h. The reaction was quenched by adding water and extracted with EtOAc. The organic layers were combined, washed with brine and dried over Na$_2$SO$_4$. The solvents were evaporated under reduced pressure and the crude was purified by silica gel chromatography using 15% EtOAc/Hex as eluent to afford 93 (151 mg, 70%). $^1$H NMR (400 MHz, CDCl$_3$): δ 7.87 (d, J=0.92 Hz, 1H), 7.33-7.18 (m, 7H), 6.42 (d, J=11.68 Hz, 1H), 5.67-5.61 (m, 1H), 3.67 (s, 3H), 3.64 (s, 3H), 3.15 (t, J=7.24 Hz, 2H), 3.02 (dd, J=6.4, 16.12 Hz, 1H), 2.88 (dd, J=7.0, 16.16 Hz, 1H), 2.78-2.70 (m, 1H), 2.51 (dd, J=5.96, 14.92 Hz, 1H), 2.43-2.27 (m, 3H), 1.67-1.63 (m, 4H), 1.07 (d, J=6.72 Hz, 3H). $^{13}$C NMR: 195.11, 173.36, 150.61, 137.76, 135.27, 132.65, 130.46, 129.41, 128.92, 128.67, 128.02, 127.06, 126.73, 126.11, 122.38, 120.59, 113.46, 110.80, 51.65, 49.55, 41.30, 30.07, 29.76, 28.76, 28.40, 26.67, 26.25, 20.52.

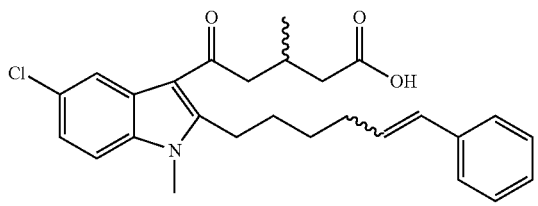 [SMILES: CC(CC(=O)O)CC(=O)c1c(CCCCC=Cc2ccccc2)n(C)c2ccc(Cl)cc12]

Synthesis of 5-[5-Chloro-1-methyl-2-(6-phenyl-hex-5-enyl)-1H-indol-3-yl]-3-methyl-5-oxopentanoic acid (94)

To a stirred solution of 93 (120 mg, 257 mmol) in THF/H$_2$O (4/1, 10 ml) was added LiOH (123 mg, 5.15 mmol). The reaction mixture was stirred for 48 h in rt and the THF was evaporated under reduced pressure. The aqueous layer was acidified with 4 N HCl and then extracted with EtOAc, the organic layers were combined, washed with brine and dried over Na$_2$SO$_4$. The solvents were evaporated under reduced pressure to afford 94 (87 mg, 75%). $^1$H NMR (400 MHz, CDCl$_3$ δ 7.87 (s, 1H), 7.32-7.16 (m, 7H), 6.45-6.40 (m, 1H), 5.66-5.60 (m, 1H), 3.63 (s, 3H), 3.14 (t, J=6.96 Hz, 2H), 3.05-2.90 (m, 2H), 2.74-2.68 (m, 1H), 2.54 (dd, J=5.64, 15.2 Hz, 1H), 2.42-2.25 (m, 3H), 1.65-1.62 (m, 4H), 1.13 (d, J=6.72 Hz, 3H). $^{13}$C NMR: 195.24, 173.48, 150.86, 137.68, 135.12, 132.43, 130.32, 129.24, 128.73, 128.14, 127.99, 126.87, 126.55, 125.92, 122.30, 120.38, 113.13, 110.67, 49.06, 40.92, 32.70, 29.86, 29.60, 28.52, 26.44, 21.06, 20.43.

Scheme 11: Synthesis of 5-(5-chloro-2-(7-(3-chlorophenyl)heptyl)-1-methyl-1H-indol-3-yl)-3-methyl-5-oxopentanoic acid

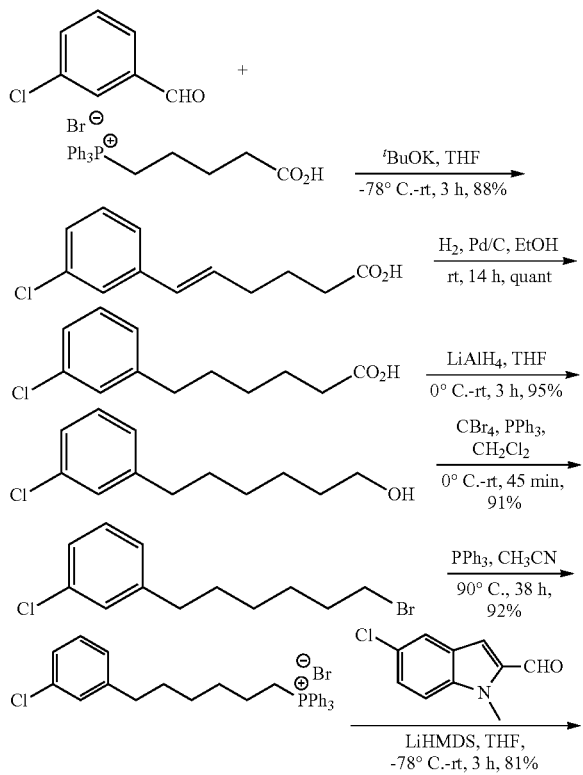

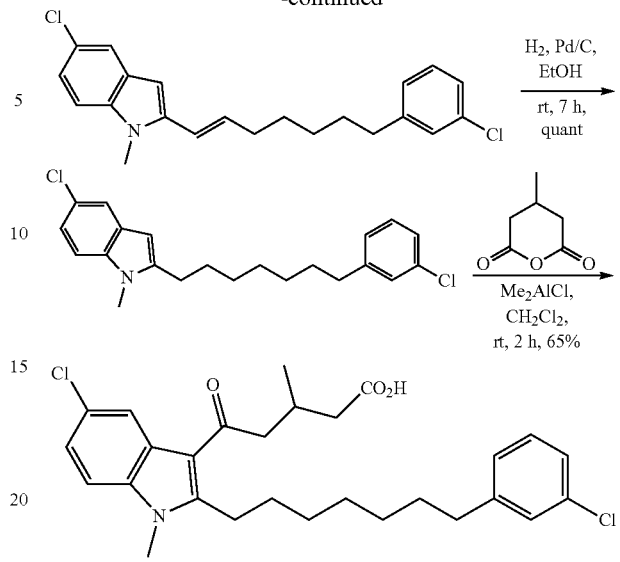

5-(5-chloro-2-(7-(3-chlorophenyl)heptyl)-1-methyl-1H-indol-3-yl)-3-methyl-5-oxopentanoic acid $^1$H NMR (400 MHz, CDCl$_3$): δ 7.88 (s, 1H), 7.24-7.13 (m, 5H), 7.04 (d, J=7.4 Hz, 1H), 3.70 (s, 3H), 3.16 (t, J=7.9 Hz, 2H), 2.99 (t, J=6.8 Hz, 2H), 2.76-2.69 (m, 1H), 2.64-2.51 (m, 3H), 2.36 (dd, J=15.1, 7.2 Hz, 1H), 1.67-1.57 (m, 4H), 1.49-1.29 (m, 6H), 1.15 (d, J=6.7 Hz, 3H). $^{13}$C NMR (CDCl$_3$): δ 195.5, 176.2, 151.2, 144.8, 135.2, 134.0, 129.5, 128.5, 128.4, 128.1, 126.6, 125.8, 122.4, 120.4, 113.0, 110.7, 49.0, 40.9, 35.6, 31.1, 29.7 (2C), 29.2, 29.1, 29.0, 26.6, 26.4, 20.6.

Evaluation of Antagonist Activity: Calcium Mobilization in Human Granulocytes

Human granulocytes (≥95% neutrophils) are prepared from whole blood using Dextran 500 to remove red blood cells, followed by centrifugation over Ficoll-Paque to remove mononuclear cells and hypotonic lysis of any remaining red blood cells. After centrifugation the granulocytes are suspended in Ca$^{++}$/Mg$^{++}$-free phosphate-buffered saline (PBS$^-$). Granulocytes (10$^7$ cells/ml) are incubated with the acetoxymethyl ester of indo-1 (1 μM) for 30 min, followed by washing twice with PBS$^-$ and resuspension in the same medium to obtain a final cell concentration of 3.22×10$^6$ cells/ml. Five minutes prior to commencing data acquisition, Ca$^{++}$ and Mg$^{++}$ are added to give final concentrations of 1.8 and 1 mM, respectively. Calcium measurements are performed at 37° C. using a spectrofluorometer equipped with a temperature-controlled cuvette holder and a magnetic stirrer. The excitation and emission wavelengths are 331 nm and 410 nm, respectively. Following stabilization of the baseline, fluorescence is measured for 1 min, prior to the addition of either vehicle or various concentrations of a potential 5-oxo-ETE antagonist. Two min later, 5-oxo-ETE (10 nM) is added, followed 1 min later by digitonin (final concentration 0.1%). Data acquisition is terminated after a further 0.5 min. F$_{max}$ is determined from fluorescence measurements after the addition of digitonin, whereas F$_{min}$ is determined after determination of autofluorescence as described in the literature. A dissociation constant of 250 nM for the indo-1/Ca$^{++}$ complex is used to calculate $[Ca^{++}]_i$. The % inhibition of 5-oxo-ETE-induced calcium mobilization by the antagonist is calculated as follows:

Inhibition (%)=(1−($Ca_{ant}$/$Ca^{++}_{veh}$))×100 where $Ca_{ant}$ is the increase in cytosolic calcium levels induced by 5-oxo-ETE (10 nM) following the addition of a potential antagonist, whereas $Ca_{veh}$ is the response induced by 5-oxo-ETE following addition of vehicle alone.

The following tables illustrates the structure and activity of certain reference compounds as well as activity for exemplary compounds of the disclosure:

TABLE 1

| Reference Compounds | Formula | IC50 (nM) |
|---|---|---|
| 12 | | 223 ± 18 (2) |
| V230 | | 6 ± 1 |
| V197 | | 20 ± 6 (5) |
| V225 | | 88 ± 26 (5) |
| Met a V230 (ω-1)OH | | 1600 ± 400 (3) |

TABLE 1-continued

| Reference Compounds | Formula | IC50 (nM) |
|---|---|---|
| Met b V230 (ω-1)oxo | [structure] | 1900 ± 500 (2) |
| V230 ω-OH | [structure] | 260 ± 30 (2) |

TABLE 2

| Compounds | Formula | IC50 (nM) |
|---|---|---|
| 15 | [structure] | 0.18 ± 0.04 (6) |
| 13 | [structure] | 38 ± 8 (3) |
| 14 | [structure] | 11 ± 1 (5) |

TABLE 2-continued

| Compounds | Formula | IC50 (nM) |
|---|---|---|
| 17 | 5-Cl, 1-methyl-2-(6-(2-chlorophenyl)hexyl)indol-3-yl ketone with 3-methyl-4-carboxybutanoyl | 0.44 ± .13 (3) |
| 18 | 5-Cl, 1-methyl-2-(6-(2-fluorophenyl)hexyl)indol-3-yl ketone with 3-methyl-4-carboxybutanoyl | 0.41 ± .07 (6) |
| 19 | 5-Cl, 1-methyl-2-(6-(2-methoxyphenyl)hexyl)indol-3-yl ketone with 3-methyl-4-carboxybutanoyl | 0.18 ± .05 (5) |
| 20 | 5-Cl, 1-methyl-2-(6-(3-chlorophenyl)hexyl)indol-3-yl ketone with 3-methyl-4-carboxybutanoyl | 0.033 ± .003 (6) |
| 21 | 5-Cl, 1-methyl-2-(6-(3-fluorophenyl)hexyl)indol-3-yl ketone with 3-methyl-4-carboxybutanoyl | 0.072 ± .007 (3) |
| 22 | 5-Cl, 1-methyl-2-(6-(3-methoxyphenyl)hexyl)indol-3-yl ketone with 3-methyl-4-carboxybutanoyl | 0.086 ± .017 (6) |

TABLE 2-continued

| Compounds | Formula | IC50 (nM) |
|---|---|---|
| 23 | | 0.63 ± .22 (3) |
| 24 | | 0.80 ± .24 (6) |
| 25 | | 0.63 ± .08 (5) |
| 39 | | 0.54 ± .12 (6) |
| 37 | | 6.5 ± 1.5 (2) |
| 38 | | 1.9 ± .3 (3) |

TABLE 2-continued

| Compounds | Formula | IC50 (nM) |
|---|---|---|
| 46 | | 0.10 ± .01 (30) |
| 47 | | 0.55 ± .19 (3) |
| 48 | | 0.27 ± .06 (5) |
| 49 | | 0.10 ± .02 (8) |
| 50 | | 0.0081 ± .0013 (5) |
| 51 | | 0.037 ± .005 (5) |

TABLE 2-continued

| Compounds | Formula | IC50 (nM) |
|---|---|---|
| 52 | | 0.051 ± .007 (4) |
| 53 | | 0.47 ± .16 (4) |
| 54 | | 0.39 ± .09 (7) |
| 55 | | n/a |
| 61 | | 23 ± 2 (3) |
| 62 | | 81 ± 34 (2) |

TABLE 2-continued

| Compounds | Formula | IC50 (nM) |
|---|---|---|
| 63 | 5-Cl, 1-methyl-indole, 2-(6-(2-fluorophenyl)hexyl), 3-[(3S)-3-methyl-4-carboxybutanoyl] | 2.9 ± .1 (2) |
| 64 | 5-Cl, 1-methyl-indole, 2-(6-(2-methoxyphenyl)hexyl), 3-[(3S)-3-methyl-4-carboxybutanoyl] | 54 ± 23 (6) |
| 65 | 5-Cl, 1-methyl-indole, 2-(6-(3-chlorophenyl)hexyl), 3-[(3S)-3-methyl-4-carboxybutanoyl] | 0.64 ± .10 (5) |
| 66 | 5-Cl, 1-methyl-indole, 2-(6-(3-fluorophenyl)hexyl), 3-[(3S)-3-methyl-4-carboxybutanoyl] | 1.8 ± .3 (5) |
| 67 | 5-Cl, 1-methyl-indole, 2-(6-(3-methoxyphenyl)hexyl), 3-[(3S)-3-methyl-4-carboxybutanoyl] | 50 ± 13 (5) |
| 68 | 5-Cl, 1-methyl-indole, 2-(6-(4-chlorophenyl)hexyl), 3-[(3S)-3-methyl-4-carboxybutanoyl] | n/a |

TABLE 2-continued
| Compounds | Formula | IC50 (nM) |
|---|---|---|
| 69 | 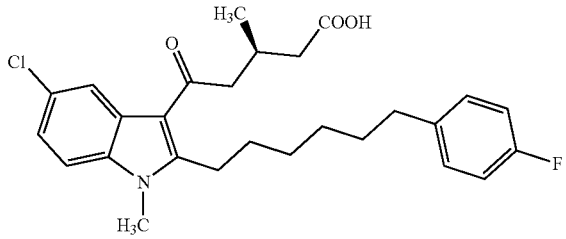 [SMILES: C[C@@H](CC(=O)O)CC(=O)c1c(CCCCCCc2ccc(F)cc2)n(C)c2ccc(Cl)cc12] | 4.45 ± 1.05 (2) |
| 70 | 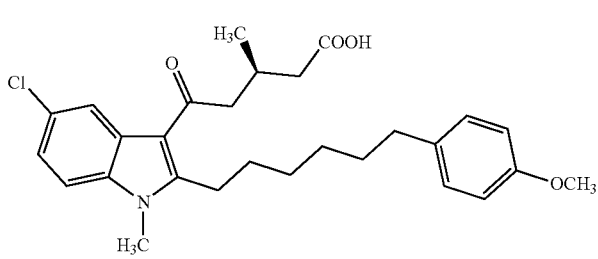 [SMILES: COc1ccc(CCCCCCc2c(C(=O)C[C@@H](C)CC(=O)O)c3cc(Cl)ccc3n2C)cc1] | n/a |
| 83 | 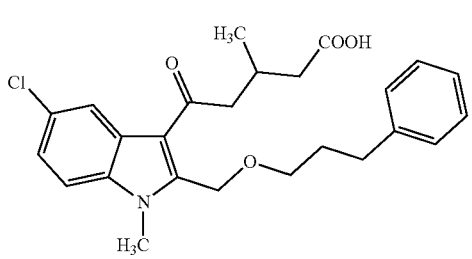 [SMILES: CC(CC(=O)O)CC(=O)c1c(COCCCc2ccccc2)n(C)c2ccc(Cl)cc12] | 0.7 (1) |
| 85 | 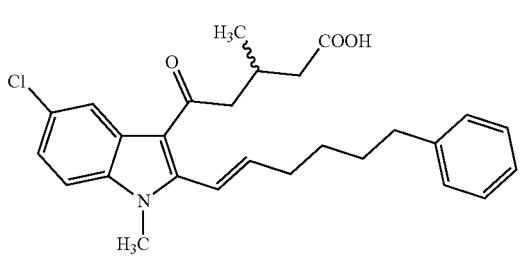 [SMILES: CC(CC(=O)O)CC(=O)c1c(/C=C/CCCCc2ccccc2)n(C)c2ccc(Cl)cc12] | 1.93 ± 0.60 (3) |
| 94 | 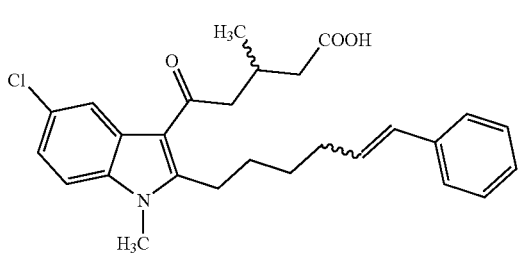 [SMILES: CC(CC(=O)O)CC(=O)c1c(CCCCC=Cc2ccccc2)n(C)c2ccc(Cl)cc12] | 0.65 ± 0.36 (2) |
| 95 | 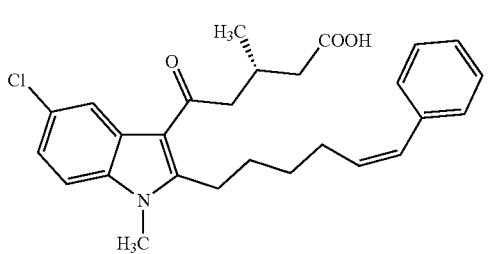 [SMILES: C[C@H](CC(=O)O)CC(=O)c1c(CCCC/C=C\c2ccccc2)n(C)c2ccc(Cl)cc12] | 0.62 ± 0.29 (3) |

TABLE 2-continued

| Compounds | Formula | IC50 (nM) |
|---|---|---|
| 96 | | 5.5 (1) |
| 97 | | 0.071 ± 0.024 (3) |
| 98 | | 1.1 ± 0.19 (3) |
| 159 | | 0.095 ± 3 (2) |

Measurement of Antagonist Concentrations in Blood Following Oral Administration

Antagonists dissolved in ethanol (5 to 75 mg/ml) and added to 20 mM NaHCO3 pH 8.0. The resulting suspension (7 to 13 ml containing 10% ethanol) was administered by gavage (between 1 and 30 mg/kg) to cynomolgous monkeys (3 to 4 kg body weight). After different times (between 0.5 and 24 h as well as just prior to administration of antagonist) blood samples (1-2 ml) were taken and centrifuged to obtain plasma, which was frozen and transported to the laboratory as soon as the experiment was complete. Upon arrival at the laboratory, the plasma samples were thawed and the internal standards (1.5 µg), along with 2 volumes of MeOH, were added, the mixture vortexed, and then stored at −80° C. until analysis. The internal standards were structural analogs containing different numbers of methylene groups. Prior to analysis the plasma samples were warmed to room temperature, the above plasma samples containing MeOH were centrifuged and water was added to the supernatant to give a final concentration of 30%. The samples were then applied to a C18 SepPak cartridge (Waters Associates) that had previously been washed with MeOH followed by water (Powell, W. S., *Prostaglandins*, 1980. 20: p. 947-957). The extracts were analyzed by reversed-phase HPLC combined with automated precolumn extraction (Powell, W. S., *Anal. Biochem.*, 1987. 164: p. 117-131). The stationary phase for the separation was a Novapak C18 column (4 µm particle size; 3.9×150 mm). The amounts of antagonists were determined on the basis of UV absorbance by comparing the peak area for the antagonist in question with that for the corresponding internal standard and correcting for any difference in extinction coefficient.

Metabolism of OXE Antagonists by Monkey Microsomes

Microsomes (catalog number MKMC-PL) from cynomolgous monkey liver were obtained from Life Technologies. Antagonists (100 µM) were incubated for various times with liver microsomes (0.5 mg protein/ml) in PBS in the presence of NADPH (2 mM). After various times aliquots (0.1 ml) were removed and placed in a tube containing 0.36 ml ice-cold methanol. After addition of 0.74 ml of water along with 1 µg of an appropriate internal standard the samples were stored at −80° C. until analysis by reversed-phase HPLC.

Chiral HPLC

S- and R-enantiomers of OXE receptor antagonists were separated using a Lux Cellulose-1 column (5 µm particle size; 4.6×250 mm; Phenomenex) using isocratic elution with a mobile phase containing hexane, 0.1% acetic acid, and between 0.5 and 2.5% MeOH.

Discussion

Compound V230 was previously described and the disclosed IC50 was 26±4 nM, A synthetic method to prepare the S- and R-enantiomers of compound V230 was also reported and the respective activities for the S and R enantiomers were found to be about 6±1 and 2730±960 nM.

It was now surprisingly found that the corresponding racemic compound 15 as described herein had an IC50 of 0.18 nM and the (S) enantiomer displayed an IC50 of 0.10 nM. Certain compounds described herein displayed potencies in the picomolar (pM) range (i.e. concentration of $10^{-12}$M), such as (racemic) m-chlorophenyl compound 20 (about 33 pM), (racemic) m-fluorophenyl compound 21 (about 72 pM), (racemic) m-methoxyphenyl compound 22 (about 86 pM) and the (S) enantiomer compound 50 (about 8 pM).

In order to develop a compound as potential drug, it is desired to have an acceptable PK profile. For example, it was found that for compounds having a methyl group in the 3-position of the acyl chain (e.g. see compound V230 above), a major metabolic pathway involved ω-oxidation of the hexyl side chain. To reduce susceptibility to ω-oxidation methyl groups in the ω-1 (compound V197) and ω-2 (compound V225) positions of the hexyl side chain were added (see table above). The isoheptyl compound V197 has an IC50 of 20 nM, similar to those of racemic compound V230, whereas compound V225 was somewhat less potent.

To examine the PK profiles of compounds V197 and V230 these compounds were administered to cynomolgus monkeys by oral gavage at a dose of 30 mg/kg. Plasma levels were measured following solid-phase extraction by reversed-phase high performance liquid chromatography (HPLC) after 0.5, 1, 2, 4, 8, 18, and 24 h using appropriate internal standards.

The two compounds appeared rapidly in the blood and reached high levels by 30 min (FIGS. 1A and 1B). However, polar metabolites were detected at all time points investigated, including the 4 h time points shown in FIGS. 1C and 1D, and their concentrations exceeded those of the parent compound at later time points (FIGS. 1A and 1B).

Figure 2:
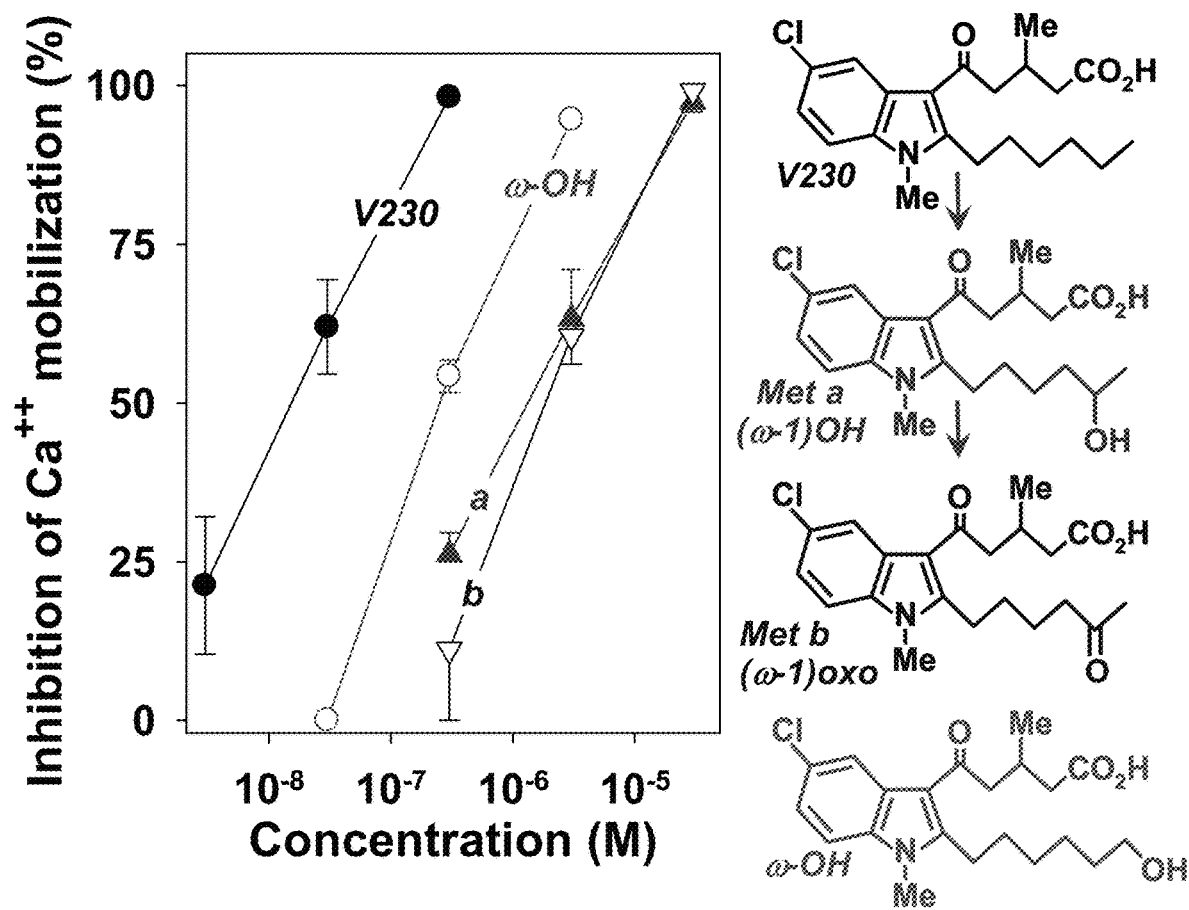
FIG. 2 shows concentration-response curves for the major plasma and microsomal metabolites of reference compound.

Potential metabolites of compound V230 were chemically synthesized and compared to those isolated from plasma. The major plasma metabolite of compound V230 was found to be the ω-1 hydroxy product along with smaller amounts of the corresponding ω-1 oxo compound (see table above). Not only was it observed that the metabolite concentrations exceeded those of the parent compound, but also both of these metabolites were about 100 times less potent than compound V230 in blocking 5-oxo-ETE-induced calcium mobilization in neutrophils (See FIG. 2).

Therefore, although compounds V230 and V197 rapidly reached high peak levels in blood following oral administration, they were converted to polar metabolites with considerably lower antagonist potencies, and the plasma levels dropped quite rapidly after 1 h, which would limit their effectiveness in vivo. As such, the potency of the compound (i.e. V230) could be offset to some extent by its relatively rapid rate of metabolism. Also, attempts to reduce metabolism by the addition of a methyl group in the ω-1 position of the hexyl side chain were not successful, as the PK profile of the resulting compound (V197) was inferior to that of compound V230.

Applicant has surprisingly found that replacement of the chain at C-2 of the indole (e.g. the hexyl groups of compound V230) by a phenyl group separated from the indole structure by a suitable spacer provides at least one of an increased potency, reduced susceptibility to metabolism and/or a more desirable PK profile.

It was observed that the spacer required a certain length. Insertion of a 3-carbon spacer between the phenyl group and the indole (reference compound 12) reduced potency by about 8-fold compared to V230. However, increasing the length of the spacer to 4 or more carbons (e.g. compounds 13 to 15), or equivalent number of a combination of unsaturated/saturated carbon or non-carbon atoms, provided acceptable potencies.

Compound 46 was incubated for up to 4 h with monkey liver microsomes in the presence of NADPH (See FIG. 3). One major metabolite was observed, along with minor products (FIG. 3B). In contrast, the extent of metabolism was much greater for compound V230 (FIG. 3A). The time courses revealed that by 4 h the ratio of unmetabolized to metabolized 46 was about 2:1 (FIG. 3D), whereas the corresponding ratio for compound V230 was 0.5:1 (FIG. 3C), a difference of 4-fold in favor of 46.

Compound 46 was administered at a dose of 30 mg/kg to monkeys by oral gavage. Plasma levels were measured by HPLC and it was observed that high levels of compound 46 along with smaller amounts of a single major metabolite (46-M—see table 3 below) were observed in plasma after 8 h (FIG. 4B). The extent of metabolism of V230 (FIG. 4A), was much greater at this time point. The pharmacokinetics of compounds 46 and V230 over 24 h are compared in FIG. 4C. The two compounds reached similar peak levels after 0.5 to 1 h, but in contrast to the rapid decline observed for compound V230, the levels of 46 fell much more slowly and were at least 10 times higher at later time points. The levels of compound 46M, the major metabolite of 46, rose more slowly to reach maximal levels by 8-12 h, followed by a modest decline by 24 h.

Figure 4E:
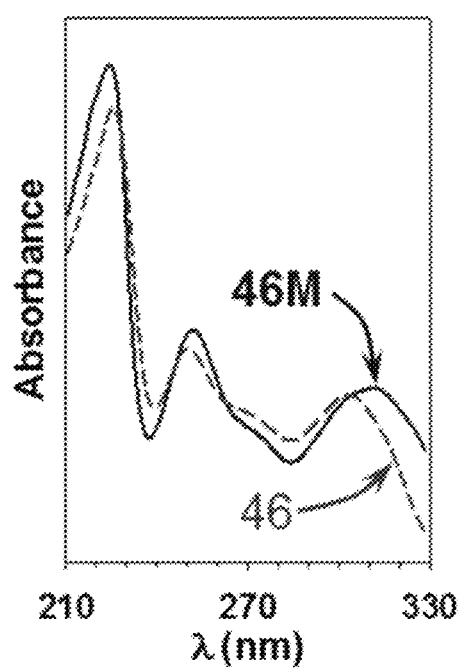
FIG. 4E is the UV spectrum of compounds of the present disclosure.
Figure 4F:
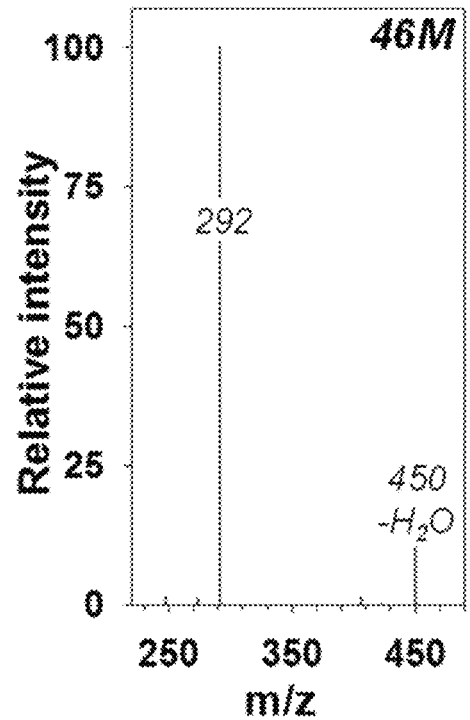
FIG. 4F is the mass spectrum of a compound of the present disclosure.
Figure 4G:
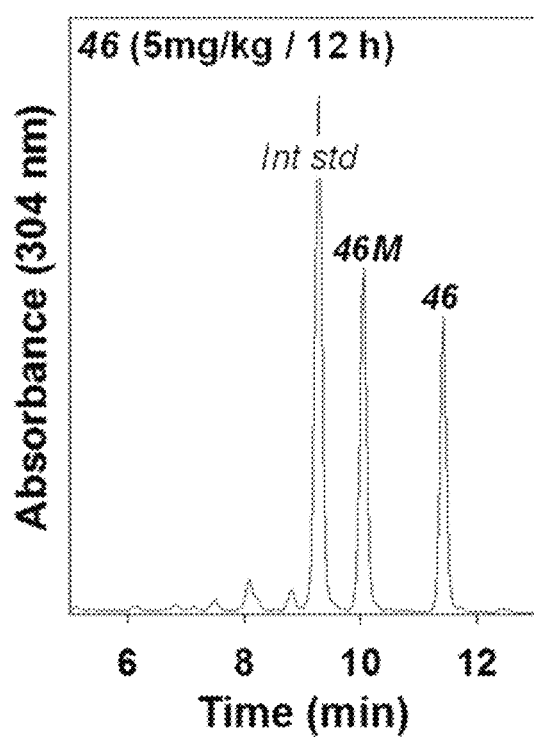
FIG. 4G is the HPLC traces showing a compound described herein isolated from plasma after administration to monkey.

Furthermore, compound 46M was purified from the plasma of monkeys that received 46 under the following conditions:

Stationary phase: Novapak C18 (4 µm; 150×3.9 mm; Waters)
Mobile phase: 70-100% MeOH (0.02% HOAc)/15 min
F=1 ml/min; T=30C and the Internal standard is compound 13. (See FIG. 4G)
Compound 46M was surprisingly found to have an IC50 of just under 1 nM in inhibiting 5-oxo-ETE-induced calcium mobilization (FIG. 4D). Compound 46M is in itself inhibiting 5-oxo-ETE-induced calcium mobilization or could also contribute substantially to the inhibition of OXE receptor signaling following administration of compound 46, especially at longer time points. Compound 46M was identified by its UV spectrum (FIG. 4E) and mass spectrum (FIG. 4F) under the following conditions:
Equipment: LTQ Orbitrap Velos; Electrospray ionization in negative ion mode
MS2 (collision-induced dissociation of M-H ion (m/z 468.19)

Racemic compound 15 was administered at a dose of 30 mg/kg (FIG. 5A) and compared to an identical dose of compound 46 (i.e. S-15). Although the peak level of racemic compound 15 was similar to that of compound 46, the levels of the racemic compound declined much more slowly than the S-enantiomer, suggesting that there is a difference in the rates of clearance of the S and R enantiomers. The material in the peak for compound 15 was collected following reversed-phase HPLC and the R and S enantiomers were separated by chiral HPLC. As shown in FIG. 5B, the peak levels of the R-enantiomer of compound 15 were higher than those of the S-enantiomer and dropped much more slowly. The material in the peak corresponding to the major metabolite of compound 15 (i.e. 15-M) was also collected following reversed-phase HPLC, and then subjected to chiral HPLC. The R-enantiomer of compound 15-M also persisted much longer than the S-enantiomer (FIG. 5C). Therefore it is possible that R-enantiomers could also prove to be useful clinically because of their persistence in the circulation.

The PK profiles of the synthetic S-enantiomers of o-methoxyphenyl (49) and p-fluorophenyl (54) antagonists, were investigated by administration by oral gavage at a dose of 5 mg/kg (FIG. 6). The plasma levels of the compounds were similar to those of 46 over a period of 24 hours.

Also, a single major metabolite was observed for each of the above two compounds (FIG. 7 panels A and B). Following oral administration of the parent compound, compounds 49M and 54M were purified from plasma by HPLC under the following conditions:
Stationary phase: Kinetex C18 (2.6 mm; 4.6×100 mm; Phenomenex)
Mobile phase: 38 to 65% MeCN (0.02% HOAc)/35 min
F=1 ml/min; T=30 C; Internal standard is compound 14.

Figures 7A, 7B, 7C, 7D:
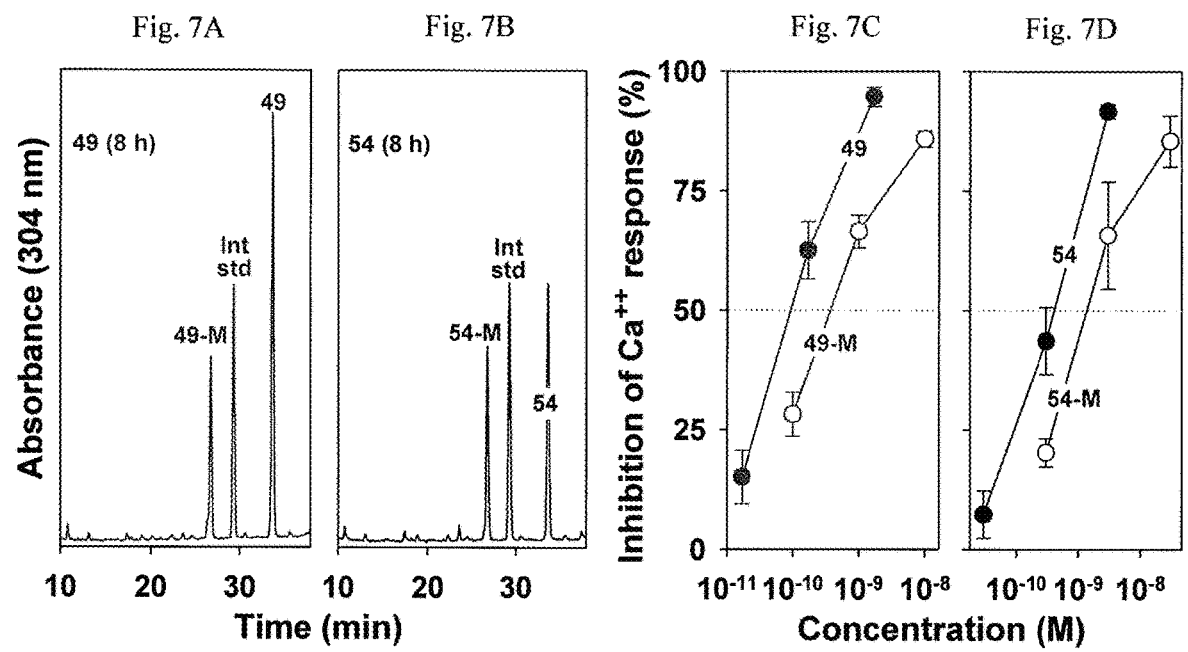
FIGS. 7A and 7B represent HPLC traces showing compounds described herein isolated from plasma after administration to monkeys.
FIGS. 7C and 7D are OXE antagonistic activity curves against the concentration of compounds of the present disclosure.

Both of compounds 49M and 54M are antagonists (49M; FIG. 7C) and (54M; FIG. 7D).

Figures 8A, 8B:
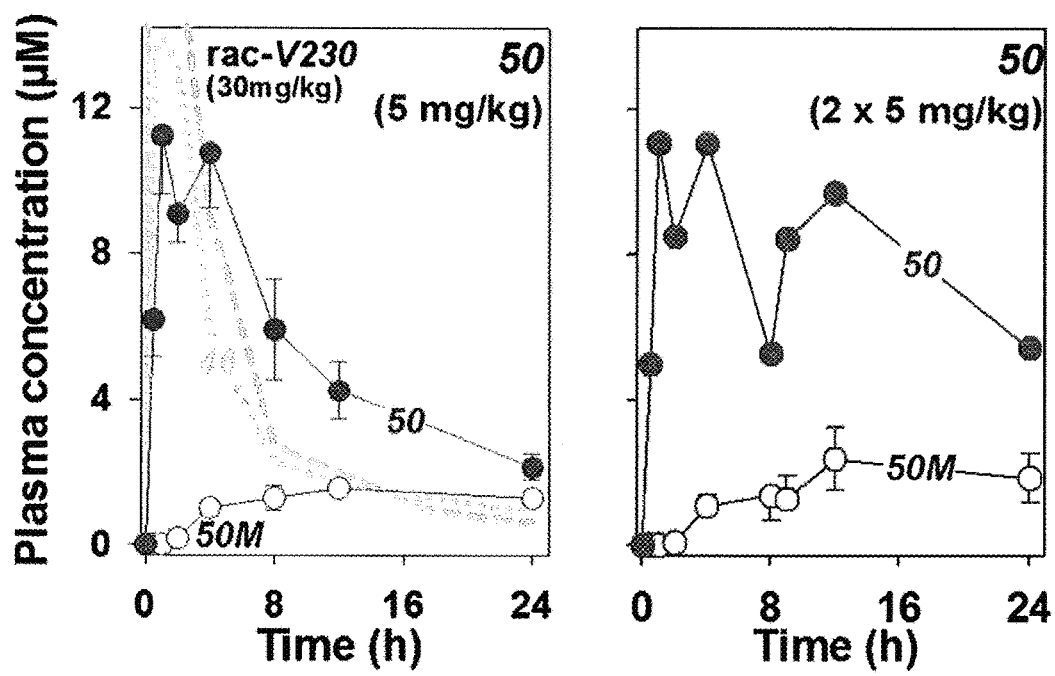
FIG. 8A is the plasma level of compound 50 administered to cynomolgus monkeys at a dose of 5 mg/kg.
FIG. 8B is the plasma level of compound 50 administered to cynomolgus monkeys at a dose of 2×5 mg/kg.

Compound 50 was administered to cynomolgus monkeys at a dose of either 5 mg/kg (FIG. 8A) or 2×5 mg/kg (at 0 h and 8 h; FIG. 8B). Blood samples (2 ml) were centrifuged immediately to obtain plasma. The plasma concentrations of compound 50 were measured by HPLC.

Figure 9A:
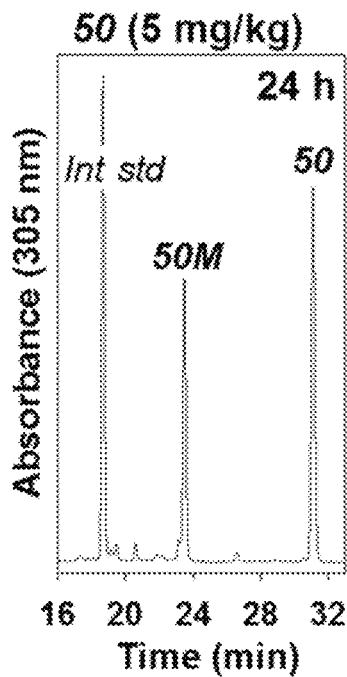
FIG. 9A is an HPLC trace showing compounds 50 and 50M obtained from plasma after administration of 50.

Compound 50 is converted to a single polar metabolite (compound 50M) (see table 3 below) which was purified from plasma by HPLC under the following conditions:
Stationary phase: Kinetex C18 (2.6 mm; 4.6×100 mm; Phenomenex)
Mobile phase: 38 to 65% MeCN (0.02% HOAc)/35 min
F=1 ml/min; T=30 C; Internal standard is compound 13. (See FIG. 9A)

Figure 9B:
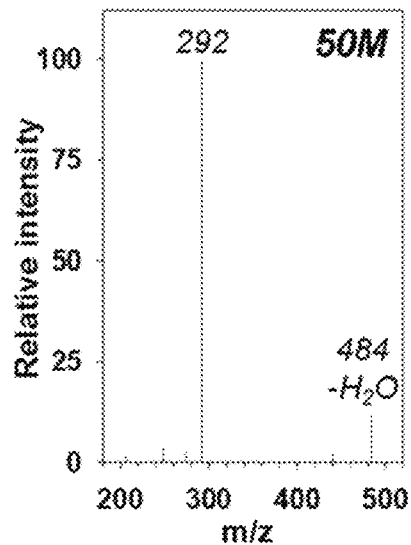
FIG. 9B is the mass spectrum of compound 50M.
Figure 9C:
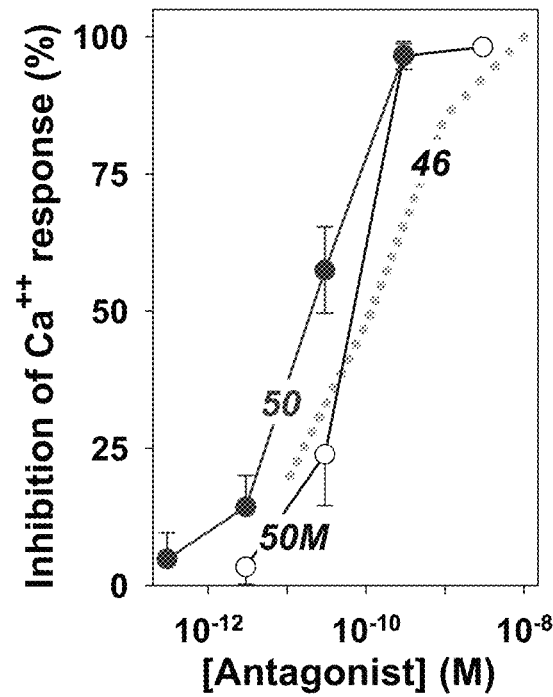
FIG. 9C is the OXE antagonistic activity curve against the concentration of compounds 50 and 50M.

Compound 50M was further identified by mass spectrometry (see FIG. 9B) under the following conditions:
Equipment: LTQ Orbitrap Velos; Electrospray ionization in negative ion mode
MS2 (collision-induced dissociation of M-H2O ion (m/z 484)
Compound 50M showed potent OXE antagonistic activity (see FIG. 9C)

As discussed above, compounds 46M, 49M, 50M and 54M, are 5-oxo-ETE-induced calcium mobilization inhibitors. The alpha-OH side chain of 5-(2-(alpha-OH-alkylphenyl)-indol-3-yl)-5-oxopentanoic acid compounds may therefore be advantageous over the 5-(2-(alpha-OH-alkyl)-indol-3-yl)-5-oxopentanoic acid compounds. For example, as seen in table 3 below, the reference compound V230M shows a significantly reduced IC50 compared to compounds 46M, 49M, 50M and 54M.

| Reference alpha-OH compound (V230M) | 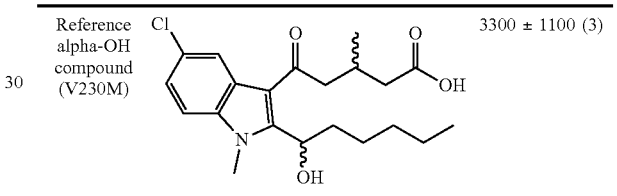 | 3300 ± 1100 (3) |
|---|---|---|

TABLE 3

| Compounds | Formula | IC50 (nM) |
|---|---|---|
| 46M | 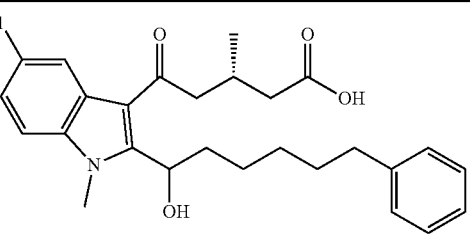 | 0.8 ± 0.3 (6) |
| 50M | 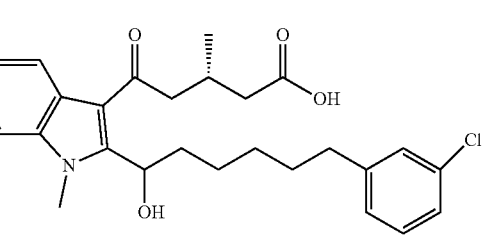 | 0.08 ± 0.02 (6) |

TABLE 3-continued

| Compounds | Formula | IC50 (nM) |
|---|---|---|
| 54M | 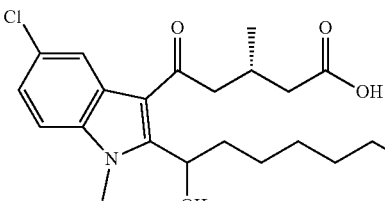 | 1.4 ± 0.4 (3) |
| 49M | 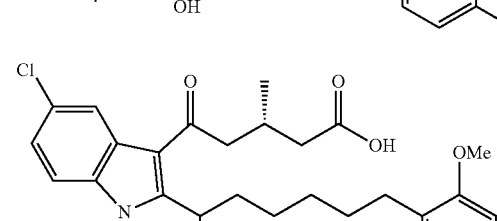 | 0.58 ± 0.21 (3) |

Synthesis of Compound 50M (and Enantiomer)

As an typical synthesis of alpha-OH compounds as described herein, compound 50M (and enantiome) will be prepared in accordance with the following scheme, according to which the Grignard reagent will be added to the indolyl aldehyde (4) as described in Scheme 1. The resulting hydroxyl residue will be protected using a silyl protecting group. The resulting compound will then undergo an acylation reaction as described above in schemes 1 and 5. The desired compound will be obtained after conducting a standard deprotection.

Scheme 11

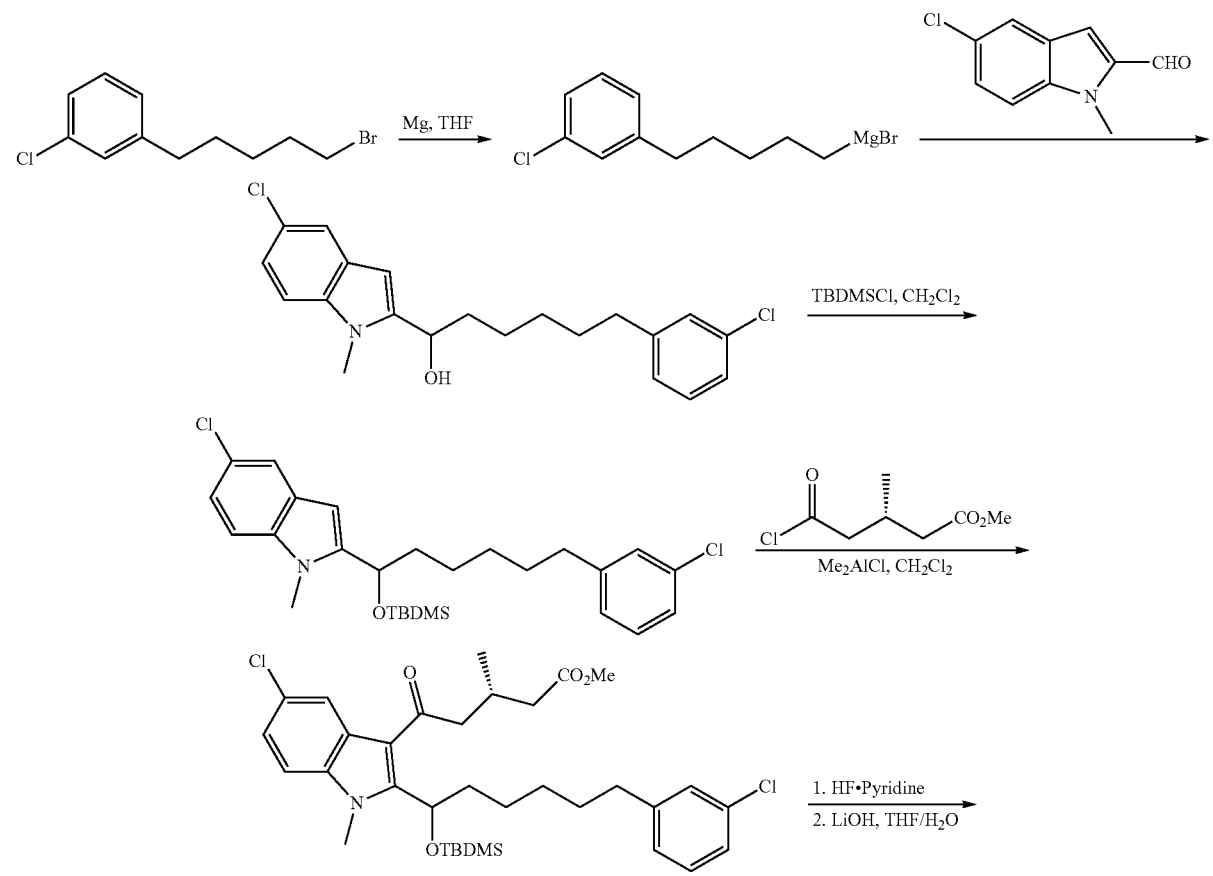

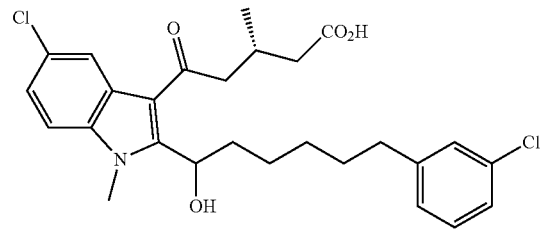

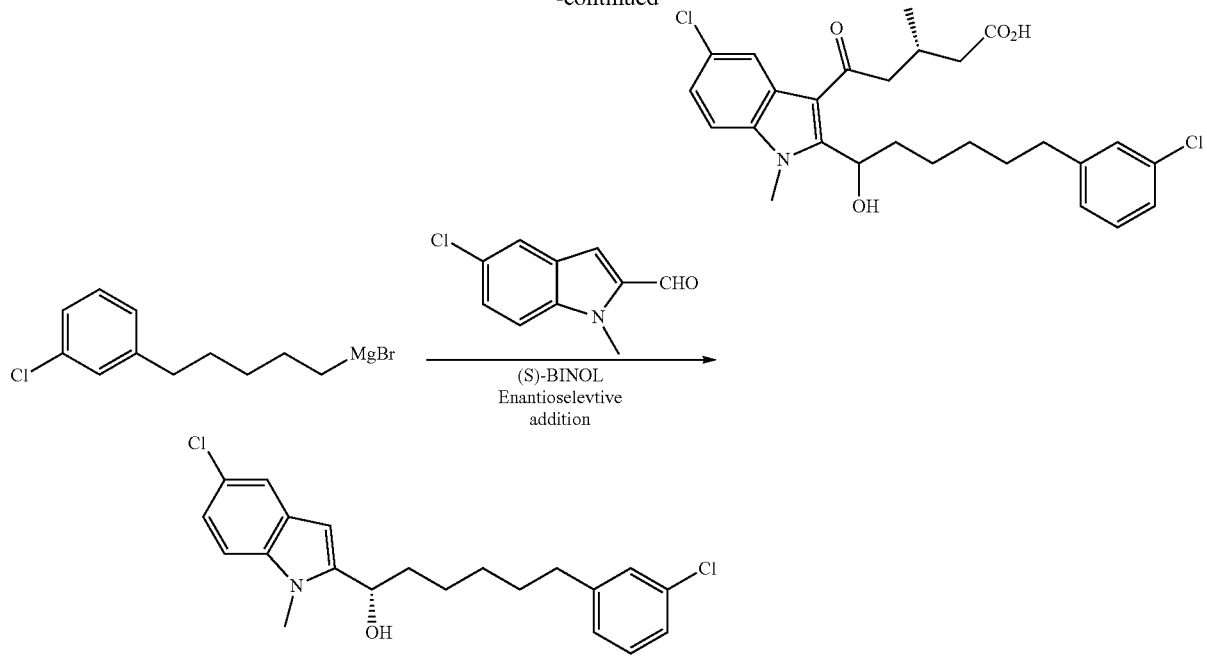

Inhibition of 5-Oxo-ETE-Induced Dermal Eosinophil Infiltration

Rhesus monkeys (n=6) were injected intradermally with 5-oxo-ETE (5 µg) or vehicle. Compound 50 (5 or 10 mg/kg) or vehicle were administered by oral gavage both 1 h before and 7 h after injection of 5-oxo-ETE.

Figure 10:
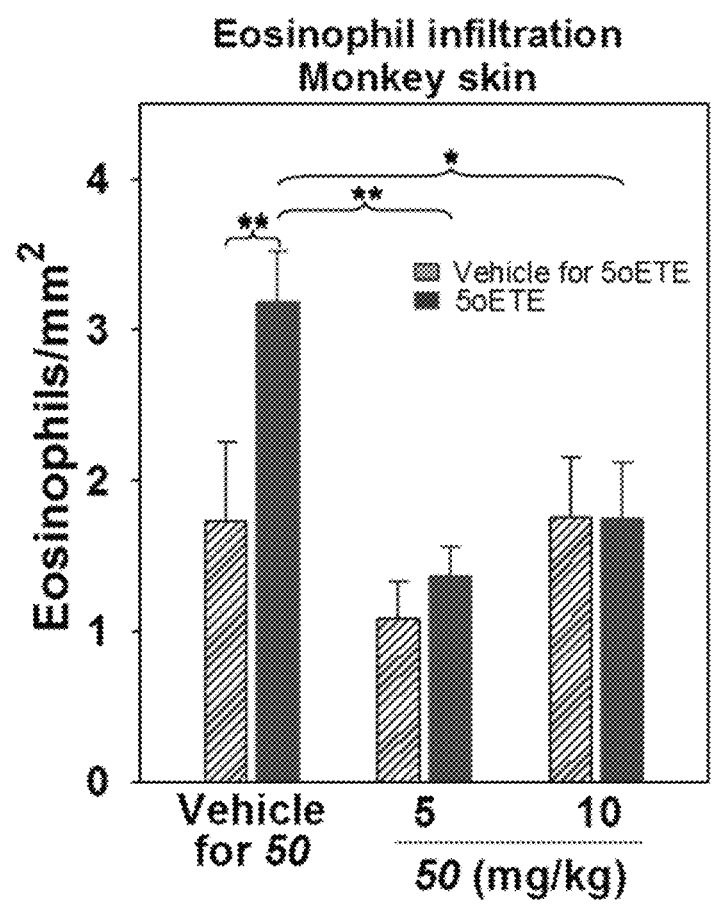
FIG. 10 represents the 5-oxo-ETE-induced dermal eosinophil infiltration after administration of compound 50 vs vehicle.

Skin biopsies were taken 24 h after administration of 5-oxo-ETE and sections from paraffin-embedded tissue were stained for eosinophil major basic protein, followed by counting of eosinophils. 5-Oxo-ETE-induced eosinophil infiltration was significantly inhibited by compound 50 at doses of both 5 mg/kg (p<0.005) and 10 mg/kg (p<0.02) (See FIG. 10)

While the disclosure provides specific embodiments, it is understood that it is capable of further modifications and that this application is intended to cover any variation, use, or adaptation of the embodiments following, in general, the principles and including such departures from the present disclosure that come within known, or customary practice within the art to which the invention pertains and as may be applied to the essential features hereinbefore set forth, and as follows in the scope of the appended claims. All references cited herein are incorporated by reference in their entirety.

The invention claimed is:

1. A compound of formula

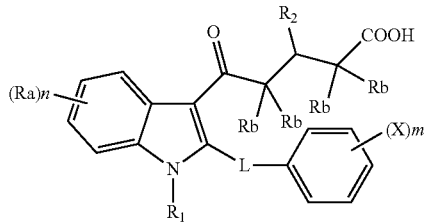

I or a pharmaceutically acceptable salt or solvate thereof; wherein $R_1$ is H, a straight or branched alkyl, or lower cycloalkyl;

$R_2$ is a lower straight or branched alkyl or lower cycloalkyl;

L is an alkylene chain of 4-7 members, an alkenylene chain of 4-7 members, a CH(OH)-alkylene chain wherein said alkylene chain in CH(OH)-alkylene chain has 4-6 members or an alkylene-O-alkylene chain wherein the two alkylene chains together in alkylene-O-alkylene chain have a total of 4-6 members;

Rb is H or F;

m is an integer of 0 to 5;

X is a substituent;

n is an integer of 0 to 4; and

Ra is a substituent.

2. The compound as defined in claim 1, having the formula

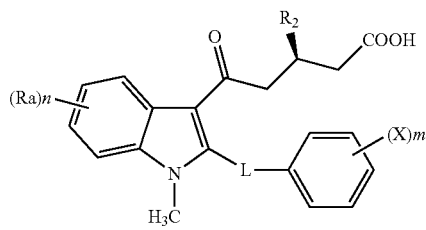

IV or a pharmaceutically acceptable salt or solvate thereof; wherein $R_2$, Ra, L, X, m and n are as defined in claim 1.

3. The compound as defined in claim 1, having the formula

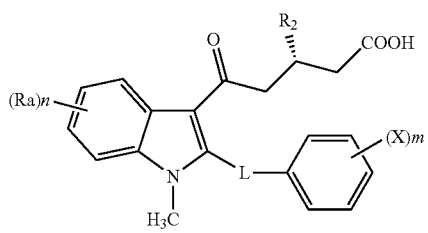

V or a pharmaceutically acceptable salt or solvate thereof; wherein $R_2$, Ra, L, X, m and n are as defined in claim 1.

4. The compound as defined in claim 1, wherein $R_1$ is a lower straight or branched alkyl; $R_2$ is a lower straight or branched alkyl; L is an alkylene chain of 4-6 members or a CH(OH)-alkylene chain wherein said alkylene chain in CH(OH)-alkylene chain has 4-6 members; is an integer of 0 to 3 and X is halogen, C1-6alkyl, C1-6 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-6alkyl; n is an integer of 0 to 3 and Ra is halogen, C1-6alkyl, C1-6 alkoxy, —NR40R41, —C(O)NR40R41, —NR40COR41, carboxy, hydroxyl, —S(O)$_{0-2}$R40, —C(O)R40, —C(O)OR40 or —SO$_2$NR40R41; wherein R40 and R41 are each independently H, or C1-6alkyl; and Rb is H.

5. The compound as defined in claim 1, wherein $R_1$ is a methyl, ethyl, n-propyl or isopropyl; $R_2$ is a methyl, ethyl, n-propyl or isopropyl; L is —CH(OH)—(CH$_2$)$_6$—, —(CH$_2$)$_7$—, —(CH$_2$)$_6$—, —CH(OH)—(CH$_2$)$_5$—, —CH$_2$—O—(CH$_2$)$_3$—, —(CH$_2$)$_2$—O—(CH$_2$)$_2$—, —(CH$_2$)$_3$—O—(CH$_2$)—, —CH=CH—(CH$_2$)$_4$—, —CH$_2$—CH=CH—(CH$_2$)$_3$—, —(CH$_2$)$_2$—CH=CH—(CH$_2$)$_2$—, or —(CH$_2$)$_3$—CH=CH—CH$_2$—; m is an integer of 0 to 2 and X is F, Cl, C1-3alkyl, C1-3 alkoxy, or hydroxyl; n is an integer of 0 to 2 and Ra is F, Cl, C1-3alkyl, C1-3 alkoxy, or hydroxyl; and Rb is H.

6. The compound as defined in claim 1, wherein $R_1$ is a lower straight or branched alkyl.

7. The compound as defined in claim 1, wherein $R_2$ is a lower straight or branched alkyl.

8. The compound as defined in claim 1, wherein

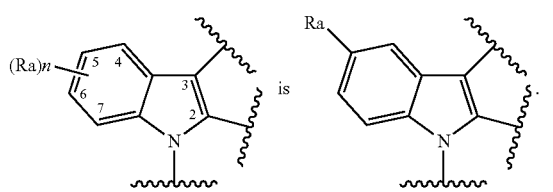

is

9. The compound as defined in claim 1, wherein L is —CH(OH)—(CH$_2$)$_6$—, —(CH$_2$)$_7$—, —(CH$_2$)$_6$—, —CH(OH)—(CH$_2$)$_5$—, —(CH$_2$)$_5$—, or —(CH$_2$)$_4$—.

10. The compound as defined in claim 1, wherein

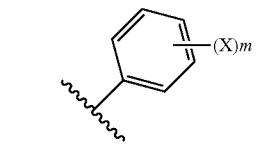

is any one of X1-X14:

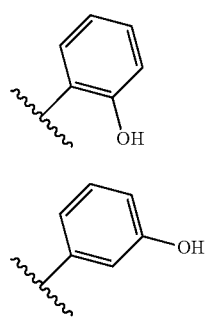

-continued
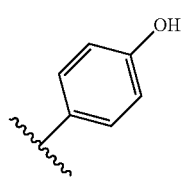
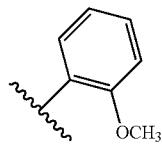
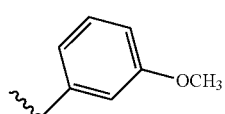
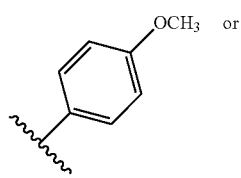 or
-continued
X10
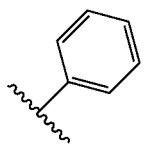
X11
X12
X13
X14
11. The compound as defined in claim 1 having the formula
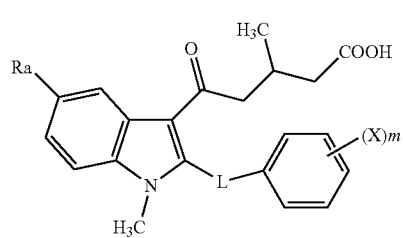
VIII
or a pharmaceutically acceptable salt or solvate thereof; wherein Ra, L, X and m are as defined in claim 1.
12. A compound as defined in table 2 or table 3:
TABLE 2
| Compounds | Formula |
|---|---|
| 15 | ![structure] |
| 13 | ![structure] |
| 14 | ![structure] |

TABLE 2-continued
| Compounds | Formula |
|---|---|
| 17 | 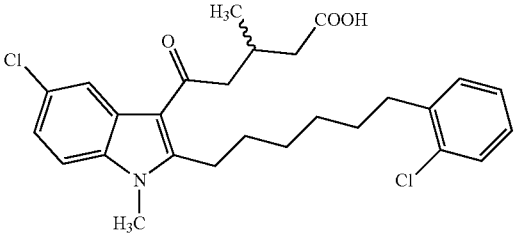 [SMILES: CC(CC(=O)O)CC(=O)c1c(CCCCCCc2ccccc2Cl)n(C)c2ccc(Cl)cc12] |
| 18 | 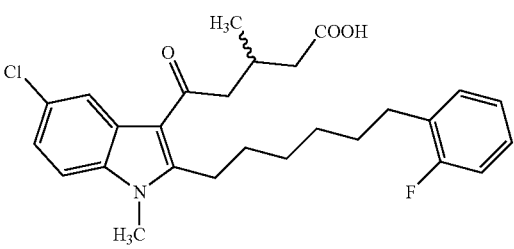 |
| 19 | 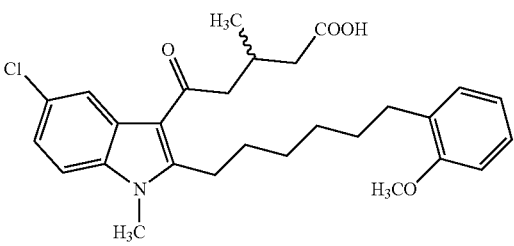 [SMILES: COc1ccccc1CCCCCCc1c(C(=O)CC(C)CC(=O)O)c2cc(Cl)ccc2n1C] |
| 20 | 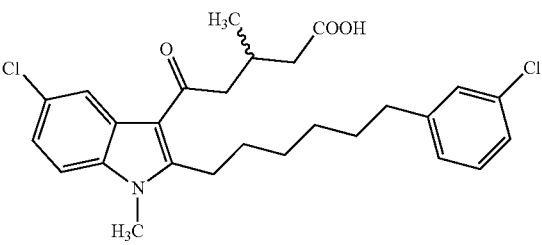 [SMILES: CC(CC(=O)O)CC(=O)c1c(CCCCCCc2cccc(Cl)c2)n(C)c2ccc(Cl)cc12] |
| 21 | 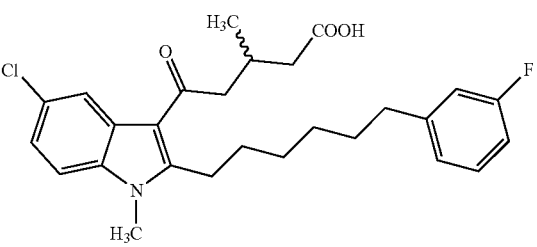 [SMILES: CC(CC(=O)O)CC(=O)c1c(CCCCCCc2cccc(F)c2)n(C)c2ccc(Cl)cc12] |
| 22 | 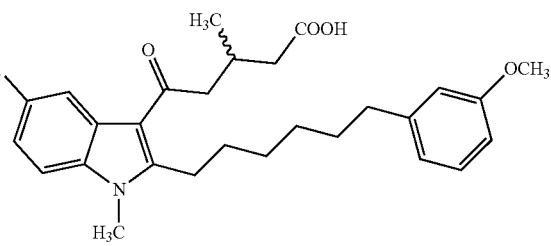 |

TABLE 2-continued

| Compounds | Formula |
|---|---|
| 23 | 5-chloro-1-methyl-2-(6-(4-chlorophenyl)hexyl)-indol-3-yl ketone with 3-methyl-4-oxo butanoic acid substituent |
| 24 | 5-chloro-1-methyl-2-(6-(4-fluorophenyl)hexyl)-indol-3-yl ketone with 3-methyl-4-oxo butanoic acid substituent |
| 25 | 5-chloro-1-methyl-2-(6-(4-methoxyphenyl)hexyl)-indol-3-yl ketone with 3-methyl-4-oxo butanoic acid substituent |
| 39 | 5-chloro-1-methyl-2-(6-(4-hydroxyphenyl)hexyl)-indol-3-yl ketone with 3-methyl-4-oxo butanoic acid substituent |
| 37 | 5-chloro-1-methyl-2-(6-(2-hydroxyphenyl)hexyl)-indol-3-yl ketone with 3-methyl-4-oxo butanoic acid substituent |
| 38 | 5-chloro-1-methyl-2-(6-(3-hydroxyphenyl)hexyl)-indol-3-yl ketone with 3-methyl-4-oxo butanoic acid substituent |

TABLE 2-continued

| Compounds | Formula |
|---|---|
| 46 | |
| 47 | |
| 48 | |
| 49 | |
| 50 | |
| 51 | |

TABLE 2-continued
| Compounds | Formula |
|---|---|
| 52 | 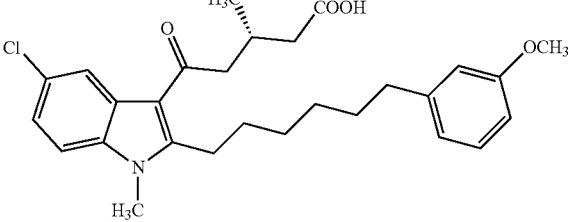 |
| 53 | 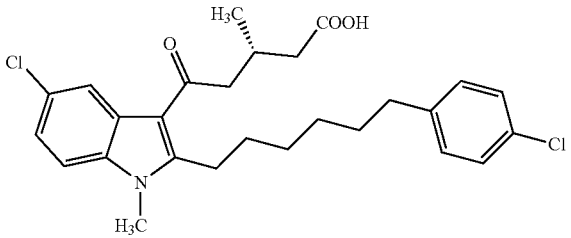 [SMILES: C[C@H](CC(=O)O)CC(=O)c1c(CCCCCCc2ccc(Cl)cc2)n(C)c2ccc(Cl)cc12] |
| 54 | 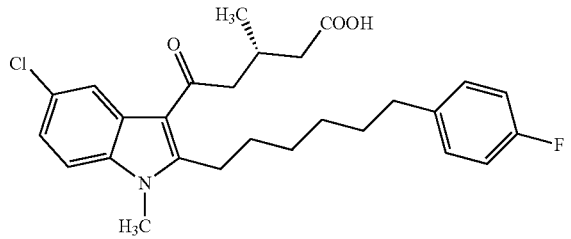 [SMILES: C[C@H](CC(=O)O)CC(=O)c1c(CCCCCCc2ccc(F)cc2)n(C)c2ccc(Cl)cc12] |
| 55 | 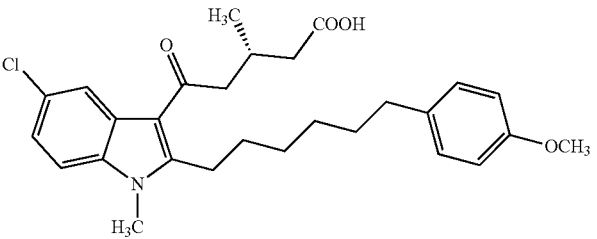 |
| 61 | 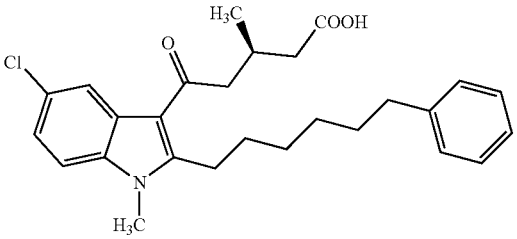 |
| 62 | 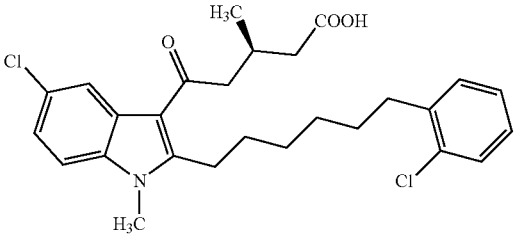 [SMILES: C[C@@H](CC(=O)O)CC(=O)c1c(CCCCCCc2ccccc2Cl)n(C)c2ccc(Cl)cc12] |

TABLE 2-continued

| Compounds | Formula |
|---|---|
| 63 | 5-chloro-1-methyl-2-[6-(2-fluorophenyl)hexyl]indol-3-yl ketone with (3S)-3-methyl-5-carboxypentanoyl group |
| 64 | 5-chloro-1-methyl-2-[6-(2-methoxyphenyl)hexyl]indol-3-yl ketone with (3S)-3-methyl-5-carboxypentanoyl group |
| 65 | 5-chloro-1-methyl-2-[6-(3-chlorophenyl)hexyl]indol-3-yl ketone with (3S)-3-methyl-5-carboxypentanoyl group |
| 66 | 5-chloro-1-methyl-2-[6-(3-fluorophenyl)hexyl]indol-3-yl ketone with (3S)-3-methyl-5-carboxypentanoyl group |
| 67 | 5-chloro-1-methyl-2-[6-(3-methoxyphenyl)hexyl]indol-3-yl ketone with (3S)-3-methyl-5-carboxypentanoyl group |
| 68 | 5-chloro-1-methyl-2-[6-(4-chlorophenyl)hexyl]indol-3-yl ketone with (3S)-3-methyl-5-carboxypentanoyl group |

TABLE 2-continued

| Compounds | Formula |
|---|---|
| 69 | 5-chloro-1-methyl-2-[6-(4-fluorophenyl)hexyl]-3-indolyl ketone with (3S)-3-methyl-4-carboxybutanoyl group |
| 70 | 5-chloro-1-methyl-2-[6-(4-methoxyphenyl)hexyl]-3-indolyl ketone with (3S)-3-methyl-4-carboxybutanoyl group |
| 83 | 5-chloro-1-methyl-2-[(3-phenylpropoxy)methyl]-3-indolyl ketone with 3-methyl-4-carboxybutanoyl group |
| 85 | 5-chloro-1-methyl-2-[(E)-6-phenylhex-1-enyl]-3-indolyl ketone with 3-methyl-4-carboxybutanoyl group |
| 94 | 5-chloro-1-methyl-2-[6-phenylhex-5-enyl (E/Z mixture)]-3-indolyl ketone with 3-methyl-4-carboxybutanoyl group |
| 95 | 5-chloro-1-methyl-2-[(Z)-6-phenylhex-5-enyl]-3-indolyl ketone with (3S)-3-methyl-4-carboxybutanoyl group |

TABLE 2-continued
| Compounds | Formula |
|---|---|
| 96 | 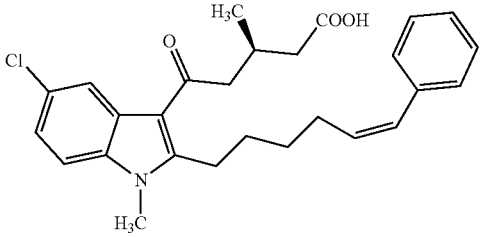 [SMILES: C[C@@H](CC(=O)O)CC(=O)c1c(CCCC/C=C\c2ccccc2)n(C)c2ccc(Cl)cc12] |
| 97 | 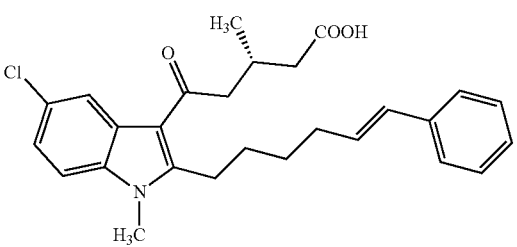 |
| 159 | 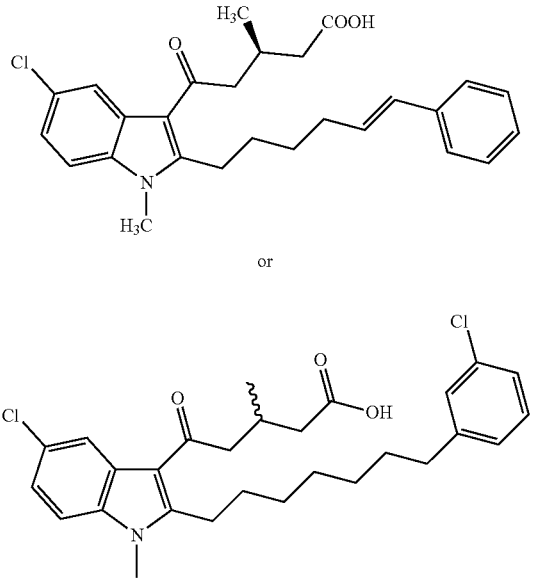 |
or

TABLE 3

| Compounds | Formula |
|---|---|
| 46M | 5-Cl-indole, N-Me, 2-(CH(OH)-(CH2)4-phenyl), 3-(C(O)-CH2-CH(Me)-CH2-COOH) |
| 50M | 5-Cl-indole, N-Me, 2-(CH(OH)-(CH2)4-(3-Cl-phenyl)), 3-(C(O)-CH2-CH(Me)-CH2-COOH) |
| 54M | 5-Cl-indole, N-Me, 2-(CH(OH)-(CH2)4-(4-F-phenyl)), 3-(C(O)-CH2-CH(Me)-CH2-COOH) |
| 49M | 5-Cl-indole, N-Me, 2-(CH(OH)-(CH2)4-(2-OMe-phenyl)), 3-(C(O)-CH2-CH(Me)-CH2-COOH) |

13. A pharmaceutical composition comprising the compound as defined in claim 1, or a pharmaceutically acceptable salt or solvate thereof, and one or more pharmaceutically acceptable carrier and/or excipient.

14. A method for treating a disease or condition selected from asthma, allergic rhinitis, chronic obstructive pulmonary disorder, atopic dermatitis, psoriasis and acne, the method comprising administering a therapeutically effective amount of the compound as defined in claim 1, or a pharmaceutically acceptable salt or solvate thereof, to a subject in need thereof.

* * * * *